(12) United States Patent
Wisniewski

(10) Patent No.: US 6,497,880 B1
(45) Date of Patent: Dec. 24, 2002

(54) **HEAT SHOCK GENES AND PROTEINS FROM *NEISSERIA MENINGITIDIS*, *CANDIDA GLABRATA* AND *ASPERGILLUS FUMIGATUS***

(75) Inventor: Jan Wisniewski, Sooke (CA)

(73) Assignee: Stressgen Biotechnologies Corporation, Victoria (CA)

( * ) Notice: Subject to any disclaimer, the term of this patent is extended or adjusted under 35 U.S.C. 154(b) by 0 days.

(21) Appl. No.: 09/207,388

(22) Filed: Dec. 8, 1998

(51) Int. Cl.⁷ .......................... A61K 39/02; C12Q 1/68; C12P 19/34; C07K 14/195; C07H 21/02

(52) U.S. Cl. ........................ 424/190.1; 435/6; 435/7.1; 435/91.1; 435/91.2; 530/350; 536/22.1; 536/23.1; 536/24.3; 536/23.4; 536/24.31; 536/24.32

(58) Field of Search .......................... 435/6, 7.1, 91.1; 530/350; 536/22.1, 23.1, 23.4, 23.7, 24.3, 24.31, 24.32, 24.33; 424/190.1

(56) References Cited

U.S. PATENT DOCUMENTS

| | | | |
|---|---|---|---|
| 4,716,038 A | 12/1987 | Stanford et al. | 424/92 |
| 4,724,144 A | 2/1988 | Rook et al. | 424/88 |
| 5,114,844 A | 5/1992 | Cohen et al. | 435/7.21 |
| 5,232,833 A | 8/1993 | Sanders et al. | 435/7.21 |
| 5,504,005 A | 4/1996 | Bloom et al. | 435/253.1 |

FOREIGN PATENT DOCUMENTS

| | | |
|---|---|---|
| CA | 1338778 | 12/1996 |
| EP | 262 710 A1 | 9/1987 |
| EP | 322 990 A1 | 7/1989 |
| EP | 419 569 B1 | 4/1991 |
| GB | 2 251 186 A | 7/1992 |
| WO | WO 85/05034 | 11/1985 |
| WO | WO 88/00974 | 2/1988 |
| WO | WO 88/05823 | 8/1988 |
| WO | WO 88/06591 | 9/1988 |
| WO | WO 89/12455 | 12/1989 |
| WO | WO 90/15873 | 12/1990 |
| WO | WO 91/02542 | 3/1991 |
| WO | WO 91/15572 | 10/1991 |
| WO | WO 92/08484 | 5/1992 |
| WO | WO 92/08488 | 5/1992 |
| WO | WO 93/17712 | 9/1993 |
| WO | WO 94/03208 | 2/1994 |
| WO | WO 94/29459 | 12/1994 |
| WO | WO 95/24923 | 9/1995 |
| WO | WO 96/10421 | 4/1996 |
| WO | WO 96/34116 | 10/1996 |
| WO | WO 96/40928 | 12/1996 |
| WO | WO 97/06821 | 2/1997 |
| WO | WO 97/26910 | 7/1997 |

OTHER PUBLICATIONS

Ardeshir et al., "A 75 kd merozoite surface protein of *Plasmodium falciparum* which is related to the 70 kd heat–shock proteins," *EMBO J.* 6(2): 493–499, 1987.

Barrios et al., "Heat shock proteins as carrier molecules: in vivo helper effect mediated by *Escherichia coli* GroEL and DnaK proteins requires cross–linking with antigen," *Clin. Exp. Immunol.* 98: 229–233, 1994.

Barrios et al., "Mycobacterial heat–shock proteins as carrier molecules. II: The use of the 70–kDa mycobacterial heat–shock protein as carrier for conjugated vaccines can circumvent the need for adjuvants and Bacillus Calmette Guérin priming," *Eur. J. Immunol.* 22:1365–1372, 1992.

Benkirane et al., "Identification of a *Streptococcus suis* 60–kDa heat–shock protein using Western blotting," *FEMS Microbiology Letters* 153:379–385, 1997.

Blander and Horwitz, "Major Cytoplasmic Membrane Protein of *Legionella pneumophila*, a Genus Common Antigen and Member of the hsp 60 Family of Heat Shock Proteins, Induces Protective Immunity in a Guinea Pig Model of Legionnaires' Disease," *J. Clin. Invest.* 91:717–723, 1993.

Dale and Beachy, "Multiple, Heart–Cross–Reactive Epitopes Of Streptococcal M Proteins," *J. Exp. Med.* 161:113–122, 1985.

Dale et al., "Recombinant Tetravalent Group A Streptococcal M Protein Vaccine," *The Journal of Immunology* 151(4):2188–2194, 1993.

De Velasco et al., "Synthetic Peptides Representing T–Cell Epitopes Act as Carriers in Pneumococcal Polysaccharide Conjugate Vaccines," *Infect. & Immun.* 63:961–968, 1995.

Del Giudice et al., "Heat Shock protein as "super"–carriers for sporozoite peptide vaccines?," *Res. In Immunol.* 162: 703–707, 1991.

Del Guidice et al., "Priming to Heat Shock Proteins in Infants Vaccinated against Pertussis," *J. Immunol.* 150(5): 2025–2032, 1993.

DeNagel and Pierce, "Heat Shock Proteins In Immune Responses," *Crit. Rev. Immunol.* 13(1): 71–81, 1993.

Dubois et al., "Protective immunization of the squirrel monkey against asexual blood stages of *Plasmodium falciparum* by use of parasite protein fractions," *Proc. Natl. Acad. Sci. USA* 81:229–232, 1984.

Egusa et al., "Heat Shock Proteins in Acute Otitis Media," *Laryngoscope 105*: 708–713, 1995.

Ferrero et al., "The GroES homolog of *Helicobacter pylori* confers protective immunity against mucosal infection in mice," *Proc. Natl. Acad. Sci. USA* 92: 6499–6503, 1995.

(List continued on next page.)

*Primary Examiner*—Jeffrey Siew
(74) *Attorney, Agent, or Firm*—Fish & Richardson P.C.

(57) ABSTRACT

Methods and compositions comprising isolated nucleic acid molecules specific to *Neisseria meningitidis*, *Candida glabrata* and *Aspergillus fumigatus* heat shock proteins (Hsps), as well as vector constructs and isolated polypeptides specific to the same are provided. Such compositions and methods are useful for the diagnosis of infections by these organisms and for generating an immune response to the organisms.

17 Claims, 34 Drawing Sheets

OTHER PUBLICATIONS

Friedland et al., "Mycobacterial 65–kD heat shock protein induces release of proinflammatory cytokines from human monocytic cells," *Clin. Exp. Immunol.* 91: 58–62, 1993.

Gomez et al., "Vaccination with Recombinant Heat Shock Protein 60 from *Histoplasma capsulatum* Protects Mice against Pulmonary Histoplasmosis," *Infect & Immun.* 63: 2587–2595, 1995.

Hamel et al., "Heat shock response of *Streptococcus pneumoniae:* identification of immunoreactive stress proteins," *Microbial Pathogenesis* 23:11–21, 1997.

Husson and Young, "Genes for the major protein antigens of *Mycobacterium tuberculosis:* the etiologic agents of tuberculosis and leprosy share an immunodominant antigen," *Proc. Natl. Acad. Sci. USA* 84: 1679–1683, 1987.

Kaufman et al., "Enumeration of T cells reactive with Mycobacterium tuberculosis organisms and specific for the recombinant mycobacterial 64–kDa protein," *Eur. J. Immunol.* 17: 351–357, 1987.

Kim et al., "Determinants of T Cell Reactivity to the *Mycobacterium leprae* GroES Homologue," *Journal of Immunology* 159(1):335–343, 1997.

Könen–Waisman et al., "Self and Foreign 60–Kilodalton Heat Shock Protein T Cell Epitope Peptides Serve As Immunogenic Carriers for a T Cell–Independent Sugar Antigen1," *J. Immunol.* 154: 5977–5985, 1995.

Lamb et al., "Stress Proteins may Provide a Link Between the Immune Response to Infection and Autoimmunity," *Intl. Immun.* 1(2): 191–196, 1989.

Levi and Arnon, "Synthetic recombinant influenza vaccine induces efficient long–term immunity and cross–strain protection," *Vaccine* 14(1): 85–92, 1996.

Lindler and Hayes, "Nucleotide sequence of the *Salmonella typhi groEL* heat shcok gene," *Microbiol Pathogenesis* 17:271–275, 1994.

Lindquist and Craig, "The Heat–Shock Proteins," *Annu. Rev. Genet.* 22: 631–677, 1988.

Lussow et al., "Mycobacterial heat–shock proteins as carrier molecules," *Eur. J. Immunol.* 21: 2297–2302, 1991.

Macario, "Heat–shock proteins and molecular chaperones: implications for pathogenesis, diagnostics, and therapeutics," *Int. J. Clin. Lab. Res.* 25:59–70, 1995.

Noll and Autenrietii, "Immunity against *Yersinia enterocolitica* by Vaccination with Yersinia HSP60 Immunostimulating Complexes or Yersinia HSP60 plus Interleukin–12," *Infect. & Immun.* 64: 2955–2961, 1996.

Parsell and Lidquist, "The Function Of Heat–Shock Proteins In Stress Tolerance: Degradation And Reactivation Of Damaged Proteins," *Ann. Rev. Genet.* 27:437–496, 1993.

Robinson and Kehoe, "Group A streptococcal M. proteins: virulence factors and protective antigens," *Immunology Today* 13(9):362–367, 1992.

Segal, "Vaccines Against Fungal Infections," *CRC Crit. Rev. Microbiology* 14(3):229–271, 1987.

Srivastava and Udono, "Heat shock protein–peptide complexes in cancer immunotherapy," *Curr. Opin. Immunol.* 6: 728–732, 1994.

Suzue and Young, "Adjuvant–Free hsp70 Fusion Protein System Elicits Humoral and Cellular Immune Responses to HIV–1 p24[1]," *J. Immunol.* 156: 873–879, 1996.

Suzue and Young, "Heat shock proteins as immunological carriers and vaccines," *Stress–Inducible Cellular Responses,* Feige et al. (eds.), Birkhäuser Verlag Basel, Switzerland, 1996, pp. 451–465.

Tang et al., "Induction and Characterization of Heat Shock Proteins of *Salmonella typhi* and Their Reactivity with Sera from Patients with Typhoid Fever," *Infection and Immunity* 65(7):2983–2986, 1997.

Thole et al., "Characterization, Sequence Determination, and Immunogenicity of a 64–Kilodalton Protein of *Mycobacterium bovis* BCG Expressed in *Escherichia coli* K–12," *Infect. Immunol.* 55(6): 1466–1470, 1987.

Verdegaal et al., "Heat Shock Protein 65 Induces CD62e, CD106, and CD54 on Cultured Human Endothelial Cells and Increases Their Adhesiveness for Monocytes and Granulocytes," *J. Immunol.* 157: 369–376, 1996.

Vodkin and Williams, "A Heat Shock Operon in *Coxiella burnetti* Produces a Major Antigen Homologous to a Protein in Both Mycobacteria and *Escherichia coli,"* *J. Bact.* 170(3): 1227–1234, 1988.

Young et al., "Stress Proteins are immune targets in leprosy and tuberculosis," *Proc. Natl. Acad. Sci. USA* 85: 4267–4270, 1988.

Young et al., "The 65kDa antigen of mycobacteria—a common bacterial protein?," *Immunol. Today* 8(7–8): 215–219, 1987.

Young, "Stress Proteins and Immunology," *Ann. Rev. Immunol.* 8:401–420, 1990.

Zuo et al., "Multiple Layers of Regulation of Human Heat Shock Transcription Factor 1," *Molecular And Cellular Biology* 15(8):4319–4330, 1995.

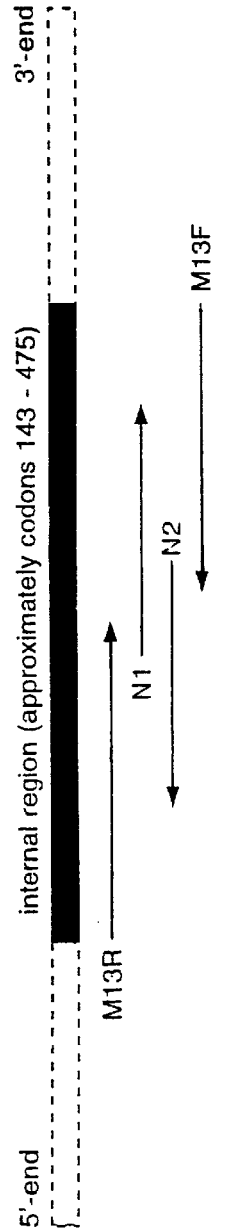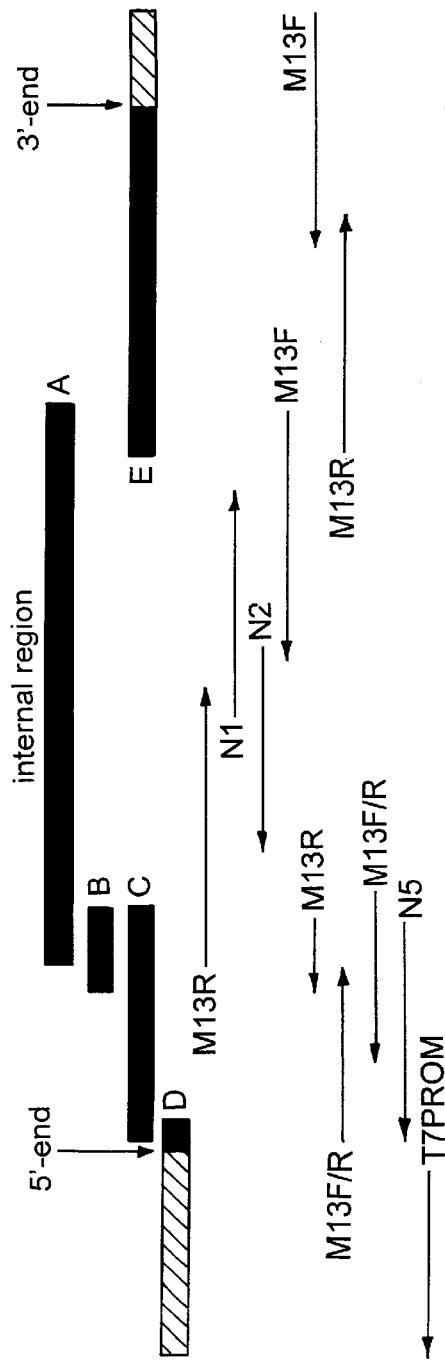

```
1/1                                         31/11
CCT GCD TAT TTC AAC GAC AGC CAA CGT CAA GCC ACC AAA GAC GCA GGC CGT ATC GCC GGT
 P   A   Y   F   N   D   S   Q   R   Q   A   T   K   D   A   G   R   I   A   G
61/21                                       91/31
TTG GAC GTG AAA CGC ATC ATC AAC GAG CCG ACC GCA GCC GCT TTG GCA TTC GGT ATG GAC
 L   D   V   K   R   I   I   N   E   P   T   A   A   A   L   A   F   G   M   D
121/41                                      151/51
AAA GGC GAC AAC AAA GAC CGC AAA GTA GCC GTA TAT GAC TTG GGC GGC GGT ACT TTC GAT
 K   G   D   N   K   D   R   K   V   A   V   Y   D   L   G   G   G   T   F   D
181/61                                      211/71
ATT TCC ATC ATC GAA ATC GCC AAC CTC GAC GGC GAC AAA CAA TTC GAA GTA TTG GCA ACC
 I   S   I   I   E   I   A   N   L   D   G   D   K   Q   F   E   V   L   A   T
241/81                                      271/91
AAC GGC GAT ACC TTC TTG GGC GGT GAA GAC TTC GAC CAA CGC CTC ATC GAC CAC ATC ATC
 N   G   D   T   F   L   G   G   E   D   F   D   Q   R   L   I   D   H   I   I
301/101                                     331/111
GCC GAG TTC AAA AAA GAA CAA GGC ATT GAT TTG AAA CAA GAC GTG ATG GCT CTA CAA CGC
 A   E   F   K   K   E   Q   G   I   D   L   K   Q   D   V   M   A   L   Q   R
361/121                                     391/131
CTG AAA GAA GCT GCC GAA AAA GCC AAA ATC GAA TTG TCC AGC GGC CAG CAA ACC GAA ATT
 L   K   E   A   A   E   K   A   K   I   E   L   S   S   G   Q   Q   T   E   I
421/141                                     451/151
AAC CTG CCG TAC ATC ACC ATG GAC GCA ACC GGC CCG AAA CAC TTG GCG ATG AAA ATT ACC
 N   L   P   Y   I   T   M   D   A   T   G   P   K   H   L   A   M   K   I   T
481/161                                     511/171
CGC GCC AAA TTC GAA AGC CTG GTT GAA GAC CTG ATT ACC CGC TCT ATC GAA CCT TGC AAA
 R   A   K   F   E   S   L   V   E   D   L   I   T   R   S   I   E   P   C   K
541/181                                     571/191
ATT GCA TTG AAA GAT GCC GGC TTG AGC ACC GGC GAC ATC GAC GAC GTA ATC TTG GTC GGC
 I   A   L   K   D   A   G   L   S   T   G   D   I   D   D   V   I   L   V   G
601/201                                     631/211
GGG CAG TCC CGT ATG CCG AAA GTA CAA GAA GCC GTT AAA GCC TTC TTC GGC AAA GAA CCG
 G   Q   S   R   M   P   K   V   Q   E   A   V   K   A   F   F   G   K   E   P
661/221                                     691/231
CGC AAA GAC GTG AAC CCT GAC GAA GCC GTT GCC GTA GGC GCA GCG ATC CAA GGC GAA GTA
 R   K   D   V   N   P   D   E   A   V   A   V   G   A   A   I   Q   G   E   V
721/241                                     751/251
TTG AGC GGC GGC CGC AGC GAC GTA TTG CTA CTG GAC GTA ACT CCT CTG TCT TTG GGT ATC
 L   S   G   G   R   S   D   V   L   L   L   D   V   T   P   L   S   L   G   I
781/261                                     811/271
GAA ACC ATG GGC GGC GTG ATG ACC AAA CTG ATT CAG AAG AAC ACC ACC ATC CCG ACC AAA
 E   T   M   G   G   V   M   T   K   L   I   Q   K   N   T   T   I   P   T   K
841/281                                     871/291
GCG TCG CAA GTG TTC TCT ACC GCC GAA GAC AAC CAA AGC GCA GTA ACC ATC CAC GTA CTG
 A   S   Q   V   F   S   T   A   E   D   N   Q   S   A   V   T   I   H   V   L
901/301                                     931/311
CAA GGC GAA CGC GAA CGC GCT TCT GCC AAC AAA TCT TTG GGT CAG TTC AAC TTG GGC GAC
 Q   G   E   R   E   R   A   S   A   N   K   S   L   G   Q   F   N   L   G   D
961/321                                     991/331
ATC GCA CCT GCA CCG CGC GGT ATG CCA CAA ATC GAA GTA ACH TTT
 I   A   P   A   P   R   G   M   P   Q   I   E   V   T   F
```

FIG. 2

1 CAATTCAACA

TACTGAACGC CAAAGATATG GATGCAGAAC AAGTCTCCCT TTCCAAAGAA TGCGACATCA TCGAGTCTTC

ACACGACTGG GAAAAAGAGT ACGGCAACTT GAACGAACAG GAAATGCTCG CCGGCATCGT CTATGAATAA

ACCTGCCTGC CATTTGAAAC ATTATGCTTG AATGCATTGG AGCCAAATGT ATTAAATCAA ATATAAAACC

AATATATTCA TAAAGTTATA TACTTATAGC CATGCTGTAG CTTGAAACAG TTCCAACATA CCCGCCGCCC

GCCCTATTTA CAGCCCATCG GGACAAAATG TTTCTCAAAA TAAGCAAAAT CAAATAGGAT TATCCAC 357

358/1                                388/11
ATG GCA AAA GTA ATC GGT ATC GAC TTA GGT ACA ACC AAC TCT TGT TTG GCC ATT TCC GAA
 M   A   K   V   I   G   I   D   L   G   T   T   N   S   C   L   A   I   S   E
418/21                               448/31
AAC GGT CAA ACC AAA GTG ATC GAA AAC GCA GAA GGC GCA CGC ACC ACG CCG TCC GTT ATC
 N   G   Q   T   K   V   I   E   N   A   E   G   A   R   T   T   P   S   V   I
478/41                               508/51
GCT TAT TTG GAC GGC GGC GAA ATC CTC GTC GGT GCG CCT GCC AAA CGC CAA GCG GTA ACC
 A   Y   L   D   G   G   E   I   L   V   G   A   P   A   K   R   Q   A   V   T
538/61                               568/71
AAC GCC AAA AAC ACC ATT TAC GCC GCC AAA CGT TTG ATC GGC CAC AAA TTT GAA GAC AAA
 N   A   K   N   T   I   Y   A   A   K   R   L   I   G   H   K   F   E   D   K
598/81                               628/91
GAA GTC CAA CGC GAC ATC GAA TCT ATG CCT TTC GAA ATC ATC AAA GCC AAC AAC GGC GAC
 E   V   Q   R   D   I   E   S   M   P   F   E   I   I   K   A   N   N   G   D
658/101                              688/111
GCA TGG GTA AAA GCA CAA GGC AAA GAG CTG TCT CCT CCT CAA ATT TCC GCA GAA GTC CTG
 A   W   V   K   A   Q   G   K   E   L   S   P   P   Q   I   S   A   E   V   L
718/121                              748/131
CGT AAA ATG AAA GAA GCC GCC GAA GCT TAC TTG GGC GAA AAA GTA ACC GAA GCC GTG ATT
 R   K   M   K   E   A   A   E   A   Y   L   G   E   K   V   T   E   A   V   I
778/141                              808/151
ACC GTC CCT GCC TAC TTC AAC GAC AGC CAA CGT CAA GCC ACC AAA GAC GCA GGC CGT ATC
 T   V   P   A   Y   F   N   D   S   Q   R   Q   A   T   K   D   A   G   R   I
838/161                              868/171
GCC GGT TTG GAC GTG AAA CGC ATC ATC AAC GAG CCG ACC GCA GCC GCT TTG GCA TTC GGT
 A   G   L   D   V   K   R   I   I   N   E   P   T   A   A   A   L   A   F   G
898/181                              928/191
ATG GAC AAA GGC GAC AAC AAA GAC CGC AAA GTA GCC GTA TAT GAC TTG GGC GGC GGT ACT
 M   D   K   G   D   N   K   D   R   K   V   A   V   Y   D   L   G   G   G   T
958/201                              988/211
TTC GAT ATT TCC ATC ATC GAA ATC GCC AAC CTC GAC GGC GAC AAA CAA TTC GAA GTA TTG
 F   D   I   S   I   I   E   I   A   N   L   D   G   D   K   Q   F   E   V   L
1018/221                             1048/231
GCA ACC AAC GGC GAT ACC TTC TTG GGC GGT GAA GAC TTC GAC CAA CGC CTC ATC GAC CAC
 A   T   N   G   D   T   F   L   G   G   E   D   F   D   Q   R   L   I   D   H
1078/241                             1108/251
ATC ATC GCC GAG TTC AAA AAA GAA CAA GGC ATT GAT TTG AAA CAA GAC GTG ATG GCT CTA
 I   I   A   E   F   K   K   E   Q   G   I   D   L   K   Q   D   V   M   A   L
1138/261                             1168/271
CAA CGC CTG AAA GAA GCT GCC GAA AAA GCC AAA ATC GAA TTG TCC AGC GGC CAG CAA ACC
 Q   R   L   K   E   A   A   E   K   A   K   I   E   L   S   S   G   Q   Q   T
1198/281                             1228/291
GAA ATT AAC CTG CCG TAC ATC ACC ATG GAC GCA ACC GGC CCG AAA CAC TTG GCG ATG AAA

FIG. 4A

```
          E   I   N   L   P   Y   I   T   M   D       A   T   G   P   K   H   L   A   M   K
      1258/301                                     1288/311
      ATT ACC CGC GCC AAA TTC GAA AGC CTG GTT   GAA GAC CTG ATT ACC CGC TCT ATC GAA CCT
       I   T   R   A   K   F   E   S   L   V       E   D   L   I   T   R   S   I   E   P
      1318/321                                     1348/331
      TGC AAA ATT GCA TTG AAA GAT GCC GGC TTG   AGC ACC GGC GAC ATC GAC GAC GTA ATC TTG
       C   K   I   A   L   K   D   A   G   L       S   T   G   D   I   D   D   V   I   L
      1378/341                                     1408/351
      GTC GGC GGG CAG TCC CGT ATG CCG AAA GTA   CAA GAA GCC GTT AAA GCC TTC TTC GGC AAA
       V   G   G   Q   S   R   M   P   K   V       Q   E   A   V   K   A   F   F   G   K
      1438/361                                     1468/371
      GAA CCG CGC AAA GAC GTG AAC CCT GAC GAA   GCC GTT GCC GTA GGC GCA GCG ATC CAA GGC
       E   P   R   K   D   V   N   P   D   E       A   V   A   V   G   A   A   I   Q   G
      1498/381                                     1528/391
      GAA GTA TTG AGC GGC GGC CGC AGC GAC GTA   TTG CTA CTG GAC GTA ACT CCT CTG TCT TTG
       E   V   L   S   G   G   R   S   D   V       L   L   L   D   V   T   P   L   S   L
      1558/401                                     1588/411
      GGT ATC GAA ACC ATG GGC GGC GTG ATG ACC   AAA CTG ATT CAG AAG AAC ACC ACC ATC CCG
       G   I   E   T   M   G   G   V   M   T       K   L   I   Q   K   N   T   T   I   P
      1618/421                                     1648/431
      ACC AAA GCG TCG CAA GTG TTC TCT ACC GCC   GAA GAC AAC CAA AGC GCA GTA ACC ATC CAC
       T   K   A   S   Q   V   F   S   T   A       E   D   N   Q   S   A   V   T   I   H
      1678/441                                     1708/451
      GTA CTG CAA GGC GAA CGC GAA CGC GCT TCT   GCC AAC AAA TCT TTG GGT CAG TTC AAC TTG
       V   L   Q   G   E   R   E   R   A   S       A   N   K   S   L   G   Q   F   N   L
      1738/461                                     1768/471
      GGC GAC ATC GCA CCT GCA CCG CGC GGT ATG   CCG CAA ATC GAA GTA ACC TTC GAC ATC GAC
       G   D   I   A   P   A   P   R   G   M       P   Q   I   E   V   T   F   D   I   D
      1798/481                                     1828/491
      GCC AAC GGC ATC CTG CAC GTT TCC GCC AAA   GAC AAA GGC ACC GGT AAA GCA GCC AAC ATC
       A   N   G   I   L   H   V   S   A   K       D   K   G   T   G   K   A   A   N   I
      1858/501                                     1888/511
      ACC ATC CAA GGT TCT TCA GGT TTG GGC GAA   GAA GAA ATC GAA CGC ATG GTG AAA GAT GCC
       T   I   Q   G   S   S   G   L   G   E       E   E   I   E   R   M   V   K   D   A
      1918/521                                     1948/531
      GAA GCC AAT GCC GAG GAA GAT AAA AAA CTG   ACT GAA TTG GTC GCT TCC CGC AAC CAA GCC
       E   A   N   A   E   E   D   K   K   L       T   E   L   V   A   S   R   N   Q   A
      1978/541                                     2008/551
      GAA GCC CTG ATT CAC TCT GTG AAG AAA TCT   TTG GCC GAC TAC GGC GAC AAA CTC GAT GCA
       E   A   L   I   H   S   V   K   K   S       L   A   D   Y   G   D   K   L   D   A
      2038/561                                     2068/571
      GCC GAG AAA GAA AAA ATT GAA GCC GCG CTG   AAA GAA GCC GAA GAA GCA GTT AAA GGC GAC
       A   E   K   E   K   I   E   A   A   L       K   E   A   E   E   A   V   K   G   D
      2098/581                                     2128/591
      GAC AAA GCC GCT ATC GAT GCC AAA ACC GAG   GCG CTG GGC GCA GCC AGC CAA AAA CTG GGG
       D   K   A   A   I   D   A   K   T   E       A   L   G   A   A   S   Q   K   L   G
      2158/601                                     2188/611
      GAA ATG GTT TAC GCT CAA GCA CAA GCT GAA   GCC CAA GCA GGC GAA AGC GAA CAA GCC AAT
       E   M   V   Y   A   Q   A   Q   A   E       A   Q   A   G   E   S   E   Q   A   N
      2218/621                                     2248/631
      GCT TCT GCA AAG AAA GAC GAT GAT GTC GTA   GAT GCC GAC TTT GAA GAA GTA AAA GAC GAC
       A   S   A   K   K   D   D   D   V   V       D   A   D   F   E   E   V   K   D   D
      2278/641
      AAA AAA TAA      TTAA TACCGTCTGA AAAAAGCGCG AACCGTTTGA TTCGCGCTTT TTTCAATTGA
       K   K   *
      GATAAAAGAC CATAGCATAA CAGAGGTTCC AAGTTCATCT ACCGTAATAT TCCCAAACCC AgGTTCCAAC

TGTTGTATCG GTTCTCTGGA ATTTTTTATA TAGTGGATTA AATTTAAACC AGTAC  2465   FIG. 4B
```

```
4/1                                    34/11
ATG GCA AAA GTA ATC GGT ATC GAC TTA GGT ACA ACC AAC TCT TGT TTG GCC ATT TCC GAA
 M   A   K   V   I   G   I   D   L   G   T   T   N   S   C   L   A   I   S   E
64/21                                  94/31
AAC GGT CAA ACC AAA GTG ATC GAA AAC GCA GAA GGC GCA CGC ACC ACG CCG TCC GTT ATC
 N   G   Q   T   K   V   I   E   N   A   E   G   A   R   T   T   P   S   V   I
124/41                                 154/51
GCT TAT TTG GAC GGC GGC GAA ATC CTC GTC GGT GCG CCT GCC AAA CGC CAA GCG GTA ACC
 A   Y   L   D   G   G   E   I   L   V   G   A   P   A   K   R   Q   A   V   T
184/61                                 214/71
AAC GCC AAA AAC ACC ATT TAC GCC GCC AAA CGT TTG ATC GGC CAC AAA TTT GAA GAC AAA
 N   A   K   N   T   I   Y   A   A   K   R   L   I   G   H   K   F   E   D   K
244/81                                 274/91
GAA GTC CAA CGC GAC ATC GAA TCT ATG CCT TTC GAA ATC ATC AAA GCC AAC AAC GGC GAC
 E   V   Q   R   D   I   E   S   M   P   F   E   I   I   K   A   N   N   G   D
304/101                                334/111
GCA TGG GTA AAA GCA CAA GGC AAA GAG CTG TCT CCT CCT CAA ATT TCC GCA GAA GTC CTG
 A   W   V   K   A   Q   G   K   E   L   S   P   P   Q   I   S   A   E   V   L
364/121                                394/131
CGT AAA ATG AAA GAA GCC GCC GAA GCT TAC TTG GGC GAA AAA GTA ACC GAA GCC GTG ATT
 R   K   M   K   E   A   A   E   A   Y   L   G   E   K   V   T   E   A   V   I
424/141                                454/151
ACC GTC CCT GCC TAC TTC AAC GAC AGC CAA CGT CAA GCC ACC AAA GAC GCA GGC CGT ATC
 T   V   P   A   Y   F   N   D   S   Q   R   Q   A   T   K   D   A   G   R   I
484/161                                514/171
GCC GGT TTG GAC GTG AAA CGC ATC ATC AAC GAG CCG ACC GCA GCC GCT TTG GCA TTC GGT
 A   G   L   D   V   K   R   I   I   N   E   P   T   A   A   A   L   A   F   G
544/181                                574/191
ATG GAC AAA GGC GAC AAC AAA GAC CGC AAA GTA GCC GTA TAT GAC TTG GGC GGC GGT ACT
 M   D   K   G   D   N   K   D   R   K   V   A   V   Y   D   L   G   G   G   T
604/201                                634/211
TTC GAT ATT TCC ATC ATC GAA ATC GCC AAC CTC GAC GGC GAC AAA CAA TTC GAA GTA TTG
 F   D   I   S   I   I   E   I   A   N   L   D   G   D   K   Q   F   E   V   L
664/221                                694/231
GCA ACC AAC GGC GAT ACC TTC TTG GGC GGT GAA GAC TTC GAC CAA CGC CTC ATC GAC CAC
 A   T   N   G   D   T   F   L   G   G   E   D   F   D   Q   R   L   I   D   H
724/241                                754/251
ATC ATC GCC GAG TTC AAA AAA GAA CAA GGC ATT GAT TTG AAA CAA GAC GTG ATG GCT CTA
 I   I   A   E   F   K   K   E   Q   G   I   D   L   K   Q   D   V   M   A   L
784/261                                814/271
CAA CGC CTG AAA GAA GCT GCC GAA AAA GCC AAA ATC GAA TTG TCC AGC GGC CAG CAA ACC
 Q   R   L   K   E   A   A   E   K   A   K   I   E   L   S   S   G   Q   Q   T
844/281                                874/291
GAA ATT AAC CTG CCG TAC ATC ACC ATG GAC GCA ACC GGC CCG AAA CAC TTG GCG ATG AAA
 E   I   N   L   P   Y   I   T   M   D   A   T   G   P   K   H   L   A   M   K
904/301                                934/311
ATT ACC CGC GCC AAA TTC GAA AGC CTG GTT GAA GAC CTG ATT ACC CGC TCT ATC GAA CCT
 I   T   R   A   K   F   E   S   L   V   E   D   L   I   T   R   S   I   E   P
964/321                                994/331
TGC AAA ATT GCA TTG AAA GAT GCC GGC TTG AGC ACC GGC GAC ATC GAC GAC GTA ATC TTG
 C   K   I   A   L   K   D   A   G   L   S   T   G   D   I   D   D   V   I   L
1024/341                               1054/351
GTC GGC GGG CAG TCC CGT ATG CCG AAA GTA CAA GAA GCC GTT AAA GCC TTC TTC GGC AAA
 V   G   G   Q   S   R   M   P   K   V   Q   E   A   V   K   A   F   F   G   K
```

FIG. 6A

```
1084/361                                          1114/371
GAA CCG CGC AAA GAC GTG AAC CCT GAC GAA GCC GTT GCC GTA GGC GCA GCG ATC CAA GGC
 E   P   R   K   D   V   N   P   D   E   A   V   A   V   G   A   A   I   Q   G
1144/381                                          1174/391
GAA GTA TTG AGC GGC GGC CGC AGC GAC GTA TTG CTA CTG GAC GTA ACT CCT CTG TCT TTG
 E   V   L   S   G   G   R   S   D   V   L   L   L   D   V   T   P   L   S   L
1204/401                                          1234/411
GGT ATC GAA ACC ATG GGC GGC GTG ATG ACC AAA CTG ATT CAG AAG AAC ACC ACC ATC CCG
 G   I   E   T   M   G   G   V   M   T   K   L   I   Q   K   N   T   T   I   P
1264/421                                          1294/431
ACC AAA GCG TCG CAA GTG TTC TCT ACC GCC GAA GAC AAC CAA AGC GCA GTA ACC ATC CAC
 T   K   A   S   Q   V   F   S   T   A   E   D   N   Q   S   A   V   T   I   H
1324/441                                          1354/451
GTA CTG CAA GGC GAA CGC GAA CGC GCT TCT GCC AAC AAA TCT TTG GGT CAG TTC AAC TTG
 V   L   Q   G   E   R   E   R   A   S   A   N   K   S   L   G   Q   F   N   L
1384/461                                          1414/471
GGC GAC ATC GCA CCT GCA CCG CGC GGT ATG CCG CAA ATC GAA GTA ACC TTC GAC ATC GAC
 G   D   I   A   P   A   P   R   G   M   P   Q   I   E   V   T   F   D   I   D
1444/481                                          1474/491
GCC AAC GGC ATC CTG CAC GTT TCC GCC AAA GAC AAA GGC ACC GGT AAA GCA GCC AAC ATC
 A   N   G   I   L   H   V   S   A   K   D   K   G   T   G   K   A   A   N   I
1504/501                                          1534/511
ACC ATC CAA GGT TCT TCA GGT TTG AGC GAA GAA GAA ATC GAA CGC ATG GTG AAA GAT GCC
 T   I   Q   G   S   S   G   L   S   E   E   E   I   E   R   M   V   K   D   A
1564/521                                          1594/531
GAA GCC AAT GCC GAG GAA GAT AAA AAA CTG ACT GAA TTG GTC GCT TCC CGC AAC CAA GCC
 E   A   N   A   E   E   D   K   K   L   T   E   L   V   A   S   R   N   Q   A
1624/541                                          1654/551
GAA GCC CTG ATT CAC TCT GTG AAA AAA TCT TTG GCC GAC TAC GGC GAC AAA CTC GAT GCA
 E   A   L   I   H   S   V   K   K   S   L   A   D   Y   G   D   K   L   D   A
1684/561                                          1714/571
GCC GAG AAA GAA AAA ATT GAA GCC GCG CTG AAA GAA GCC GAA GAA GCA GTT AAA GGC GAC
 A   E   K   E   K   I   E   A   A   L   K   E   A   E   E   A   V   K   G   D
1744/581                                          1774/591
GAC AAA GCC GCT ATC GAT GCC AAA ACC GAG GCG CTG GGC GCA GCC AGC CAA AAA CTG GGG
 D   K   A   A   I   D   A   K   T   E   A   L   G   A   A   S   Q   K   L   G
1804/601                                          1834/611
GAA ATG GTT TAC GCT CAA GCA CAA GCT GAA GCC CAA GCA GGC GAA AGC GAA CAA GCC AAT
 E   M   V   Y   A   Q   A   Q   A   E   A   Q   A   G   E   S   E   Q   A   N
1864/621                                          1894/631
GCT TCT GCA AAG AAA GAC GAT GAT GTC GTA GAT GCC GAC TTT GAA GAA GTA AAA GAC GAC
 A   S   A   K   K   D   D   D   V   V   D   A   D   F   E   E   V   K   D   D
1924/641
AAA AAA TAA
 K   K   *
```

FIG. 6B

```
1/1                                        31/11
ATG GCA AAA GTA ATC GGT ATC GAC TTA GGT    ACA ACC AAC TCT TGT TTG GCC ATT TCC GAA
 M   A   K   V   I   G   I   D   L   G      T   T   N   S   C   L   A   I   S   E
61/21                                      91/31
AAC GGT CAA ACC AAA GTG ATC GAA AAC GCA    GAA GGC GCA CGC ACC ACG CCG TCC GTT ATC
 N   G   Q   T   K   V   I   E   N   A      E   G   A   R   T   T   P   S   V   I
121/41                                     151/51
GCT TAT TTG GAC GGC GGC GAA ATC CTC GTC    GGT GCG CCT GCC AAA CGC CAA GCG GTA ACC
 A   Y   L   D   G   G   E   I   L   V      G   A   P   A   K   R   Q   A   V   T
181/61                                     211/71
AAC GCC AAA AAC ACC ATT TAC GCC GCC AAA    CGT TTG ATC GGC CAC AAA TTT GAA GAC AAA
 N   A   K   N   T   I   Y   A   A   K      R   L   I   G   H   K   F   E   D   K
241/81                                     271/91
GAA GTC CAA CGC GAC ATC GAA TCT ATG CCT    TTC GAA ATC ATC AAA GCC AAC AAC GGC GAC
 E   V   Q   R   D   I   E   S   M   P      F   E   I   I   K   A   N   N   G   D
301/101                                    331/111
GCA TGG GTA AAA GCA CAA GGC AAA GAG CTG    TCT CCT CCT CAA ATT TCC GCA GAA GTC CTG
 A   W   V   K   A   Q   G   K   E   L      S   P   P   Q   I   S   A   E   V   L
361/121                                    391/131
CGT AAA ATG AAA GAA GCC GCC GAA GCT TAC    TTG GGC GAA AAA GTA ACC GAA GCC GTG ATT
 R   K   M   K   E   A   A   E   A   Y      L   G   E   K   V   T   E   A   V   I
421/141                                    451/151
ACC GTC CCT GCC TAC TTC AAC GAC AGC CAA    CGT CAA GCC ACC AAA GAC GCA GGC CGT ATC
 T   V   P   A   Y   F   N   D   S   Q      R   Q   A   T   K   D   A   G   R   I
481/161                                    511/171
GCC GGT TTG GAC GTG AAA CGC ATC ATC AAC    GAG CCG ACC GCA GCC GCT TTG GCA TTC GGT
 A   G   L   D   V   K   R   I   I   N      E   P   T   A   A   A   L   A   F   G
541/181                                    571/191
ATG GAC AAA GGC GAC AAC AAA GAC CGC AAA    GTA GCC GTA TAT GAC TTG GGC GGC GGT ACT
 M   D   K   G   D   N   K   D   R   K      V   A   V   Y   D   L   G   G   G   T
601/201                                    631/211
TTC GAT ATT TCC ATC ATC GAA ATC GCC AAC    CTC GAC GGC GAC AAA CAA TTC GAA GTA TTG
 F   D   I   S   I   I   E   I   A   N      L   D   G   D   K   Q   F   E   V   L
661/221                                    691/231
GCA ACC AAC GGC GAT ACC TTC TTG GGC GGT    GAA GAC TTC GAC CAA CGC CTC ATC GAC CAC
 A   T   N   G   D   T   F   L   G   G      E   D   F   D   Q   R   L   I   D   H
721/241                                    751/251
ATC ATC GCC GAG TTC AAA AAA GAA CAA GGC    ATT GAT TTG AAA CAA GAC GTG ATG GCT CTA
 I   I   A   E   F   K   K   E   Q   G      I   D   L   K   Q   D   V   M   A   L
781/261                                    811/271
CAA CGC CTG AAA GAA GCT GCC GAA AAA GCC    AAA ATC GAA TTG TCC AGC GGC CAG CAA ACC
 Q   R   L   K   E   A   A   E   K   A      K   I   E   L   S   S   G   Q   Q   T
841/281                                    871/291
GAA ATT AAC CTG CCG TAC ATC ACC ATG GAC    GCA ACC GGC CCG AAA CAC TTG GCG ATG AAA
 E   I   N   L   P   Y   I   T   M   D      A   T   G   P   K   H   L   A   M   K
901/301                                    931/311
ATT ACC CGC GCC AAA TTC GAA AGC CTG GTT    GAA GAC CTG ATT ACC CGC TCT ATC GAA CCT
 I   T   R   A   K   F   E   S   L   V      E   D   L   I   T   R   S   I   E   P
961/321                                    991/331
TGC AAA ATT GCA TTG AAA GAT GCC GGC TTG    AGC ACC GGC GAC ATC GAC GAC GTA ATC TTG
 C   K   I   A   L   K   D   A   G   L      S   T   G   D   I   D   D   V   I   L
1021/341                                   1051/351
GTC GGC GGG CAG TCC CGT ATG CCG AAA GTA    CAA GAA GCC GTT AAA GCC TTC TTC GGC AAA
 V   G   G   Q   S   R   M   P   K   V      Q   E   A   V   K   A   F   F   G   K
```

FIG. 8A

```
1081/361                                        1111/371
GAA CCG CGC AAA GAC GTG AAC CCT GAC GAA         GCC GTT GCC GTA GGC GCA GCG ATC CAA GGC
 E   P   R   K   D   V   N   P   D   E          A   V   A   V   G   A   A   I   Q   G
1141/381                                        1171/391
GAA GTA TTG AGC GGC GGC CGC AGC GAC GTA         TTG CTA CTG GAC GTA ACT CCT CTG TCT TTG
 E   V   L   S   G   G   R   S   D   V          L   L   L   D   V   T   P   L   S   L
1201/401                                        1231/411
GGT ATC GAA ACC ATG GGC GGC GTG ATG ACC         AAA CTG ATT CAG AAG AAC ACC ACC ATC CCG
 G   I   E   T   M   G   G   V   M   T          K   L   I   Q   K   N   T   T   I   P
1261/421                                        1291/431
ACC AAA GCG TCG CAA GTG TTC TCT ACC GCC         GAA GAC AAC CAA AGC GCA GTA ACC ATC CAC
 T   K   A   S   Q   V   F   S   T   A          E   D   N   Q   S   A   V   T   I   H
1321/441                                        1351/451
GTA CTG CAA GGC GAA CGC GAA CGC GCT TCT         GCC AAC AAA TCT TTG GGT CAG TTC AAC TTG
 V   L   Q   G   E   R   E   R   A   S          A   N   K   S   L   G   Q   F   N   L
1381/461                                        1411/471
GGC GAC ATC GCA CCT GCA CCG CGC GGT ATG         CCG CAA ATC GAA GTA ACC TTC GAC ATC GAC
 G   D   I   A   P   A   P   R   G   M          P   Q   I   E   V   T   F   D   I   D
1441/481                                        1471/491
GCC AAC GGC ATC CTG CAC GTT TCC GCC AAA         GAC AAA GGC ACC GGT AAA GCA GCC AAC ATC
 A   N   G   I   L   H   V   S   A   K          D   K   G   T   G   K   A   A   N   I
1501/501                                        1531/511
ACC ATC CAA GGT TCT TCA GGT TTG AGC GAA         GAA GAA ATC GAA CGC ATG GTG AAA GAT GCC
 T   I   Q   G   S   S   G   L   S   E          E   E   I   E   R   M   V   K   D   A
1561/521                                        1591/531
GAA GCC AAT GCC GAG GAA GAT AAA AAA CTG         ACT GAA TTG GTC GCT TCC CGC AAC CAA GCC
 E   A   N   A   E   E   D   K   K   L          T   E   L   V   A   S   R   N   Q   A
1621/541                                        1651/551
GAA GCC CTG ATT CAC TCT GTG AAA AAA TCT         TTG GCC GAC TAC GGC GAC AAA CTC GAT GCA
 E   A   L   I   H   S   V   K   K   S          L   A   D   Y   G   D   K   L   D   A
1681/561                                        1711/571
GCC GAG AAA GAA AAA ATT GAA GCC GCG CTG         AAA GAA GCC GAA GAA GCA GTT AAA GGC GAC
 A   E   K   E   K   I   E   A   A   L          K   E   A   E   E   A   V   K   G   D
1741/581                                        1771/591
GAC AAA GCC GCT ATC GAT GCC AAA ACC GAG         GCG CTG GGC GCA GCC AGC CAA AAA CTG GGG
 D   K   A   A   I   D   A   K   T   E          A   L   G   A   A   S   Q   K   L   G
1801/601                                        1831/611
GAA ATG GTT TAC GCT CAA GCA CAA GCT GAA         GCC CAA GCA GGC GAA AGC GAA CAA GCC AAT
 E   M   V   Y   A   Q   A   Q   A   E          A   Q   A   G   E   S   E   Q   A   N
1861/621                                        1891/631
GCT TCT GCA AAG AAA GAC GAT GAT GTC GTA         GAT GCC GAC TTT GAA GAA GTA AAA GAC GAC
 A   S   A   K   K   D   D   D   V   V          D   A   D   F   E   E   V   K   D   D
1921/641
AAA AAA TAA
 K   K   *
```

FIG. 8B

```
1/1                                         31/11
atg ggc agc agc cat cat cat cat cat cac    agc agc ggc ctg gtg ccg cgc ggc agc cat
 M   G   S   S   H   H   H   H   H   H      S   S   G   L   V   P   R   G   S   H
61/21                                       91/31
ATG GCA AAA GTA ATC GGT ATC GAC TTA GGT    ACA ACC AAC TCT TGT TTG GCC ATT TCC GAA
 M   A   K   V   I   G   I   D   L   G      T   T   N   S   C   L   A   I   S   E
121/41                                      151/51
AAC GGT CAA ACC AAA GTG ATC GAA AAC GCA    GAA GGC GCA CGC ACC ACG CCG TCC GTT ATC
 N   G   Q   T   K   V   I   E   N   A      E   G   A   R   T   T   P   S   V   I
181/61                                      211/71
GCT TAT TTG GAC GGC GGC GAA ATC CTC GTC    GGT GCG CCT GCC AAA CGC CAA GCG GTA ACC
 A   Y   L   D   G   G   E   I   L   V      G   A   P   A   K   R   Q   A   V   T
241/81                                      271/91
AAC GCC AAA AAC ACC ATT TAC GCC GCC AAA    CGT TTG ATC GGC CAC AAA TTT GAA GAC AAA
 N   A   K   N   T   I   Y   A   A   K      R   L   I   G   H   K   F   E   D   K
301/101                                     331/111
GAA GTC CAA CGC GAC ATC GAA TCT ATG CCT    TTC GAA ATC ATC AAA GCC AAC AAC GGC GAC
 E   V   Q   R   D   I   E   S   M   P      F   E   I   I   K   A   N   N   G   D
361/121                                     391/131
GCA TGG GTA AAA GCA CAA GGC AAA GAG CTG    TCT CCT CCT CAA ATT TCC GCA GAA GTC CTG
 A   W   V   K   A   Q   G   K   E   L      S   P   P   Q   I   S   A   E   V   L
421/141                                     451/151
CGT AAA ATG AAA GAA GCC GCC GAA GCT TAC    TTG GGC GAA AAA GTA ACC GAA GCC GTG ATT
 R   K   M   K   E   A   A   E   A   Y      L   G   E   K   V   T   E   A   V   I
481/161                                     511/171
ACC GTC CCT GCC TAC TTC AAC GAC AGC CAA    CGT CAA GCC ACC AAA GAC GCA GGC CGT ATC
 T   V   P   A   Y   F   N   D   S   Q      R   Q   A   T   K   D   A   G   R   I
541/181                                     571/191
GCC GGT TTG GAC GTG AAA CGC ATC ATC AAC    GAG CCG ACC GCA GCC GCT TTG GCA TTC GGT
 A   G   L   D   V   K   R   I   I   N      E   P   T   A   A   A   L   A   F   G
601/201                                     631/211
ATG GAC AAA GGC GAC AAC AAA GAC CGC AAA    GTA GCC GTA TAT GAC TTG GGC GGC GGT ACT
 M   D   K   G   D   N   K   D   R   K      V   A   V   Y   D   L   G   G   G   T
661/221                                     691/231
TTC GAT ATT TCC ATC ATC GAA ATC GCC AAC    CTC GAC GGC GAC AAA CAA TTC GAA GTA TTG
 F   D   I   S   I   I   E   I   A   N      L   D   G   D   K   Q   F   E   V   L
721/241                                     751/251
GCA ACC AAC GGC GAT ACC TTC TTG GGC GGT    GAA GAC TTC GAC CAA CGC CTC ATC GAC CAC
 A   T   N   G   D   T   F   L   G   G      E   D   F   D   Q   R   L   I   D   H
781/261                                     811/271
ATC ATC GCC GAG TTC AAA AAA GAA CAA GGC    ATT GAT TTG AAA CAA GAC GTG ATG GCT CTA
 I   I   A   E   F   K   K   E   Q   G      I   D   L   K   Q   D   V   M   A   L
841/281                                     871/291
CAA CGC CTG AAA GAA GCT GCC GAA AAA GCC    AAA ATC GAA TTG TCC AGC GGC CAG CAA ACC
 Q   R   L   K   E   A   A   E   K   A      K   I   E   L   S   S   G   Q   Q   T
901/301                                     931/311
GAA ATT AAC CTG CCG TAC ATC ACC ATG GAC    GCA ACC GGC CCG AAA CAC TTG GCG ATG AAA
 E   I   N   L   P   Y   I   T   M   D      A   T   G   P   K   H   L   A   M   K
961/321                                     991/331
ATT ACC CGC GCC AAA TTC GAA AGC CTG GTT    GAA GAC CTG ATT ACC CGC TCT ATC GAA CCT
 I   T   R   A   K   F   E   S   L   V      E   D   L   I   T   R   S   I   E   P
1021/341                                    1051/351
TGC AAA ATT GCA TTG AAA GAT GCC GGC TTG    AGC ACC GGC GAC ATC GAC GAC GTA ATC TTG
 C   K   I   A   L   K   D   A   G   L      S   T   G   D   I   D   D   V   I   L
```

FIG. 9A

```
1081/361                                    1111/371
GTC GGC GGG CAG TCC CGT ATG CCG AAA GTA CAA GAA GCC GTT AAA GCC TTC TTC GGC AAA
 V   G   G   Q   S   R   M   P   K   V   Q   E   A   V   K   A   F   F   G   K
1141/381                                    1171/391
GAA CCG CGC AAA GAC GTG AAC CCT GAC GAA GCC GTT GCC GTA GGC GCA GCG ATC CAA GGC
 E   P   R   K   D   V   N   P   D   E   A   V   A   V   G   A   A   I   Q   G
1201/401                                    1231/411
GAA GTA TTG AGC GGC GGC CGC AGC GAC GTA TTG CTA CTG GAC GTA ACT CCT CTG TCT TTG
 E   V   L   S   G   G   R   S   D   V   L   L   L   D   V   T   P   L   S   L
1261/421                                    1291/431
GGT ATC GAA ACC ATG GGC GGC GTG ATG ACC AAA CTG ATT CAG AAG AAC ACC ACC ATC CCG
 G   I   E   T   M   G   G   V   M   T   K   L   I   Q   K   N   T   T   I   P
1321/441                                    1351/451
ACC AAA GCG TCG CAA GTG TTC TCT ACC GCC GAA GAC AAC CAA AGC GCA GTA ACC ATC CAC
 T   K   A   S   Q   V   F   S   T   A   E   D   N   Q   S   A   V   T   I   H
1381/461                                    1411/471
GTA CTG CAA GGC GAA CGC GAA CGC GCT TCT GCC AAC AAA TCT TTG GGT CAG TTC AAC TTG
 V   L   Q   G   E   R   E   R   A   S   A   N   K   S   L   G   Q   F   N   L
1441/481                                    1471/491
GGC GAC ATC GCA CCT GCA CCG CGC GGT ATG CCG CAA ATC GAA GTA ACC TTC GAC ATC GAC
 G   D   I   A   P   A   P   R   G   M   P   Q   I   E   V   T   F   D   I   D
1501/501                                    1531/511
GCC AAC GGC ATC CTG CAC GTT TCC GCC AAA GAC AAA GGC ACC GGT AAA GCA GCC AAC ATC
 A   N   G   I   L   H   V   S   A   K   D   K   G   T   G   K   A   A   N   I
1561/521                                    1591/531
ACC ATC CAA GGT TCT TCA GGT TTG AGC GAA GAA GAA ATC GAA CGC ATG GTG AAA GAT GCC
 T   I   Q   G   S   S   G   L   S   E   E   E   I   E   R   M   V   K   D   A
1621/541                                    1651/551
GAA GCC AAT GCC GAG GAA GAT AAA AAA CTG ACT GAA TTG GTC GCT TCC CGC AAC CAA GCC
 E   A   N   A   E   E   D   K   K   L   T   E   L   V   A   S   R   N   Q   A
1681/561                                    1711/571
GAA GCC CTG ATT CAC TCT GTG AAA AAA TCT TTG GCC GAC TAC GGC GAC AAA CTC GAT GCA
 E   A   L   I   H   S   V   K   K   S   L   A   D   Y   G   D   K   L   D   A
1741/581                                    1771/591
GCC GAG AAA GAA AAA ATT GAA GCC GCG CTG AAA GAA GCC GAA GAA GCA GTT AAA GGC GAC
 A   E   K   E   K   I   E   A   A   L   K   E   A   E   E   A   V   K   G   D
1801/601                                    1831/611
GAC AAA GCC GCT ATC GAT GCC AAA ACC GAG GCG CTG GGC GCA GCC AGC CAA AAA CTG GGG
 D   K   A   A   I   D   A   K   T   E   A   L   G   A   A   S   Q   K   L   G
1861/621                                    1891/631
GAA ATG GTT TAC GCT CAA GCA CAA GCT GAA GCC CAA GCA GGC GAA AGC GAA CAA GCC AAT
 E   M   V   Y   A   Q   A   Q   A   E   A   Q   A   G   E   S   E   Q   A   N
1921/641                                    1951/651
GCT TCT GCA AAG AAA GAC GAT GAT GTC GTA GAT GCC GAC TTT GAA GAA GTA AAA GAC GAC
 A   S   A   K   K   D   D   D   V   V   D   A   D   F   E   E   V   K   D   D
1981/661
AAA AAA TAA
 K   K   *
```

FIG. 9B

```
1    GTACGAATTT CCCCTTCCGA CGATCCGAGA ACGTCCCTCG GGAAGGCCAC ACGTGACCTT CTAGGAGCTT 70
71   CTCCCGCCAA GACATCCGGG GATCGAGAAT CGCCTGGAAA AATTTCGAGA CTTTGGCTTC ATCTCCCCAG 140
141  CTTTCATCTC CATTCCATCT TCCTTACCTT CTATTCCCCC TCTTCTCTTC CTTCTCTGCA CCTGTTCTTG 210
211  CTCTGGGAGG TTCGATCGGG CAGTAGTGTT CATCTTAACG TTGATTATAT TCTCTTCTAT CCCGTCCTTT 280
281  CATCACCCTT CTTTCCATA 299
```

```
300/1                                       330/11
ATG CAG AGA GCT CTT TCT TCC AGG ACG TCT GTC CTT TCC GCT GCC TCC AAA CGG GCT GCT
 M   Q   R   A   L   S   S   R   T   S   V   L   S   A   A   S   K   R   A   A
360/21                          390/31
TTC ACC AAG CCC GCT GGC CTT AAC CTG CAG CAG CAG CGT TTC GCC CAC AAG
 F   T   K   P   A   G   L   N   L   Q   Q   Q   R   F   A   H   K
```

```
411  GTATGTTTTC ATCTACAATC TAGAATTTTA AGCTTCTGAA GTGGTGCCAA TTTCTCCGTG TCACCCGGAG 480
481  CTCAACCCCG ATACCTTGCT AACGAACTTT CAG 513
```

```
514/38                                      544/48
GAG CTC AAG TTC GGT GTC GAA GCC CGT GCT CAG CTC CTC AAG GGT GTT GAC ACT CTG GCC
 E   L   K   F   G   V   E   A   R   A   Q   L   L   K   G   V   D   T   L   A
574/58                          604/68
AAG GCC GTG ACT TCG ACT CTT GGT CCT AAG GGT CGT AAC GTC CTT ATC GAG TCT CCC TAT
 K   A   V   T   S   T   L   G   P   K   G   R   N   V   L   I   E   S   P   Y
634/78
GGC TCC CCT AAG ATC ACC AAG G
 G   S   P   K   I   T   K   D
```

```
656  GTACG TTTGACTCGA GTTAACCCAA GTCGCTGCTT TCACAAACGA ATTGTGGTTC TGACTAAAAA TAG 723
724/85                                      753/95
  AT GGT GTC TCT GTT GCC AAG GCC ATC ACT CTC CAA GAC AAG TTC GAG AAC CTC GGT GCT
      G   V   S   V   A   K   A   I   T   L   Q   D   K   F   E   N   L   G   A
783/105                                     813/115
CGC CTC CTC CAG GAT GTC GCT TCT AAG ACC AAC GAG ATT GCT GGT GAC GGT ACC ACC ACC
 R   L   L   Q   D   V   A   S   K   T   N   E   I   A   G   D   G   T   T   T
843/125                         873/135
GCT ACC GTC CTT GCC CGT GCC ATC TTC TCT GAG ACC GTG AAG AAT GTT GCT GCT GGC TGC
 A   T   V   L   A   R   A   I   F   S   E   T   V   K   N   V   A   A   G   C
903/145                         933/155
AAC CCC ATG GAT CTG CGC CGC GGT ATC CAG GCT GCT GTT GAT GCT GTC GTC GAC TAC CTC
 N   P   M   D   L   R   R   G   I   Q   A   A   V   D   A   V   V   D   Y   L
963/165                         993/175
CAG AAG AAC AAG CGT GAC ATC ACC ACC GGT GAG GAG ATC GCT CAG GTT GCT ACT ATC TCC
 Q   K   N   K   R   D   I   T   T   G   E   E   I   A   Q   V   A   T   I   S
1023/185                        1053/195
GCT AAC GGT GAC ACC CAC ATT GGT AAG CTG ATC TCC ACC GCC ATG GAG CGT GTT GGC AAG
 A   N   G   D   T   H   I   G   K   L   I   S   T   A   M   E   R   V   G   K
1083/205                        1113/215
GAG GGT GTC ATC ACT GTC AAG GAG GGC AAG ACC ATT GAG GAT GAG CTC GAG GTC ACT GAG
 E   G   V   I   T   V   K   E   G   K   T   I   E   D   E   L   E   V   T   E
1143/225                        1173/235
GGT ATG CGC TTC GAC CGT GGA TAC ACC TCC CCC TAC TTC ATC ACC GAT ACC AAG TCC CAG
 G   M   R   F   D   R   G   Y   T   S   P   Y   F   I   T   D   T   K   S   Q
```

FIG. 14A

```
1203/245                                1233/255
AAG GTT GAG TTC GAG AAG CCT CTG ATT CTG CTG TCT GAG AAG AAG ATC TCT GCC GTT CAG
 K   V   E   F   E   K   P   L   I   L   L   S   E   K   K   I   S   A   V   Q
1263/265                                1293/275
GAC ATC ATC CCC GCC CTT GAG GCC TCC ACC ACC CTC CGC CGC CCC CTG GTT ATT ATC GCA
 D   I   I   P   A   L   E   A   S   T   T   L   R   R   P   L   V   I   I   A
1323/285                                1353/295
GAG GAC ATT GAG GGT GAG GCT CTC GCC GTC TGC ATT CTG AAC AAG CTT CGT GGC CAG CTG
 E   D   I   E   G   E   A   L   A   V   C   I   L   N   K   L   R   G   Q   L
1383/305                                1413/315
CAG GTC GCT GCT GTC AAG GCT CCT GGA TTC GGT GAC AAC CGC AAG AGC ATC CTG GGC GAT
 Q   V   A   A   V   K   A   P   G   F   G   D   N   R   K   S   I   L   G   D
1443/325                                1473/335
CTT GCC GTC CTT ACC AAC GGT ACC GTC TTC ACT GAT GAG CTC GAC ATC AAA CTC GAG AAG
 L   A   V   L   T   N   G   T   V   F   T   D   E   L   D   I   K   L   E   K
1503/345                                1533/355
CTT ACC CCC GAT ATG CTT GGT TCC ACC GGC GCC ATC ACC ATC ACC AAG GAG GAC ACC ATC
 L   T   P   D   M   L   G   S   T   G   A   I   T   I   T   K   E   D   T   I
1563/365                                1593/375
ATC CTG AAC GGG GAG GGC AGC AAG GAC GCC ATT GCC CAG CGC TGC GAG CAG ATT CGC GGT
 I   L   N   G   E   G   S   K   D   A   I   A   Q   R   C   E   Q   I   R   G
1623/385                                1653/395
GTC ATG GCG GAC CCC AGC ACC TCC GAA TAC GAG AAG GAG AAG CTC CAG GAG CGT CTA GCT
 V   M   A   D   P   S   T   S   E   Y   E   K   E   K   L   Q   E   R   L   A
1683/405                                1713/415
AAG CTC TCT GGT GGT GTT GCC GTC ATC AAG GTC GGT GGT GCC TCC GAG GTT GAG GTC GGT
 K   L   S   G   G   V   A   V   I   K   V   G   G   A   S   E   V   E   V   G
1743/425                                1773/435
GAG AAG AAG GAC CGT GTT GTC GAT GCT CTC AAT GCT ACC CGT GCT GCT GTT GAG GAG GGT
 E   K   K   D   R   V   V   D   A   L   N   A   T   R   A   A   V   E   E   G
1803/445                                1833/455
ATC CTC CCC GGT GGT GGT ACC GCC CTT CTC AAG GCC GCC GCC AAC GGC CTT GAC AAT GTC
 I   L   P   G   G   G   T   A   L   L   K   A   A   A   N   G   L   D   N   V
1863/465                                1893/475
AAG CCC GAG AAC TTC GAC CAG CAA CTC GGT GTG AGC ATC ATC AAG AAT GCC ATC ACC CGC
 K   P   E   N   F   D   Q   Q   L   G   V   S   I   I   K   N   A   I   T   R
1923/485                                1953/495
CCC GCT CGC ACC ATT GTT GAG AAC GCC GGC CTC GAG GGC AGC GTC ATT GTC GGC AAG CTG
 P   A   R   T   I   V   E   N   A   G   L   E   G   S   V   I   V   G   K   L
1983/505                                2013/515
ACC GAC GAG TTC GCC AAG GAC TTC AAC CGC GGT TTC GAC AGC TCC AAG GGC GAG TAC GTC
 T   D   E   F   A   K   D   F   N   R   G   F   D   S   S   K   G   E   Y   V
2043/525                                2073/535
GAC ATG ATC TCC AGC GGT ATC CTC GAT CCC CTC AAG GTT GTT CGC ACC GCT CTG CTC GAC
 D   M   I   S   S   G   I   L   D   P   L   K   V   V   R   T   A   L   L   D
2103/545                                2133/555
GCC AGC GGT GTC GCC TCC CTG CTC GGT ACC ACT GAG GTC GCT ATT GTT GAG GCC CCT GAG
 A   S   G   V   A   S   L   L   G   T   T   E   V   A   I   V   E   A   P   E
2163/565                                2193/575
GAG AAG GGC CCC GCT GCT CCT GGC ATG GGT GGT ATG GGT GGT ATG GGC GGC ATG GGT GGC
 E   K   G   P   A   A   P   G   M   G   G   M   G   G   M   G   G   M   G   G
2223/585
GGC ATG TTC TAA    GCTGCT CCCAGTTGCC TTTGCTACCA TAGCCTCTTC CATGATTTAA AGGTTTAACT 2290
 G   M   F   *
2291 TCCCTTTCGA GCGTGTCTTT GCATGTACGA GCATTTCCTG ATATATCGGT GTTGAGAGTT TTCTGTAATT 2360
2361 TTTCCTTTGT TTCTGATGTG TTACACGCCT TGACAGCCCC TTCACCTACT CCGACTTCGT CTTATACCTC 2430
2431 GATACTCATA TCTCCCTCTT CGACCCGCCT CCCCTTTGAT TGACTCGATC 2480
```

FIG. 14B

```
109/1                                          139/11
ATG AAA GAG CTC AAG TTC GGT GTC GAA GCC CGT GCT CAG CTC CTC AAG GGT GTT GAC ACT
 M   K   E   L   K   F   G   V   E   A   R   A   Q   L   L   K   G   V   D   T
169/21                                         199/31
CTG GCC AAG GCC GTG ACT TCG ACT CTT GGT CCT AAG GGT CGT AAC GTC CTT ATC GAG TCT
 L   A   K   A   V   T   S   T   L   G   P   K   G   R   N   V   L   I   E   S
229/41                                         259/51
CCC TAT GGC TCC CCT AAG ATC ACC AAG GAT GGT GTC TCT GTT GCC AAG GCC ATC ACT CTC
 P   Y   G   S   P   K   I   T   K   D   G   V   S   V   A   K   A   I   T   L
289/61                                         319/71
CAA GAC AAG TTC GAG AAC CTC GGT GCT CGC CTC CTC CAG GAT GTC GCT TCT AAG ACC AAC
 Q   D   K   F   E   N   L   G   A   R   L   L   Q   D   V   A   S   K   T   N
349/81                                         379/91
GAG ATT GCT GGT GAC GGT ACC ACC ACC GCT ACC GTC CTT GCC CGT GCC ATC TTC TCT GAG
 E   I   A   G   D   G   T   T   T   A   T   V   L   A   R   A   I   F   S   E
409/101                                        439/111
ACC GTG AAG AAT GTT GCT GCT GGC TGC AAC CCC ATG GAT CTG CGC CGC GGT ATC CAG GCT
 T   V   K   N   V   A   A   G   C   N   P   M   D   L   R   R   G   I   Q   A
469/121                                        499/131
GCT GTT GAT GCT GTC GTC GAC TAC CTC CAG AAG AAC AAG CGT GAC ATC ACC ACC GGT GAG
 A   V   D   A   V   V   D   Y   L   Q   K   N   K   R   D   I   T   T   G   E
529/141                                        559/151
GAG ATC GCT CAG GTT GCT ACT ATC TCC GCT AAC GGT GAC ACC CAC ATT GGT AAG CTG ATC
 E   I   A   Q   V   A   T   I   S   A   N   G   D   T   H   I   G   K   L   I
589/161                                        619/171
TCC ACC GCC ATG GAG CGT GTT GGC AAG GAG GGT GTC ATC ACT GTC AAG GAG GGC AAG ACC
 S   T   A   M   E   R   V   G   K   E   G   V   I   T   V   K   E   G   K   T
649/181                                        679/191
ATT GAG GAT GAG CTC GAG GTC ACT GAG GGT ATG CGC TTC GAC CGT GGA TAC ACC TCC CCC
 I   E   D   E   L   E   V   T   E   G   M   R   F   D   R   G   Y   T   S   P
709/201                                        739/211
TAC TTC ATC ACC GAT ACC AAG TCC CAG AAG GTT GAG TTC GAG AAG CCT CTG ATT CTG CTG
 Y   F   I   T   D   T   K   S   Q   K   V   E   F   E   K   P   L   I   L   L
769/221                                        799/231
TCT GAG AAG AAG ATC TCT GCC GTT CAG GAC ATC ATC CCC GCC CTT GAG GCC TCC ACC ACC
 S   E   K   K   I   S   A   V   Q   D   I   I   P   A   L   E   A   S   T   T
829/241                                        859/251
CTC CGC CGC CCC CTG GTT ATT ATC GCA GAG GAC ATT GAG GGT GAG GCT CTC GCC GTC TGC
 L   R   R   P   L   V   I   I   A   E   D   I   E   G   E   A   L   A   V   C
889/261                                        919/271
ATT CTG AAC AAG CTT CGT GGC CAG CTG CAG GTC GCT GCT GTC AAG GCT CCT GGA TTC GGT
 I   L   N   K   L   R   G   Q   L   Q   V   A   A   V   K   A   P   G   F   G
949/281                                        979/291
GAC AAC CGC AAG AGC ATC CTG GGC GAT CTT GCC GTC CTT ACC AAC GGT ACC GTC TTC ACT
 D   N   R   K   S   I   L   G   D   L   A   V   L   T   N   G   T   V   F   T
1009/301                                       1039/311
GAT GAG CTC GAC ATC AAA CTC GAG AAG CTT ACC CCC GAT ATG CTT GGT TCC ACC GGC GCC
 D   E   L   D   I   K   L   E   K   L   T   P   D   M   L   G   S   T   G   A
1069/321                                       1099/331
ATC ACC ATC ACC AAG GAG GAC ACC ATC ATC CTG AAC GGG GAG GGC AGC AAG GAC GCC ATT
 I   T   I   T   K   E   D   T   I   I   L   N   G   E   G   S   K   D   A   I
```

FIG. 16A

```
1129/341                                           1159/351
GCC CAG CGC TGC GAG CAG ATT CGC GGT GTC ATG GCG GAC CCC AGC ACC TCC GAA TAC GAG
 A   Q   R   C   E   Q   I   R   G   V   M   A   D   P   S   T   S   E   Y   E
1189/361                                           1219/371
AAG GAG AAG CTC CAG GAG CGT CTA GCT AAG CTC TCT GGC GGT GTT GCC GTC ATC AAG GTC
 K   E   K   L   Q   E   R   L   A   K   L   S   G   G   V   A   V   I   K   V
1249/381                                           1279/391
GGT GGT GCC TCC GAG GTT GAG GTC GGT GAG AAG AAG GAC CGT GTT GTC GAT GCT CTC AAT
 G   G   A   S   E   V   E   V   G   E   K   K   D   R   V   V   D   A   L   N
1309/401                                           1339/411
GCT ACC CGT GCT GCT GTT GAG GAG GGT ATC CTC CCC GGT GGT GGT ACC GCC CTT CTC AAG
 A   T   R   A   A   V   E   E   G   I   L   P   G   G   G   T   A   L   L   K
1369/421                                           1399/431
GCC GCC GCC AAC GGC CTT GAC AAT GTC AAG CCC GAG AAC TTC GAC CAG CAA CTC GGT GTG
 A   A   A   N   G   L   D   N   V   K   P   E   N   F   D   Q   Q   L   G   V
1429/441                                           1459/451
AGC ATC ATC AAG AAT GCC ATC ACC CGC CCC GCT CGC ACC ATT GTT GAG AAC GCC GGC CTC
 S   I   I   K   N   A   I   T   R   P   A   R   T   I   V   E   N   A   G   L
1489/461                                           1519/471
GAG GGC AGC GTC ATT GTC GGC AAG CTG ACC GAC GAG TTC GCC AAG GAC TTC AAC CGC GGT
 E   G   S   V   I   V   G   K   L   T   D   E   F   A   K   D   F   N   R   G
1549/481                                           1579/491
TTC GAC AGC TCC AAG GGC GAG TAC GTC GAC ATG ATC TCC AGC GGT ATC CTC GAT CCC CTC
 F   D   S   S   K   G   E   Y   V   D   M   I   S   S   G   I   L   D   P   L
1609/501                                           1639/511
AAG GTT GTT CGC ACC GCT CTG CTC GAC GCC AGC GGT GTC GCC TCC CTG CTC GGT ACC ACT
 K   V   V   R   T   A   L   L   D   A   S   G   V   A   S   L   L   G   T   T
1669/521                                           1699/531
GAG GTC GCT ATT GTT GAG GCC CCT GAG GAG AAG GGC CCC GCT GCT CCT GGC ATG GGT GGT
 E   V   A   I   V   E   A   P   E   E   K   G   P   A   A   P   G   M   G   G
1729/541                                           1759/551
ATG GGT GGT ATG GGC GGC ATG GGC GGC ATG TAG
 M   G   G   M   G   G   M   G   G   M   *
```

FIG. 16B

```
108/1                                    138/11
ATG GGC AGC AGC CAT CAT CAT CAT CAT CAC AGC AGC GGC CTG GTG CCG CGC GGC AGC CAT
 M   G   S   S   H   H   H   H   H   H   S   S   G   L   V   P   R   G   S   H
168/21                                   198/31
ATG AAA GAG CTC AAG TTC GGT GTC GAA GCC CGT GCT CAG CTC CTC AAG GGT GTT GAC ACT
 M   K   E   L   K   F   G   V   E   A   R   A   Q   L   L   K   G   V   D   T
228/41                                   258/51
CTG GCC AAG GCC GTG ACT TCG ACT CTT GGT CCT AAG GGT CGT AAC GTC CTT ATC GAG TCT
 L   A   K   A   V   T   S   T   L   G   P   K   G   R   N   V   L   I   E   S
288/61                                   318/71
CCC TAT GGC TCC CCT AAG ATC ACC AAG GAT GGT GTC TCT GTT GCC AAG GCC ATC ACT CTC
 P   Y   G   S   P   K   I   T   K   D   G   V   S   V   A   K   A   I   T   L
348/81                                   378/91
CAA GAC AAG TTC GAG AAC CTC GGT GCT CGC CTC CTC CAG GAT GTC GCT TCT AAG ACC AAC
 Q   D   K   F   E   N   L   G   A   R   L   L   Q   D   V   A   S   K   T   N
408/101                                  438/111
GAG ATT GCT GGT GAC GGT ACC ACC ACC GCT ACC GTC CTT GCC CGT GCC ATC TTC TCT GAG
 E   I   A   G   D   G   T   T   T   A   T   V   L   A   R   A   I   F   S   E
468/121                                  498/131
ACC GTG AAG AAT GTT GCT GCT GGC TGC AAC CCC ATG GAT CTG CGC CGC GGT ATC CAG GCT
 T   V   K   N   V   A   A   G   C   N   P   M   D   L   R   R   G   I   Q   A
528/141                                  558/151
GCT GTT GAT GCT GTC GTC GAC TAC CTC CAG AAG AAC AAG CGT GAC ATC ACC ACC GGT GAG
 A   V   D   A   V   V   D   Y   L   Q   K   N   K   R   D   I   T   T   G   E
588/161                                  618/171
GAG ATC GCT CAG GTT GCT ACT ATC TCC GCT AAC GGT GAC ACC CAC ATT GGT AAG CTG ATC
 E   I   A   Q   V   A   T   I   S   A   N   G   D   T   H   I   G   K   L   I
648/181                                  678/191
TCC ACC GCC ATG GAG CGT GTT GGC AAG GAG GGT GTC ATC ACT GTC AAG GAG GGC AAG ACC
 S   T   A   M   E   R   V   G   K   E   G   V   I   T   V   K   E   G   K   T
708/201                                  738/211
ATT GAG GAT GAG CTC GAG GTC ACT GAG GGT ATG CGC TTC GAC CGT GGA TAC ACC TCC CCC
 I   E   D   E   L   E   V   T   E   G   M   R   F   D   R   G   Y   T   S   P
768/221                                  798/231
TAC TTC ATC ACC GAT ACC AAG TCC CAG AAG GTT GAG TTC GAG AAG CCT CTG ATT CTG CTG
 Y   F   I   T   D   T   K   S   Q   K   V   E   F   E   K   P   L   I   L   L
828/241                                  858/251
TCT GAG AAG AAG ATC TCT GCC GTT CAG GAC ATC ATC CCC GCC CTT GAG GCC TCC ACC ACC
 S   E   K   K   I   S   A   V   Q   D   I   I   P   A   L   E   A   S   T   T
888/261                                  918/271
CTC CGC CGC CCC CTG GTT ATT ATC GCA GAG GAC ATT GAG GGT GAG GCT CTC GCC GTC TGC
 L   R   R   P   L   V   I   I   A   E   D   I   E   G   E   A   L   A   V   C
948/281                                  978/291
ATT CTG AAC AAG CTT CGT GGC CAG CTG CAG GTC GCT GCT GTC AAG GCT CCT GGA TTC GGT
 I   L   N   K   L   R   G   Q   L   Q   V   A   A   V   K   A   P   G   F   G
1008/301                                 1038/311
GAC AAC CGC AAG AGC ATC CTG GGC GAT CTT GCC GTC CTT ACC AAC GGT ACC GTC TTC ACT
 D   N   R   K   S   I   L   G   D   L   A   V   L   T   N   G   T   V   F   T
```

FIG. 18A

```
1068/321                                        1098/331
GAT GAG CTC GAC ATC AAA CTC GAG AAG CTT ACC CCC GAT ATG CTT GGT TCC ACC GGC GCC
 D   E   L   D   I   K   L   E   K   L   T   P   D   M   L   G   S   T   G   A
1128/341                                        1158/351
ATC ACC ATC ACC AAG GAG GAC ACC ATC ATC CTG AAC GGG GAG GGC AGC AAG GAC GCC ATT
 I   T   I   T   K   E   D   T   I   I   L   N   G   E   G   S   K   D   A   I
1188/361                                        1218/371
GCC CAG CGC TGC GAG CAG ATT CGC GGT GTC ATG GCG GAC CCC AGC ACC TCC GAA TAC GAG
 A   Q   R   C   E   Q   I   R   G   V   M   A   D   P   S   T   S   E   Y   E
1248/381                                        1278/391
AAG GAG AAG CTC CAG GAG CGT CTA GCT AAG CTC TCT GGC GGT GTT GCC GTC ATC AAG GTC
 K   E   K   L   Q   E   R   L   A   K   L   S   G   G   V   A   V   I   K   V
1308/401                                        1338/411
GGT GGT GCC TCC GAG GTT GAG GTC GGT GAG AAG AAG GAC CGT GTT GTC GAT GCT CTC AAT
 G   G   A   S   E   V   E   V   G   E   K   K   D   R   V   V   D   A   L   N
1368/421                                        1398/431
GCT ACC CGT GCT GCT GTT GAG GAG GGT ATC CTC CCC GGT GGT GGT ACC GCC CTT CTC AAG
 A   T   R   A   A   V   E   E   G   I   L   P   G   G   G   T   A   L   L   K
1428/441                                        1458/451
GCC GCC GCC AAC GGC CTT GAC AAT GTC AAG CCC GAG AAC TTC GAC CAG CAA CTC GGT GTG
 A   A   A   N   G   L   D   N   V   K   P   E   N   F   D   Q   Q   L   G   V
1488/461                                        1518/471
AGC ATC ATC AAG AAT GCC ATC ACC CGC CCC GCT CGC ACC ATT GTT GAG AAC GCC GGC CTC
 S   I   I   K   N   A   I   T   R   P   A   R   T   I   V   E   N   A   G   L
1548/481                                        1578/491
GAG GGC AGC GTC ATT GTC GGC AAG CTG ACC GAC GAG TTC GCC AAG GAC TTC AAC CGC GGT
 E   G   S   V   I   V   G   K   L   T   D   E   F   A   K   D   F   N   R   G
1608/501                                        1638/511
TTC GAC AGC TCC AAG GGC GAG TAC GTC GAC ATG ATC TCC AGC GGT ATC CTC GAT CCC CTC
 F   D   S   S   K   G   E   Y   V   D   M   I   S   S   G   I   L   D   P   L
1668/521                                        1698/531
AAG GTT GTT CGC ACC GCT CTG CTC GAC GCC AGC GGT GTC GCC TCC CTG CTC GGT ACC ACT
 K   V   V   R   T   A   L   L   D   A   S   G   V   A   S   L   L   G   T   T
1728/541                                        1758/551
GAG GTC GCT ATT GTT GAG GCC CCT GAG GAG AAG GGC CCC GCT GCT CCT GGC ATG GGT GGT
 E   V   A   I   V   E   A   P   E   E   K   G   P   A   A   P   G   M   G   G
1788/561                                        1818/571
ATG GGT GGT ATG GGC GGC ATG GGC GGC ATG TAG
 M   G   G   M   G   G   M   G   G   M   *
```

FIG. 18B

```
  1 CCGGGTAAAG TACCTGATTG CGCACTTACA GCTAACAGCT GACGCACTCG AGAAATCTGC CCGTTTTGTT  70

71 CATGGAAACT TGAAGAAAAT CAGGGAAATC GTTACTGCGC TCTCTCTAAC GCTTGCAAGC TCCTGGAATA 140

141 CAAATTCGCA AAGTATATAA CTCTATAGCT TTCAACCTTG TTACTGTGGA GTAGCTGTTA AGGGATAGAG 210

211 ACATAAGATA AACCATACCA TACATAAATC ACCCCCCATA TAAACAA 257
```

```
258/1                                           288/11
ATG TTG AGA GCT GTT GCA CGT TCG CAG GTT AGA TCT TTG AGA AAC GCT CGT TTG TAC TCC
 M   L   R   A   V   A   R   S   Q   V   R   S   L   R   N   A   R   L   Y   S
318/21                                          348/31
AGT TTC AAG GAG TTG AAG TTC GGT GTC GAA GGC AGA GCT GCT CTG CTT CGT GGT GTC GAG
 S   F   K   E   L   K   F   G   V   E   G   R   A   A   L   L   R   G   V   E
378/41                                          408/51
ACT TTG GCC GAC GCT GTC TCT GCC ACG CTG GGG CCT AAG GGT AGA AAT GTG CTG ATC GAG
 T   L   A   D   A   V   S   A   T   L   G   P   K   G   R   N   V   L   I   E
438/61                                          468/71
CAG CCA TTC GGA GCA CCA AAG ATC ACC AAG GAT GGT GTC ACC GTG GCC AGA TCC ATT ACT
 Q   P   F   G   A   P   K   I   T   K   D   G   V   T   V   A   R   S   I   T
498/81                                          528/91
TTG GAG GAC AAG TTC GAG AAC ATG GGT GCT AAG CTT CTG CAA GAA GTT GCC TCC AAG ACT
 L   E   D   K   F   E   N   M   G   A   K   L   L   Q   E   V   A   S   K   T
558/101                                         588/111
AAC GAG GCC GCC GGT GAC GGT ACC ACC TCC GCC ACT GTC TTG GGT AGA GCC ATC TTC ACC
 N   E   A   A   G   D   G   T   T   S   A   T   V   L   G   R   A   I   F   T
618/121                                         648/131
GAG TCC GTC AAG AAC GTC GCT GCC GGT TGC AAC CCT ATG GAT TTG AGA AGG GGT TCC CAG
 E   S   V   K   N   V   A   A   G   C   N   P   M   D   L   R   R   G   S   Q
678/141                                         708/151
GCC GCC GTC GAG AAG GTC ATC CAA TTC TTG ACT GAA AAC AAG AAG GAG ATC ACC ACT TCT
 A   A   V   E   K   V   I   Q   F   L   T   E   N   K   K   E   I   T   T   S
738/161                                         768/171
GAG GAA ATC GCC CAG GTG GCC ACC ATC TCA GCT AAC GGT GAC GCT CAC GTC GGT AAG TTG
 E   E   I   A   Q   V   A   T   I   S   A   N   G   D   A   H   V   G   K   L
798/181                                         828/191
CTT GCC TCC GCC ATG GAA AAG GTT GGC AAG GAA GGT GTT ATC ACC ATC AGA GAA GGC AGA
 L   A   S   A   M   E   K   V   G   K   E   G   V   I   T   I   R   E   G   R
858/201                                         888/211
ACT TTG GAA GAC GAA CTA GAA GTC ACC GAA GGT ATG AGA TTT GAC CGT GGT TTC ATC TCC
 T   L   E   D   E   L   E   V   T   E   G   M   R   F   D   R   G   F   I   S
918/221                                         948/231
CCA TAC TTC ATC ACT GAC GCA AAG TCC GGC AAG GTA GAA TTC GAA AAG CCA TTG TTG TTG
 P   Y   F   I   T   D   A   K   S   G   K   V   E   F   E   K   P   L   L   L
978/241                                         1008/251
TTG AGC GAA AAG AAG ATC TCT TCC ATC CAA GAC ATC TTG CCA GCT TTG GAA CTA TCT AAC
 L   S   E   K   K   I   S   S   I   Q   D   I   L   P   A   L   E   L   S   N
1038/261                                        1068/271
CAA AGT AGA AGA CCA CTA TTG ATC ATC GCC GAA GAT GTC GAC GGT GAA GCC CTA GCT GCT
 Q   S   R   R   P   L   L   I   I   A   E   D   V   D   G   E   A   L   A   A
```

FIG. 21A

```
1098/281                                      1128/291
TGT ATC CTA AAC AAG TTG AGA GGC CAA GTC  AAG GTC TGT GCC GTT AAG GCT CCA GGT TTC
 C   I   L   N   K   L   R   G   Q   V    K   V   C   A   V   K   A   P   G   F
1158/301                                      1188/311
GGT GAC AAC AGA AAG AAC ATT CTA GGT GAT  GTC GCC ATC TTG ACC GGC AGT ACT GTT TTT
 G   D   N   R   K   N   I   L   G   D    V   A   I   L   T   G   S   T   V   F
1218/321                                      1248/331
ACT GAA GAA TTG GAC TTG AAG CCA GAA CAA  GCC ACT ATG GAA CAC CTA GGT TCC TGT GAC
 T   E   E   L   D   L   K   P   E   Q    A   T   M   E   H   L   G   S   C   D
1278/341                                      1308/351
TCC ATT ACT ATC ACA AAG GAA GAC ACT GTT  ATC CTA AAC GGT AAC GGC TCC AAG GAC TCT
 S   I   T   I   T   K   E   D   T   V    I   L   N   G   N   G   S   K   D   S
1338/361                                      1368/371
ATC CAA GAA AGA ATT GAA CAG ATC AAG AAC  TCC ATT GAT GTC ACC ACT ACT AAC TCT TAC
 I   Q   E   R   I   E   Q   I   K   N    S   I   D   V   T   T   T   N   S   Y
1398/381                                      1428/391
GAG AAG GAG AAG CTA CAA GAA AGA CTT GCC  AAG TTA TCC GGT GGT GTT GCT GTC ATC AGG
 E   K   E   K   L   Q   E   R   L   A    K   L   S   G   G   V   A   V   I   R
1458/401                                      1488/411
GTT GGT GGT GCT TCT GAA GTT GAA GTC GGT  GAA AAG AAG GAC CGT TAC GAT GAC GCT TTG
 V   G   G   A   S   E   V   E   V   G    E   K   K   D   R   Y   D   D   A   L
1518/421                                      1548/431
AAT GCC ACC AGA GCT GCC GTT GAA GAA GGT  ATC TTA CCA GGT GGT GGT ACT GCT TTG GTT
 N   A   T   R   A   A   V   E   E   G    I   L   P   G   G   G   T   A   L   V
1578/441                                      1608/451
AAG GCC TCT AGA GTT TTA GAC GAA GTC AAG  ACT GAG AAC TTC GAC CAA AAA TTG GGA GTT
 K   A   S   R   V   L   D   E   V   K    T   E   N   F   D   Q   K   L   G   V
1638/461                                      1668/471
GAC ATT ATC AGA AAG GCC ATT ACT AGA CCA  GCT AAG CAA ATT ATT GAG AAC GCC GGT GAA
 D   I   I   R   K   A   I   T   R   P    A   K   Q   I   I   E   N   A   G   E
1698/481                                      1728/491
GAA GGC TCC GTT ATT GTC GGT AAG CTT GTT  GAT GAA TTT GGC GAA GAT TTT GCT AAG GGT
 E   G   S   V   I   V   G   K   L   V    D   E   F   G   E   D   F   A   K   G
1758/501                                      1788/511
TAC GAC TCC GCT AAG GGA GAA TTC ACT GAT  ATG TTG GCT GCC GGT ATT ATT GAC CCA TTC
 Y   D   S   A   K   G   E   F   T   D    M   L   A   A   G   I   I   D   P   F
1818/521                                      1848/531
AAA GTC GTT AGA TCT GGT CTG GTC GAC GCT  TCC GGT GTT GCT TCC TTG TTG GCT ACT ACC
 K   V   V   R   S   G   L   V   D   A    S   G   V   A   S   L   L   A   T   T
1878/541                                      1908/551
GAA GTT GCC ATC GTT GAC GCT CCT GAA CCA  GCT CCA GCT GCT GGT GCC CCA GGT GGT GGT
 E   V   A   I   V   D   A   P   E   P    A   P   A   A   G   A   P   G   G   G
1938/561                                      1968
ATG CCA GGT ATG CCA GGT ATG ATG TAA AAG  GTC TAA CTT TTG CAA TCA TGC TGG TGA AAA
 M   P   G   M   P   G   M   M   *
1998                                          2028
TGA AGC AAA TCA TTA CAT AGA GTG GTA AAA  TCT TCA AGA CCA AAT AGC TTG TAC
```

FIG. 21B

```
109/1                                         139/11
ATG GCC AAG GAG TTG AAG TTT GGG GTC GAA GGC AGA GCT GCT CTG CTT CGT GGT GTC GAG
 M   A   K   E   L   K   F   G   V   E   G   R   A   A   L   L   R   G   V   E
169/21                                        199/31
ACT TTG GCC GAC GCT GTC TCT GCC ACG CTG GGG CCT AAG GGT AGA AAT GTG CTG ATC GAG
 T   L   A   D   A   V   S   A   T   L   G   P   K   G   R   N   V   L   I   E
229/41                                        259/51
CAG CCA TTC GGA GCA CCA AAG ATC ACC AAG GAT GGT GTC ACC GTG GCC AGA TCC ATT ACT
 Q   P   F   G   A   P   K   I   T   K   D   G   V   T   V   A   R   S   I   T
289/61                                        319/71
TTG GAG GAC AAG TTC GAG AAC ATG GGT GCT AAG CTT CTG CAA GAA GTT GCC TCC AAG ACT
 L   E   D   K   F   E   N   M   G   A   K   L   L   Q   E   V   A   S   K   T
349/81                                        379/91
AAC GAG GCC GCC GGT GAC GGT ACC ACC TCC GCC ACT GTC TTG GGT AGA GCC ATC TTC ACC
 N   E   A   A   G   D   G   T   T   S   A   T   V   L   G   R   A   I   F   T
409/101                                       439/111
GAG TCC GTC AAG AAC GTC GCT GCC GGT TGC AAC CCT ATG GAT TTG AGA AGG GGT TCC CAG
 E   S   V   K   N   V   A   A   G   C   N   P   M   D   L   R   R   G   S   Q
469/121                                       499/131
GCC GCC GTC GAG AAG GTC ATC CAA TTC TTG ACT GAA AAC AAG AAG GAG ATC ACC ACT TCT
 A   A   V   E   K   V   I   Q   F   L   T   E   N   K   K   E   I   T   T   S
529/141                                       559/151
GAG GAA ATC GCC CAG GTG GCC ACC ATC TCA GCT AAC GGT GAC GCT CAC GTC GGT AAG TTG
 E   E   I   A   Q   V   A   T   I   S   A   N   G   D   A   H   V   G   K   L
589/161                                       619/171
CTT GCC TCC GCC ATG GAA AAG GTT GGC AAG GAA GGT GTT ATC ACC ATC AGA GAA GGC AGA
 L   A   S   A   M   E   K   V   G   K   E   G   V   I   T   I   R   E   G   R
649/181                                       679/191
ACT TTG GAA GAC GAA CTA GAA GTC ACC GAA GGT ATG AGA TTT GAC CGT GGT TTC ATC TCC
 T   L   E   D   E   L   E   V   T   E   G   M   R   F   D   R   G   F   I   S
709/201                                       739/211
CCA TAC TTC ATC ACT GAC GCA AAG TCC GGC AAG GTA GAA TTC GAA AAG CCA TTG TTG TTG
 P   Y   F   I   T   D   A   K   S   G   K   V   E   F   E   K   P   L   L   L
769/221                                       799/231
TTG AGC GAA AAG AAG ATC TCT TCC ATC CAA GAC ATC TTG CCA GCT TTG GAA CTA TCT AAC
 L   S   E   K   K   I   S   S   I   Q   D   I   L   P   A   L   E   L   S   N
829/241                                       859/251
CAA AGT AGA AGA CCA CTA TTG ATC ATC GCC GAA GAT GTC GAC GGT GAA GCC CTA GCT GCT
 Q   S   R   R   P   L   L   I   I   A   E   D   V   D   G   E   A   L   A   A
889/261                                       919/271
TGT ATC CTA AAC AAG TTG AGA GGC CAA GTC AAG GTC TGT GCC GTT AAG GCT CCA GGT TTC
 C   I   L   N   K   L   R   G   Q   V   K   V   C   A   V   K   A   P   G   F
949/281                                       979/291
GGT GAC AAC AGA AAG AAC ATT CTA GGT GAT GTC GCC ATC TTG ACC GGC AGT ACT GTT TTT
 G   D   N   R   K   N   I   L   G   D   V   A   I   L   T   G   S   T   V   F
1009/301                                      1039/311
ACT GAA GAA TTG GAC TTG AAG CCA GAA CAA GCC ACT ATG GAA CAC CTA GGT TCC TGT GAC
 T   E   E   L   D   L   K   P   E   Q   A   T   M   E   H   L   G   S   C   D
```

FIG. 23A

```
1069/321                                        1099/331
TCC ATT ACT ATC ACA AAG GAA GAC ACT GTT ATC CTA AAC GGT AAC GGC TCC AAG GAC TCT
 S   I   T   I   T   K   E   D   T   V   I   L   N   G   N   G   S   K   D   S
1129/341                                        1159/351
ATC CAA GAA AGA ATT GAA CAG ATC AAG AAC TCC ATT GAT GTC ACC ACT ACT AAC TCT TAC
 I   Q   E   R   I   E   Q   I   K   N   S   I   D   V   T   T   T   N   S   Y
1189/361                                        1219/371
GAG AAG GAG AAG CTA CAA GAA AGA CTT GCC AAG TTA TCC GGT GGT GTT GCT GTC ATC AGG
 E   K   E   K   L   Q   E   R   L   A   K   L   S   G   G   V   A   V   I   R
1249/381                                        1279/391
GTT GGT GGT GCT TCT GAA GTT GAA GTC GGT GAA AAG AAG GAC CGT TAC GAT GAC GCT TTG
 V   G   G   A   S   E   V   E   V   G   E   K   K   D   R   Y   D   D   A   L
1309/401                                        1339/411
AAT GCC ACC AGA GCT GCC GTT GAA GAA GGT ATC TTA CCA GGT GGT GGT ACT GCT TTG GTT
 N   A   T   R   A   A   V   E   E   G   I   L   P   G   G   G   T   A   L   V
1369/421                                        1399/431
AAG GCC TCT AGA GTT TTA GAC GAA GTC AAG ACT GAG AAC TTC GAC CAA AAA TTG GGA GTT
 K   A   S   R   V   L   D   E   V   K   T   E   N   F   D   Q   K   L   G   V
1429/441                                        1459/451
GAC ATT ATC AGA AAG GCC ATT ACT AGA CCA GCT AAG CAA ATT ATT GAG AAC GCC GGT GAA
 D   I   I   R   K   A   I   T   R   P   A   K   Q   I   I   E   N   A   G   E
1489/461                                        1519/471
GAA GGC TCC GTT ATT GTC GGT AAG CTT GTT GAT GAA TTT GGC GAA GAT TTT GCT AAG GGT
 E   G   S   V   I   V   G   K   L   V   D   E   F   G   E   D   F   A   K   G
1549/481                                        1579/491
TAC GAC TCC GCT AAG GGA GAA TTC ACT GAT ATG TTG GCT GCC GGT ATT ATT GAC CCA TTC
 Y   D   S   A   K   G   E   F   T   D   M   L   A   A   G   I   I   D   P   F
1609/501                                        1639/511
AAA GTC GTT AGA TCT GGT CTG GTC GAC GCT TCC GGT GTT GCT TCC TTG TTG GCT ACT ACC
 K   V   V   R   S   G   L   V   D   A   S   G   V   A   S   L   L   A   T   T
1669/521                                        1699/531
GAA GTT GCC ATC GTT GAC GCT CCT GAA CCA GCT CCA GCT GCT GGT GCC CCA GGT GGT GGT
 E   V   A   I   V   D   A   P   E   P   A   P   A   A   G   A   P   G   G   G
1729/541
ATG CCA GGT ATG CCA GGT ATG ATG TAA
 M   P   G   M   P   G   M   M   *
```

FIG. 23B

```
108/1                                           138/11
ATG GGC AGC AGC CAT CAT CAT CAT CAT CAC AGC AGC GGC CTG GTG CCG CGC GGC AGC CAT
 M   G   S   S   H   H   H   H   H   H   S   S   G   L   V   P   R   G   S   H
168/21                                          198/31
ATG GCC AAG GAG TTG AAG TTT GGG GTC GAA GGC AGA GCT GCT CTG CTT CGT GGT GTC GAG
 M   A   K   E   L   K   F   G   V   E   G   R   A   A   L   L   R   G   V   E
228/41                                          258/51
ACT TTG GCC GAC GCT GTC TCT GCC ACG CTG GGG CCT AAG GGT AGA AAT GTG CTG ATC GAG
 T   L   A   D   A   V   S   A   T   L   G   P   K   G   R   N   V   L   I   E
288/61                                          318/71
CAG CCA TTC GGA GCA CCA AAG ATC ACC AAG GAT GGT GTC ACC GTG GCC AGA TCC ATT ACT
 Q   P   F   G   A   P   K   I   T   K   D   G   V   T   V   A   R   S   I   T
348/81                                          378/91
TTG GAG GAC AAG TTC GAG AAC ATG GGT GCT AAG CTT CTG CAA GAA GTT GCC TCC AAG ACT
 L   E   D   K   F   E   N   M   G   A   K   L   L   Q   E   V   A   S   K   T
408/101                                         438/111
AAC GAG GCC GCC GGT GAC GGT ACC ACC TCC GCC ACT GTC TTG GGT AGA GCC ATC TTC ACC
 N   E   A   A   G   D   G   T   T   S   A   T   V   L   G   R   A   I   F   T
468/121                                         498/131
GAG TCC GTC AAG AAC GTC GCT GCC GGT TGC AAC CCT ATG GAT TTG AGA AGG GGT TCC CAG
 E   S   V   K   N   V   A   A   G   C   N   P   M   D   L   R   R   G   S   Q
528/141                                         558/151
GCC GCC GTC GAG AAG GTC ATC CAA TTC TTG ACT GAA AAC AAG AAG GAG ATC ACC ACT TCT
 A   A   V   E   K   V   I   Q   F   L   T   E   N   K   K   E   I   T   T   S
588/161                                         618/171
GAG GAA ATC GCC CAG GTG GCC ACC ATC TCA GCT AAC GGT GAC GCT CAC GTC GGT AAG TTG
 E   E   I   A   Q   V   A   T   I   S   A   N   G   D   A   H   V   G   K   L
648/181                                         678/191
CTT GCC TCC GCC ATG GAA AAG GTT GGC AAG GAA GGT GTT ATC ACC ATC AGA GAA GGC AGA
 L   A   S   A   M   E   K   V   G   K   E   G   V   I   T   I   R   E   G   R
708/201                                         738/211
ACT TTG GAA GAC GAA CTA GAA GTC ACC GAA GGT ATG AGA TTT GAC CGT GGT TTC ATC TCC
 T   L   E   D   E   L   E   V   T   E   G   M   R   F   D   R   G   F   I   S
768/221                                         798/231
CCA TAC TTC ATC ACT GAC GCA AAG TCC GGC AAG GTA GAA TTC GAA AAG CCA TTG TTG TTG
 P   Y   F   I   T   D   A   K   S   G   K   V   E   F   E   K   P   L   L   L
828/241                                         858/251
TTG AGC GAA AAG AAG ATC TCT TCC ATC CAA GAC ATC TTG CCA GCT TTG GAA CTA TCT AAC
 L   S   E   K   K   I   S   S   I   Q   D   I   L   P   A   L   E   L   S   N
888/261                                         918/271
CAA AGT AGA AGA CCA CTA TTG ATC ATC GCC GAA GAT GTC GAC GGT GAA GCC CTA GCT GCT
 Q   S   R   R   P   L   L   I   I   A   E   D   V   D   G   E   A   L   A   A
948/281                                         978/291
TGT ATC CTA AAC AAG TTG AGA GGC CAA GTC AAG GTC TGT GCC GTT AAG GCT CCA GGT TTC
 C   I   L   N   K   L   R   G   Q   V   K   V   C   A   V   K   A   P   G   F
1008/301                                        1038/311
GGT GAC AAC AGA AAG AAC ATT CTA GGT GAT GTC GCC ATC TTG ACC GGC AGT ACT GTT TTT
 G   D   N   R   K   N   I   L   G   D   V   A   I   L   T   G   S   T   V   F
```

FIG. 25A

```
1068/321                             1098/331
ACT GAA GAA TTG GAC TTG AAG CCA GAA CAA GCC ACT ATG GAA CAC CTA GGT TCC TGT GAC
 T   E   E   L   D   L   K   P   E   Q   A   T   M   E   H   L   G   S   C   D
1128/341                             1158/351
TCC ATT ACT ATC ACA AAG GAA GAC ACT GTT ATC CTA AAC GGT AAC GGC TCC AAG GAC TCT
 S   I   T   I   T   K   E   D   T   V   I   L   N   G   N   G   S   K   D   S
1188/361                             1218/371
ATC CAA GAA AGA ATT GAA CAG ATC AAG AAC TCC ATT GAT GTC ACC ACT ACT AAC TCT TAC
 I   Q   E   R   I   E   Q   I   K   N   S   I   D   V   T   T   T   N   S   Y
1248/381                             1278/391
GAG AAG GAG AAG CTA CAA GAA AGA CTT GCC AAG TTA TCC GGT GGT GTT GCT GTC ATC AGG
 E   K   E   K   L   Q   E   R   L   A   K   L   S   G   G   V   A   V   I   R
1308/401                             1338/411
GTT GGT GGT GCT TCT GAA GTT GAA GTC GGT GAA AAG AAG GAC CGT TAC GAT GAC GCT TTG
 V   G   G   A   S   E   V   E   V   G   E   K   K   D   R   Y   D   D   A   L
1368/421                             1398/431
AAT GCC ACC AGA GCT GCC GTT GAA GAA GGT ATC TTA CCA GGT GGT GGT ACT GCT TTG GTT
 N   A   T   R   A   A   V   E   E   G   I   L   P   G   G   G   T   A   L   V
1428/441                             1458/451
AAG GCC TCT AGA GTT TTA GAC GAA GTC AAG ACT GAG AAC TTC GAC CAA AAA TTG GGA GTT
 K   A   S   R   V   L   D   E   V   K   T   E   N   F   D   Q   K   L   G   V
1488/461                             1518/471
GAC ATT ATC AGA AAG GCC ATT ACT AGA CCA GCT AAG CAA ATT ATT GAG AAC GCC GGT GAA
 D   I   I   R   K   A   I   T   R   P   A   K   Q   I   I   E   N   A   G   E
1548/481                             1578/491
GAA GGC TCC GTT ATT GTC GGT AAG CTT GTT GAT GAA TTT GGC GAA GAT TTT GCT AAG GGT
 E   G   S   V   I   V   G   K   L   V   D   E   F   G   E   D   F   A   K   G
1608/501                             1638/511
TAC GAC TCC GCT AAG GGA GAA TTC ACT GAT ATG TTG GCT GCC GGT ATT ATT GAC CCA TTC
 Y   D   S   A   K   G   E   F   T   D   M   L   A   A   G   I   I   D   P   F
1668/521                             1698/531
AAA GTC GTT AGA TCT GGT CTG GTC GAC GCT TCC GGT GTT GCT TCC TTG TTG GCT ACT ACC
 K   V   V   R   S   G   L   V   D   A   S   G   V   A   S   L   L   A   T   T
1728/541                             1758/551
GAA GTT GCC ATC GTT GAC GCT CCT GAA CCA GCT CCA GCT GCT GGT GCC CCA GGT GGT GGT
 E   V   A   I   V   D   A   P   E   P   A   P   A   A   G   A   P   G   G   G
1788/561
ATG CCA GGT ATG CCA GGT ATG ATG TAA
 M   P   G   M   P   G   M   M   *
```

FIG. 25B

SEQUENCE LISTING

<160> NUMBER OF SEQ ID NOS: 102

<210> SEQ ID NO 1
<211> LENGTH: 2465
<212> TYPE: DNA
<213> ORGANISM: Nesseria meningitidis

<400> SEQUENCE: 1

| | | | | | |
|---|---|---|---|---|---|
| caattcaaca | tactgaacgc | caaagatatg | gatgcagaac | aagtctccct | ttccaaagaa | 60 |
| tgcgacatca | tcgagtcttc | acacgactgg | gaaaaagagt | acggcaactt | gaacgaacag | 120 |
| gaaatgctcg | ccggcatcgt | ctatgaataa | acctgcctgc | catttgaaac | attatgcttg | 180 |
| aatgcattgg | agccaaatgt | attaaatcaa | atataaaacc | aatatattca | taaagttata | 240 |
| tacttatagc | catgctgtag | cttgaaacag | ttccaacata | cccgccgccc | gcccttattta | 300 |
| cagcccatcg | ggacaaaatg | tttctcaaaa | taagcaaaat | caaataggat | tatccacatg | 360 |
| gcaaaagtaa | tcggtatcga | cttaggtaca | accaactctt | gtttggccat | ttccgaaaac | 420 |
| ggtcaaacca | aagtgatcga | aaacgcagaa | ggcgcacgca | ccacgccgtc | cgttatcgct | 480 |
| tatttggacg | gcggcgaaat | cctcgtcggt | gcgcctgcca | aacgccaagc | ggtaaccaac | 540 |
| gccaaaaaca | ccatttacgc | cgccaaacgt | ttgatcggcc | acaaatttga | agacaaagaa | 600 |
| gtccaacgcg | acatcgaatc | tatgcctttc | gaaatcatca | aagccaacaa | cggcgacgca | 660 |
| tgggtaaaag | cacaaggcaa | agagctgtct | cctcctcaaa | tttccgcaga | agtcctgcgt | 720 |
| aaaatgaaag | aagccgccga | agcttacttg | ggcgaaaaag | taaccgaagc | cgtgattacc | 780 |
| gtccctgcct | acttcaacga | cagccaacgt | caagccacca | agacgcagg | ccgtatcgcc | 840 |
| ggtttggacg | tgaaacgcat | catcaacgag | ccgaccgcag | ccgctttggc | attcggtatg | 900 |
| gacaaaggcg | acaacaaaga | ccgcaaagta | gccgtatatg | acttgggcgg | cggtacttc | 960 |
| gatatttcca | tcatcgaaat | cgccaacctc | gacggcgaca | acaattcga | agtattggca | 1020 |
| accaacggcg | ataccttctt | gggcggtgaa | gacttcgacc | aacgcctcat | cgaccacatc | 1080 |
| atcgccgagt | tcaaaaaaga | acaaggcatt | gatttgaaac | aagacgtgat | ggctctacaa | 1140 |
| cgcctgaaag | aagctgccga | aaaagccaaa | atcgaattgt | ccagcggcca | gcaaaccgaa | 1200 |
| attaacctgc | cgtacatcac | catggacgca | accggcccga | acacttggc | gatgaaaatt | 1260 |
| acccgcgcca | aattcgaaag | cctggttgaa | gacctgatta | cccgctctat | cgaaccttgc | 1320 |
| aaaattgcat | tgaaagatgc | cggcttgagc | accggcgaca | tcgacgacgt | aatcttggtc | 1380 |
| ggcgggcagt | cccgtatgcc | gaaagtacaa | gaagccgtta | aagccttctt | cggcaaagaa | 1440 |
| ccgcgcaaag | acgtgaaccc | tgacgaagcc | gttgccgtag | cgcagcgat | ccaaggcgaa | 1500 |
| gtattgagcg | gcggccgcag | cgacgtattg | ctactggacg | taactcctct | gtctttgggt | 1560 |
| atcgaaacca | tgggcggcgt | gatgaccaaa | ctgattcaga | gaacaccac | catcccgacc | 1620 |
| aaagcgtcgc | aagtgttctc | taccgccgaa | gacaaccaaa | gcgcagtaac | catccacgta | 1680 |
| ctgcaaggcg | aacgcgaacg | cgcttctgcc | aacaaatctt | tgggtcagtt | caacttgggc | 1740 |
| gacatcgcac | ctgcaccgcg | cggtatgccg | caaatcgaag | taaccttcga | catcgacgcc | 1800 |
| aacggcatcc | tgcacgtttc | cgccaaagac | aaaggcaccg | gtaaagcagc | caacatcacc | 1860 |
| atccaaggtt | cttcaggttt | gggcgaagaa | gaaatcgaac | gcatggtgaa | agatgccgaa | 1920 |
| gccaatgccg | aggaagataa | aaaactgact | gaattggtcg | cttcccgcaa | ccaagccgaa | 1980 |
| gccctgattc | actctgtgaa | gaaatctttg | gccgactacg | gcgacaaact | cgatgcagcc | 2040 |

| | |
|---|---:|
| gagaaagaaa aaattgaagc cgcgctgaaa gaagccgaag aagcagttaa aggcgacgac | 2100 |
| aaagccgcta tcgatgccaa aaccgaggcg ctgggcgcag ccagccaaaa actgggggaa | 2160 |
| atggtttacg ctcaagcaca agctgaagcc caagcaggca aaagcgaaca agccaatgct | 2220 |
| tctgcaaaga aagacgatga tgtcgtagat gccgactttg aagaagtaaa agacgacaaa | 2280 |
| aaataattaa taccgtctga aaaaagcgcg aaccgtttga ttcgcgcttt tttcaattga | 2340 |
| gataaaagac catagcataa cagaggttcc aagttcatct accgtaatat tcccaaaccc | 2400 |
| aggttccaac tgttgtatcg gttctctgga attttttata tagtggatta aatttaaacc | 2460 |
| agtac | 2465 |

<210> SEQ ID NO 2
<211> LENGTH: 1929
<212> TYPE: DNA
<213> ORGANISM: Nesseria meningitidis

<400> SEQUENCE: 2

| | |
|---|---:|
| atggcaaaag taatcggtat cgacttaggt acaaccaact cttgtttggc catttccgaa | 60 |
| aacggtcaaa ccaaagtgat cgaaaacgca gaaggcgcac gcaccacgcc gtccgttatc | 120 |
| gcttatttgg acggcggcga atcctcgtc ggtgcgcctg ccaaacgcca agcggtaacc | 180 |
| aacgccaaaa acaccattta cgccgccaaa cgtttgatcg ccacaaaatt tgaagacaaa | 240 |
| gaagtccaac gcgacatcga atctatgcct ttcgaaatca tcaaagccaa caacggcgac | 300 |
| gcatgggtaa agcacaagg caaagagctg tctcctcctc aaatttccgc agaagtcctg | 360 |
| cgtaaaatga agaagccgc cgaagcttac ttgggcgaaa aagtaaccga agccgtgatt | 420 |
| accgtccctg cctacttcaa cgacagccaa cgtcaagcca ccaaagacgc aggccgtatc | 480 |
| gccggtttgg acgtgaaacg catcatcaac gagccgaccg cagccgcttt ggcattcggt | 540 |
| atggacaaag gcgacaacaa agaccgcaaa gtagccgtat atgacttggg cggcggtact | 600 |
| ttcgatattt ccatcatcga aatcgccaac ctcgacggcg acaaacaatt cgaagtattg | 660 |
| gcaaccaacg gcgatacctt cttgggcggt gaagacttcg accaacgcct catcgaccac | 720 |
| atcatcgccg agttcaaaaa agaacaaggc attgatttga acaagacgt gatggctcta | 780 |
| caacgcctga agaagctgc cgaaaaagcc aaaatcgaat tgtccagcgg ccagcaaacc | 840 |
| gaaattaacc tgccgtacat caccatggac gcaaccggcc cgaaacactt ggcgatgaaa | 900 |
| attacccgcg ccaaattcga aagcctggtt gaagacctga ttacccgctc tatcgaacct | 960 |
| tgcaaaattg cattgaaaga tgccggcttg agcaccggcg acatcgacga cgtaatcttg | 1020 |
| gtcggcgggc agtcccgtat gccgaaagta caagaagccg ttaaagcctt cttcggcaaa | 1080 |
| gaaccgcgca aagacgtgaa ccctgacgaa gccgttgccg taggcgcagc gatccaaggc | 1140 |
| gaagtattga gcggcggccg cagcgacgta ttgctactgg acgtaactcc tctgtctttg | 1200 |
| ggtatcgaaa ccatgggcgg cgtgatgacc aaactgattc agaagaacac caccatcccg | 1260 |
| accaaagcgt cgcaagtgtt ctctaccgcc gaagacaacc aaagcgcagt aaccatccac | 1320 |
| gtactgcaag gcgaacgcga acgcgcttct gccaacaaat cttttgggtca gttcaacttg | 1380 |
| ggcgacatcg cacctgcacc gcgcggtatg ccgcaaatcg aagtaacctt cgacatcgac | 1440 |
| gccaacggca tcctgcacgt ttccgccaaa gacaaaggca ccggtaaagc agccaacatc | 1500 |
| accatccaag gttcttcagg tttgagcgaa gaagaaatcg aacgcatggt gaaagatgcc | 1560 |
| gaagccaatg ccgaggaaga taaaaaactg actgaattgg tcgcttcccg caaccaagcc | 1620 |

-continued

```
gaagccctga ttcactctgt gaaaaatct ttggccgact acggcgacaa actcgatgca       1680
gccgagaaag aaaaaattga agccgcgctg aaagaagccg aagaagcagt taaaggcgac       1740
gacaaagccg ctatcgatgc caaaaccgag gcgctgggcg cagccagcca aaaactgggg       1800
gaaatggttt acgctcaagc acaagctgaa gcccaagcag gcgaaagcga acaagccaat       1860
gcttctgcaa agaaagacga tgatgtcgta gatgccgact tgaagaagt aaaagacgac       1920 aaaaaataa                                                               1929

<210> SEQ ID NO 3
<211> LENGTH: 1929
<212> TYPE: DNA
<213> ORGANISM: Nesseria meningitidis

<400> SEQUENCE: 3
atggcaaaag taatcggtat cgacttaggt acaaccaact cttgtttggc catttccgaa         60
aacggtcaaa ccaaagtgat cgaaaacgca gaaggcgcac gcaccacgcc gtccgttatc        120
gcttatttgg acggcggcga aatcctcgtc ggtgcgcctg ccaaacgcca agcgtaacc         180 aacgccaaaa acaccattta cgccgccaaa cgtttgatcg gccacaaatt tgaagacaaa        240
gaagtccaac gcgacatcga atctatgcct ttcgaaatca tcaaagccaa caacggcgac        300
gcatgggtaa agcacaagg caaagagctg tctcctcctc aaatttccgc agaagtcctg        360
cgtaaaatga agaagccgc cgaagcttac ttgggcgaaa agtaaccga agccgtgatt         420 accgtccctg cctacttcaa cgacagccaa cgtcaagcca ccaaagacgc aggccgtatc        480
gccggtttgg acgtgaaacg catcatcaac gagccgaccg cagccgcttt ggcattcggt        540
atggacaaag gcgacaacaa agaccgcaaa gtagccgtat atgacttggg cggcggtact        600
ttcgatattt ccatcatcga aatcgccaac ctcgacggcg acaaacaatt cgaagtattg        660
gcaaccaacg gcgataccct tctgggcggt gaagacttcg accaacgcct catcgaccac        720
atcatcgccg agttcaaaaa agaacaaggc attgatttga acaagacgt gatggctcta         780 caacgcctga agaagctgc cgaaaaagcc aaatcgaat tgtccagcgg ccagcaaacc          840
gaaattaacc tgccgtacat caccatggac gcaaccggcc cgaaacactt ggcgatgaaa        900
attacccgcg ccaaattcga aagcctggtt gaagacctga ttacccgctc tatcgaacct        960
tgcaaaattg cattgaaaga tgccggcttg agcaccggcg acatcgacga cgtaatcttg       1020
gtcggcgggc agtcccgtat gccgaaagta caagaagccg ttaaagcctt cttcggcaaa       1080
gaaccgcgca agacgtgaa ccctgacgaa gccgttgccg taggcgcagc gatccaaggc       1140
gaagtattga gcgcggccg cagcgacgta ttgctactgg acgtaactcc tctgtctttg        1200
ggtatcgaaa ccatgggcgg cgtgatgacc aaactgattc agaagaacac caccatcccg       1260
accaaagcgt cgcaagtgtt ctctaccgcc gaagacaacc aaagcgcagt aaccatccac       1320
gtactgcaag gcgaacgcga acgcgcttct gccaacaaat ctttgggtca gttcaacttg       1380
ggcgacatcg cacctgcacc gcgcggtatg ccgcaaatcg aagtaacctt cgacatcgac       1440
gccaacggca tcctgcacgt ttccgccaaa gacaaaggca ccggtaaagc agccaacatc       1500
accatccaag gttcttcagg tttgagcgaa gaagaaatcg aacgcatggt gaaagatgcc       1560
gaagccaatg ccgaggaaga taaaaaactg actgaattgg tcgcttcccg caaccaagcc       1620
gaagccctga ttcactctgt gaaaaaatct ttggccgact acggcgacaa actcgatgca       1680
gccgagaaag aaaaaattga agccgcgctg aaagaagccg aagaagcagt taaaggcgac       1740
gacaaagccg ctatcgatgc caaaaccgag gcgctgggcg cagccagcca aaaactgggg       1800
```

-continued

```
gaaatggttt acgctcaagc acaagctgaa gcccaagcag gcgaaagcga acaagccaat    1860
gcttctgcaa agaaagacga tgatgtcgta gatgccgact ttgaagaagt aaaagacgac    1920
aaaaaataa                                                            1929
```

<210> SEQ ID NO 4
<211> LENGTH: 1989
<212> TYPE: DNA
<213> ORGANISM: Nesseria meningitidis

<400> SEQUENCE: 4

```
atgggcagca gccatcatca tcatcatcac agcagcggcc tggtgccgcg cggcagccat      60
atggcaaaag taatcggtat cgacttaggt acaaccaact cttgtttggc catttccgaa     120
aacggtcaaa ccaaagtgat cgaaaacgca gaaggcgcac gcaccacgcc gtccgttatc     180
gcttatttgg acgcggcga aatcctcgtc ggtgcgcctg ccaaacgcca agcggtaacc     240
aacgccaaaa acaccattta cgccgccaaa cgtttgatcg ccacaaaatt tgaagacaaa     300
gaagtccaac gcgacatcga atctatgcct ttcgaaatca tcaaagccaa caacggcgac     360
gcatgggtaa aagcacaagg caaagagctg tctcctcctc aaatttccgc agaagtcctg     420
cgtaaaatga agaagccgc cgaagcttac ttgggcgaaa agtaaccga agccgtgatt     480 accgtccctg cctacttcaa cgacagccaa cgtcaagcca ccaaagacgc aggccgtatc     540
gccggtttgg acgtgaaacg catcatcaac gagccgaccg cagccgcttt ggcattcggt     600
atggacaaag gcgacaacaa agaccgcaaa gtagccgtat atgacttggg cggcggtact     660
ttcgatattt ccatcatcga aatcgccaac ctcgacggcg acaaacaatt cgaagtattg     720
gcaaccaacg gcgatacctt cttgggcggt gaagacttcg accaacgcct catcgaccac     780
atcatcgccg agttcaaaaa agaacaaggc attgatttga acaagacgt gatggctcta     840 caacgcctga agaagctgc cgaaaaagcc aaaatcgaat tgtccagcgg ccagcaaacc     900
gaaattaacc tgccgtacat caccatggac gcaaccggcc cgaaacactt ggcgatgaaa     960
attacccgcg ccaaattcga aagcctggtt gaagacctga ttacccgctc tatcgaacct    1020
tgcaaaattg cattgaaaga tgccggcttg agcaccggcg acatcgacga cgtaatcttg    1080
gtcggcgggc agtcccgtat gccgaaagta caagaagccg ttaaagcctt cttcggcaaa    1140
gaaccgcgca agacgtgaa ccctgacgaa gccgttgccg taggcgcagc gatccaaggc    1200
gaagtattga gcggcggccg cagcgacgta ttgctactgg acgtaactcc tctgtctttg    1260
ggtatcgaaa ccatgggcgg cgtgatgacc aaactgattc agaagaacac caccatcccg    1320
accaaagcgt cgcaagtgtt ctctaccgcc gaagacaacc aaagcgcagt aaccatccac    1380
gtactgcaag cgaacgcga acgcgcttct gccaacaaat ctttgggtca gttcaacttg    1440
ggcgacatcg cacctgcacc gcgcggtatg ccgcaaatcg aagtaacctt cgacatcgac    1500
gccaacggca tcctgcacgt ttccgccaaa gacaaaggca ccggtaaagc agccaacatc    1560
accatccaag gttcttcagg tttgagcgaa gaagaaatca acgcatggt gaaagatgcc    1620 gaagccaatg ccgaggaaga taaaaaactg actgaattgg tcgcttcccg caaccaagcc    1680
gaagccctga ttcactctgt gaaaaaatct ttggccgact acggcgacaa actcgatgca    1740
gccgagaaag aaaaaattga agccgcgctg aaagaagccg aagaagcagt taaggcgac    1800 gacaaagccg ctatcgatgc caaaaccgag gcgctgggcg cagccagcca aaaactgggg    1860
gaaatggttt acgctcaagc acaagctgaa gcccaagcag gcgaaagcga acaagccaat    1920
```

-continued

| | |
|---|---|
| gcttctgcaa agaaagacga tgatgtcgta gatgccgact ttgaagaagt aaaagacgac | 1980 |
| aaaaaataa | 1989 |

<210> SEQ ID NO 5
<211> LENGTH: 2480
<212> TYPE: DNA
<213> ORGANISM: Aspergillus fumigatus

<400> SEQUENCE: 5

| | |
|---|---|
| gtacgaattt cccctttccga cgatccgaga acgtccctcg ggaaggccac acgtgacctt | 60 |
| ctaggagctt ctcccgccaa gacatccggg gatcgagaat cgcctggaaa aatttcgaga | 120 |
| ctttggcttc atctccccag ctttcatctc cattccatct tccttacctt ctattccccc | 180 |
| tcttctcttc cttctctgca cctgttcttg ctctgggagg ttcgatcggg cagtagtgtt | 240 |
| catcttaacg ttgattatat tctcttctat cccgtccttt catcacccct ctttccataa | 300 |
| tgcagagagc tctttcttcc aggacgtctg tcctttccgc tgcctccaaa cgggctgctt | 360 |
| tcaccaagcc cgctggcctt aacctgcagc agcagcgttt cgcccacaag gtatgttttc | 420 |
| atctacaatc tagaatttta agcttctgaa gtggtgccaa tttctccgtg tcacccggag | 480 |
| ctcaaccccg ataccttgct aacgaacttt caggagctca agttcggtgt cgaagcccgt | 540 |
| gctcagctcc tcaagggtgt tgacactctg gccaaggccg tgacttcgac tcttggtcct | 600 |
| aagggtcgta acgtccttat cgagtctccc tatggctccc ctaagatcac caagggtacg | 660 |
| tttgactcga gttaacccaa gtcgctgctt tcacaaacga attgtggttc tgactaaaaa | 720 |
| tagatggtgt ctctgttgcc aaggccatca ctctccaaga caagttcgag aacctcggtg | 780 |
| ctcgcctcct ccaggatgtc gcttctaaga ccaacgagat tgctggtgac ggtaccacca | 840 |
| ccgctaccgt ccttgcccgt gccatcttct ctgagaccgt gaagaatgtt gctgctggct | 900 |
| gcaaccccat ggatctgcgc gcggtatcc aggctgctgt tgatgctgtc gtcgactacc | 960 |
| tccagaagaa caagcgtgac atcaccaccg tgaggagat cgctcaggtt gctactatct | 1020 |
| ccgctaacgt tgacacccac attggtaagc tgatctccac cgccatggag cgtgttggca | 1080 |
| aggagggtgt catcactgtc aaggagggca agaccattga ggatgagctc gaggtcactg | 1140 |
| agggtatgcg cttcgaccgt ggatacacct cccctactt catcaccgat accaagtccc | 1200 |
| agaaggttga gttcgagaag cctctgattc tgctgtctga agaagatc tctgccgttc | 1260 |
| aggacatcat ccccgcgcctt gaggcctcca ccacctccg ccgcccctg gttattatcg | 1320 |
| cagaggacat tgagggtgag gctctcgccg tctgcattct gaacaagctt cgtggccagc | 1380 |
| tgcaggtcgc tgctgtcaag gctcctggat tcggtgacaa ccgcaagagc atcctgggcg | 1440 |
| atcttgccgt ccttaccaac ggtaccgtct tcactgatga gctcgacatc aaactcgaga | 1500 |
| agcttacccc cgatatgctt ggttccaccg gcgccatcac catcaccaag gaggacacca | 1560 |
| tcatcctgaa cggggagggc agcaaggacg ccattgccca gcgctgcgag cagattcgcg | 1620 |
| gtgtcatggc ggaccccagc acctccgaat acgagaagga gaagctccag gagcgtctag | 1680 |
| ctaagctctc tggcggtgtt gccgtcatca aggtcggtgg tgcctccgag gttgaggtcg | 1740 |
| gtgagaagaa ggaccgtgtt gtcgatgctc tcaatgctac ccgtgctgct gttgaggagg | 1800 |
| gtatcctccc cggtggtggt accgcccttc tcaaggccgc cgccaacggc cttgacaatg | 1860 |
| tcaagcccga gaacttcgac cagcaactcg gtgtgagcat catcaagaat gccatcaccc | 1920 |
| gccccgctcg caccattgtt gagaacgccg gcctcgaggg cagcgtcatt gtcggcaagc | 1980 |
| tgaccgacga gttcgccaag gacttcaacc gcggtttcga cagctccaag ggcgagtacg | 2040 |

-continued

| | |
|---|---|
| tcgacatgat ctccagcggt atcctcgatc ccctcaaggt tgttcgcacc gctctgctcg | 2100 |
| acgccagcgg tgtcgcctcc ctgctcggta ccactgaggt cgctattgtt gaggcccctg | 2160 |
| aggagaaggg ccccgctgct cctggcatgg gtggtatggg tggtatgggc ggcatgggtg | 2220 |
| gcggcatgtt ctaagctgct cccagttgcc tttgctacca tagcctcttc catgatttaa | 2280 |
| aggtttaact tcccttcga gcgtgtcttt gcatgtacga gcatttcctg atatatcggt | 2340 |
| gttgagagtt ttctgtaatt tttcctttgt ttctgatgtg ttacacgcct tgacagcccc | 2400 |
| ttcacctact ccgacttcgt cttataactc gatactcata tctccctctt cgacccgcct | 2460 |
| cccctttgat tgactcgatc | 2480 |

<210> SEQ ID NO 6
<211> LENGTH: 1653
<212> TYPE: DNA
<213> ORGANISM: Aspergillus fumigatus

<400> SEQUENCE: 6

| | |
|---|---|
| atgaaagagc tcaagttcgg tgtcgaagcc cgtgctcagc tcctcaaggg tgttgacact | 60 |
| ctggccaagg ccgtgacttc gactcttggt cctaagggtc gtaacgtcct tatcgagtct | 120 |
| ccctatggct cccctaagat caccaaggat ggtgtctctg ttgccaaggc catcactctc | 180 |
| caagacaagt tcgagaacct cggtgctcgc ctcctccagg atgtcgcttc taagaccaac | 240 |
| gagattgctg gtgacggtac caccaccgct accgtccttg cccgtgccat cttctctgag | 300 |
| accgtgaaga atgttgctgc tggctgcaac cccatggatc tgcgccgcgg tatccaggct | 360 |
| gctgttgatg ctgtcgtcga ctacctccag aagaacaagc gtgacatcac caccggtgag | 420 |
| gagatcgctc aggttgctac tatctccgct aacggtgaca cccacattgg taagctgatc | 480 |
| tccaccgcca tggagcgtgt tggcaaggag ggtgtcatca ctgtcaagga gggcaagacc | 540 |
| attgaggatg agctcgaggt cactgagggt atgcgcttcg accgtggata cacctccccc | 600 |
| tacttcatca ccgataccaa gtcccagaag gttgagttcg agaagcctct gattctgctg | 660 |
| tctgagaaga agatctctgc cgttcaggac atcatccccg cccttgaggc ctccaccacc | 720 |
| ctccgccgcc cctggttat tatcgcagag gacattgagg gtgaggctct cgccgtctgc | 780 |
| attctgaaca agcttcgtgg ccagctgcag gtcgctgctg tcaaggctcc tggattcggt | 840 |
| gacaaccgca agagcatcct gggcgatctt gccgtcctta ccaacggtac cgtcttcact | 900 |
| gatgagctcg acatcaaact cgagaagctt acccccgata tgcttggttc caccggcgcc | 960 |
| atcaccatca ccaaggagga caccatcatc ctgaacgggg agggcagcaa ggacgccatt | 1020 |
| gcccagcgct gcgagcagat tcgcggtgtc atggcggacc ccagcacctc cgaatacgag | 1080 |
| aaggagaagc tccaggagcg tctagctaag ctctctggcg gtgttgccgt catcaaggtc | 1140 |
| ggtggtgcct ccgaggttga ggtcggtgag aagaaggacc gtgttgtcga tgctctcaat | 1200 |
| gctacccgtg ctgctgttga ggagggtatc ctccccggtg gtggtaccgc ccttctcaag | 1260 |
| gccgccgcca acgccttga caatgtcaag cccgagaact cgaccagca actcggtgtg | 1320 |
| agcatcatca gaatgccat cacccgcccc gctcgcacca ttgttgagaa cgccggcctc | 1380 |
| gagggcagcg tcattgtcgg caagctgacc gacgagttcg ccaaggactt caaccgcggt | 1440 |
| ttcgacagct ccaagggcga gtacgtcgac atgatctcca gcggtatcct cgatcccctc | 1500 |
| aaggttgttc gcaccgctct gctcgacgcc agcggtgtcg cctccctgct cggtaccact | 1560 |
| gaggtcgcta ttgttgaggc ccctgaggag aagggccccg ctgctcctgg catgggtggt | 1620 |

-continued

```
atgggtggta tgggcggcat gggcggcatg tag                    1653

<210> SEQ ID NO 7
<211> LENGTH: 1713
<212> TYPE: DNA
<213> ORGANISM: Aspergillus fumigatus

<400> SEQUENCE: 7
atgggcagca gccatcatca tcatcatcac agcagcggcc tggtgccgcg cggcagccat      60
atgaaagagc tcaagttcgg tgtcgaagcc cgtgctcagc tcctcaaggg tgttgacact     120
ctggccaagg ccgtgacttc gactcttggt cctaagggtc gtaacgtcct tatcgagtct     180
ccctatggct cccctaagat caccaaggat ggtgtctctg ttgccaaggc catcactctc     240
caagacaagt tcgagaacct cggtgctcgc ctcctccagg atgtcgcttc taagaccaac     300
gagattgctg gtgacggtac caccaccgct accgtccttg cccgtgccat cttctctgag     360
accgtgaaga atgttgctgc tggctgcaac cccatggatc tgcgccgcgg tatccaggct     420
gctgttgatg ctgtcgtcga ctacctccag aagaacaagc gtgacatcac caccggtgag     480
gagatcgctc aggttgctac tatctccgct aacggtgaca cccacattgg taagctgatc     540
tccaccgcca tggagcgtgt tggcaaggag ggtgtcatca ctgtcaagga gggcaagacc     600
attgaggatg agctcgaggt cactgagggt atgcgcttcg accgtggata cacctccccc     660
tacttcatca ccgataccaa gtcccagaag gttgagttcg agaagcctct gattctgctg     720
tctgagaaga agatctctgc cgttcaggac atcatccccg cccttgaggc ctccaccacc     780
ctccgccgcc cctggttat tatcgcagag gacattgagg gtgaggctct cgccgtctgc     840
attctgaaca agcttcgtgg ccagctgcag gtcgctgctg tcaaggctcc tggattcggt     900
gacaaccgca agagcatcct gggcgatctt gccgtcctta ccaacggtac cgtcttcact     960
gatgagctcg acatcaaact cgagaagctt accccgata tgcttggttc caccggcgcc    1020
atcaccatca ccaaggagga caccatcatc ctgaacgggg agggcagcaa ggacgccatt    1080
gcccagcgct gcgagcagat cgcggtgtc atggcggacc ccagcacctc cgaatacgag    1140
aaggagaagc tccaggagcg tctagctaag ctctctggcg gtgttgccgt catcaaggtc    1200
ggtggtgcct ccgaggttga ggtcggtgag aagaaggacc gtgttgtcga tgctctcaat    1260
gctacccgtg ctgctgttga ggagggtatc ctccccggtg gtggtaccgc ccttctcaag    1320
gccgccgcca acgccttga caatgtcaag cccgagaact cgaccagca actcggtgtg    1380 agcatcatca gaatgccat cacccgcccc gctcgcacca ttgttgagaa cgccggcctc    1440
gagggcagcg tcattgtcgg caagctgacc gacgagttcg ccaaggactt caaccgcggt    1500
ttcgacagct ccaagggcga gtacgtcgac atgatctcca gcggtatcct cgatcccctc    1560
aaggttgttc gcaccgctct gctcgacgcc agcggtgtcg cctccctgct cggtaccact    1620
gaggtcgcta ttgttgaggc ccctgaggag aagggccccg ctgctcctgg catgggtggt    1680
atgggtggta tgggcggcat gggcggcatg tag                                1713

<210> SEQ ID NO 8
<211> LENGTH: 2051
<212> TYPE: DNA
<213> ORGANISM: Candida glabrata

<400> SEQUENCE: 8
ccgggtaaag tacctgattg cgcacttaca gctaacagct gacgcactcg agaaatctgc      60
ccgttttgtt catggaaact tgaagaaaat cagggaaatc gttactgcgc tctctctaac     120
```

```
gcttgcaagc tcctggaata caaattcgca aagtatataa ctctatagct ttcaaccttg      180
ttactgtgga gtagctgtta agggatagag acataagata aaccatacca tacataaatc      240
accccccata taaacaaatg ttgagagctg ttgcacgttc gcaggttaga tctttgagaa      300
acgctcgttt gtactccagt ttcaaggagt tgaagttcgg tgtcgaaggc agagctgctc      360
tgcttcgtgg tgtcgagact ttggccgacg ctgtctctgc cacgctgggg cctaagggta      420
gaaatgtgct gatcgagcag ccattcggag caccaaagat caccaaggat ggtgtcaccg      480
tggccagatc cattactttg gaggacaagt tcgagaacat gggtgctaag cttctgcaag      540
aagttgcctc caagactaac gaggccgccg gtgacggtac cacctccgcc actgtcttgg      600
gtagagccat cttcaccgag tccgtcaaga acgtcgctgc cggttgcaac cctatggatt      660
tgagaagggg ttcccaggcc gccgtcgaga aggtcatcca attcttgact gaaaacaaga      720
aggagatcac cacttctgag gaaatcgccc aggtggccac catctcagct aacggtgacg      780
ctcacgtcgg taagttgctt gcctccgcca tggaaaaggt tggcaaggaa ggtgttatca      840
ccatcagaga aggcagaact ttggaagacg aactagaagt caccgaaggt atgagatttg      900
accgtggttt catctcccca tacttcatca ctgacgcaaa gtccggcaag gtagaattcg      960
aaaagccatt gttgttgttg agcgaaaaga agatctcttc catccaagac atcttgccag     1020
ctttggaact atctaaccaa agtagaagac cactattgat catcgccgaa gatgtcgacg     1080
gtgaagccct agctgcttgt atcctaaaca agttgagagg ccaagtcaag gtctgtgccg     1140
ttaaggctcc aggtttcggt gacaacagaa agaacattct aggtgatgtc gccatcttga     1200
ccggcagtac tgttttact gaagaattgg acttgaagcc agaacaagcc actatggaac     1260
acctaggttc ctgtgactcc attactatca caaaggaaga cactgttatc ctaaacggta     1320
acggctccaa ggactctatc caagaaagaa ttgaacagat caagaactcc attgatgtca     1380
ccactactaa ctcttacgag aaggagaagc tacaagaaag acttgccaag ttatccggtg     1440
gtgttgctgt catcagggtt ggtggtgctt ctgaagttga agtcggtgaa aagaaggacc     1500
gttacgatga cgctttgaat gccaccgagg ctgccgttga agaaggtatc ttaccaggtg     1560
gtggtactgc tttggttaag gcctctagag ttttagacga agtcaagact gagaacttcg     1620
accaaaaatt gggagttgac attatcagaa aggccattac tagaccagct aagcaaatta     1680 ttgaaacgc cggtgaagaa ggctccgtta ttgtcggtaa gcttgttgat gaatttggcg     1740
aagattttgc taagggttac gactccgcta agggagaatt cactgatatg ttggctgccg     1800
gtattattga cccattcaaa gtcgttagat ctggtctggt cgacgcttcc ggtgttgctt     1860
ccttgttggc tactaccgaa gttgccatcg ttgacgctcc tgaaccagct ccagctgctg     1920
gtgccccagg tggtggtatg ccaggtatgc caggtatgat gtaaaaggtc taacttttgc     1980
aatcatgctg gtgaaaatga agcaaatcat tacatagagt ggtaaaatct tcaagaccaa     2040
atagcttgta c                                                         2051
```

<210> SEQ ID NO 9
<211> LENGTH: 1647
<212> TYPE: DNA
<213> ORGANISM: Candida glabrata

<400> SEQUENCE: 9

```
atggccaagg agttgaagtt tgggggtcgaa ggcagagctg ctctgcttcg tggtgtcgag       60
actttggccg acgctgtctc tgccacgctg gggcctaagg gtagaaatgt gctgatcgag      120
```

-continued

| | |
|---|---|
| cagccattcg gagcaccaaa gatcaccaag gatggtgtca ccgtggccag atccattact | 180 |
| ttggaggaca agttcgagaa catgggtgct aagcttctgc aagaagttgc ctccaagact | 240 |
| aacgaggccg ccggtgacgg taccacctcc gccactgtct tgggtagagc catcttcacc | 300 |
| gagtccgtca agaacgtcgc tgccggttgc aaccctatgg atttgagaag gggttcccag | 360 |
| gccgccgtcg agaaggtcat ccaattcttg actgaaaaca agaaggagat caccacttct | 420 |
| gaggaaatcg cccaggtggc caccatctca gctaacggtg acgctcacgt cggtaagttg | 480 |
| cttgcctccg ccatggaaaa ggttggcaag gaaggtgtta tcaccatcag agaaggcaga | 540 |
| actttggaag acgaactaga agtcaccgaa ggtatgagat ttgaccgtgg tttcatctcc | 600 |
| ccatacttca tcactgacgc aaagtccggc aaggtagaat cgaaaagcc attgttgttg | 660 |
| ttgagcgaaa agaagatctc ttccatccaa gacatcttgc cagctttgga actatctaac | 720 |
| caaagtagaa gaccactatt gatcatcgcc gaagatgtcg acggtgaagc cctagctgct | 780 |
| tgtatcctaa acaagttgag aggccaagtc aaggtctgtg ccgttaaggc tccaggtttc | 840 |
| ggtgacaaca gaaagaacat tctaggtgat gtcgccatct tgaccggcag tactgttttt | 900 |
| actgaagaat tggacttgaa gccagaacaa gccactatg aacacctagg ttcctgtgac | 960 |
| tccattacta tcacaaagga agacactgtt atcctaaacg gtaacggctc caaggactct | 1020 |
| atccaagaaa gaattgaaca gatcaagaac tccattgatg tcaccactac taactcttac | 1080 |
| gagaaggaga agctacaaga aagacttgcc aagttatccg gtggtgttgc tgtcatcagg | 1140 |
| gttggtggtg cttctgaagt tgaagtcggt gaaagaagg accgttacga tgacgctttg | 1200 |
| aatgccacca gagctgccgt tgaagaaggt atcttaccag gtggtggtac tgctttggtt | 1260 |
| aaggcctcta gagtttaga cgaagtcaag actgagaact tcgaccaaaa attgggagtt | 1320 |
| gacattatca gaaaggccat tactagacca gctaagcaaa ttattgagaa cgccggtgaa | 1380 |
| gaaggctccg ttattgtcgg taagcttgtt gatgaatttg gcgaagattt tgctaagggt | 1440 |
| tacgactccg ctaagggaga attcactgat atgttggctg ccggtattat tgacccattc | 1500 |
| aaagtcgtta gatctggtct ggtcgacgct tccggtgttg cttccttgtt ggctactacc | 1560 |
| gaagttgcca tcgttgacgc tcctgaacca gctccagctg ctggtgcccc aggtggtggt | 1620 |
| atgccaggta tgccaggtat gatgtaa | 1647 |

<210> SEQ ID NO 10
<211> LENGTH: 1707
<212> TYPE: DNA
<213> ORGANISM: Candida glabrata

<400> SEQUENCE: 10

| | |
|---|---|
| atgggcagca gccatcatca tcatcatcac agcagcggcc tggtgccgcg cggcagccat | 60 |
| atggccaagg agttgaagtt tggggtcgaa ggcagagctg ctctgcttcg tggtgtcgag | 120 |
| actttggccg acgctgtctc tgccacgctg gggcctaagg gtagaaatgt gctgatcgag | 180 |
| cagccattcg gagcaccaaa gatcaccaag gatggtgtca ccgtggccag atccattact | 240 |
| ttggaggaca agttcgagaa catgggtgct aagcttctgc aagaagttgc ctccaagact | 300 |
| aacgaggccg ccggtgacgg taccacctcc gccactgtct tgggtagagc catcttcacc | 360 |
| gagtccgtca agaacgtcgc tgccggttgc aaccctatgg atttgagaag gggttcccag | 420 |
| gccgccgtcg agaaggtcat ccaattcttg actgaaaaca agaaggagat caccacttct | 480 |
| gaggaaatcg cccaggtggc caccatctca gctaacggtg acgctcacgt cggtaagttg | 540 |
| cttgcctccg ccatggaaaa ggttggcaag gaaggtgtta tcaccatcag agaaggcaga | 600 |

```
actttggaag acgaactaga agtcaccgaa ggtatgagat ttgaccgtgg tttcatctcc    660
ccatacttca tcactgacgc aaagtccggc aaggtagaat tcgaaaagcc attgttgttg    720
ttgagcgaaa agaagatctc ttccatccaa gacatcttgc cagctttgga actatctaac    780
caaagtagaa gaccactatt gatcatcgcc gaagatgtcg acgtgaagc cctagctgct     840 tgtatcctaa acaagttgag aggccaagtc aaggtctgtg ccgttaaggc tccaggtttc    900
ggtgacaaca gaaagaacat tctaggtgat gtcgccatct tgaccggcag tactgttttt    960
actgaagaat tggacttgaa gccagaacaa gccactatgg aacacctagg ttcctgtgac   1020
tccattacta tcacaaagga agacactgtt atcctaaacg gtaacggctc aaggactct    1080 atccaagaaa gaattgaaca gatcaagaac tccattgatg tcaccactac taactcttac   1140
gagaaggaga agctacaaga aagacttgcc aagttatccg gtggtgttgc tgtcatcagg   1200
gttggtggtg cttctgaagt tgaagtcggt gaaagaagg accgttacga tgacgctttg    1260
aatgccacca gagctgccgt tgaagaaggt atcttaccag gtggtggtac tgctttggtt   1320
aaggcctcta gagttttaga cgaagtcaag actgagaact tcgaccaaaa attgggagtt   1380
gacattatca gaaaggccat tactagacca gctaagcaaa ttattgagaa cgccggtgaa   1440
gaaggctccg ttattgtcgg taagcttgtt gatgaatttg gcgaagattt tgctaagggt   1500
tacgactccg ctaagggaga attcactgat atgttggctg ccggtattat tgacccattc   1560
aaagtcgtta gatctggtct ggtcgacgct tccggtgttg cttccttgtt ggctactacc   1620
gaagttgcca tcgttgacgc tcctgaacca gctccagctg ctggtgcccc aggtggtggt   1680
atgccaggta tgccaggtat gatgtaa                                      1707
```

<210> SEQ ID NO 11
<211> LENGTH: 1005
<212> TYPE: DNA
<213> ORGANISM: Neisseria meningitidis

<400> SEQUENCE: 11

```
cctgcdtatt tcaacgacag ccaacgtcaa gccaccaaag acgcaggccg tatcgccggt      60
ttggacgtga aacgcatcat caacgagccg accgcagccg cttggcatt cggtatggac      120 aaaggcgaca acaaagaccg caaagtagcc gtatatgact tgggcggcgg tactttcgat     180
atttccatca tcgaaatcgc caacctcgac ggcgacaaac aattcgaagt attggcaacc     240
aacggcgata ccttcttggg cggtgaagac ttcgaccaac gcctcatcga ccacatcatc     300
gccgagttca aaaagaaca aggcattgat ttgaaacaag acgtgatggc tctacaacgc     360
ctgaaagaag ctgccgaaaa agccaaaatc gaattgtcca gcggccagca accgaaatt     420 aacctgccgt acatcaccat ggacgcaacc ggcccgaaac acttggcgat gaaaattacc     480
cgcgccaaat tcgaaagcct ggttgaagac ctgattaccc gctctatcga accttgcaaa     540
attgcattga agatgccggg cttgagcacc ggcgacatcg acgacgtaat cttggtcggc     600
gggcagtccc gtatgccgaa agtacaagaa gccgttaaag ccttcttcgg caaagaaccg     660
cgcaaagacg tgaaccctga cgaagccgtt gccgtaggcg cagcgatcca aggcgaagta     720
ttgagcggcg gccgcagcga cgtattgcta ctggacgtaa ctcctctgtc tttgggtatc     780
gaaaccatgg gcggcgtgat gaccaaactg attcagaaga acaccaccat cccgaccaaa     840
gcgtcgcaag tgttctctac cgccgaagac aaccaaagcg cagtaaccat ccacgtactg     900
caaggcgaac gcgaacgcgc ttctgccaac aaaatctttg gtcagttcaa cttgggcgac     960
```

```
atcgcacctg caccgcgcgg tatgccacaa atcgaagtaa chttt         1005
```

<210> SEQ ID NO 12
<211> LENGTH: 415
<212> TYPE: PRT
<213> ORGANISM: Neisseria meningitidis

<400> SEQUENCE: 12

```
Met Ala Lys Val Ile Gly Ile Asp Leu Gly Thr Thr Asn Ser Cys Leu
 1               5                  10                  15

Ala Ile Ser Glu Asn Gly Gln Thr Lys Val Ile Glu Asn Ala Glu Gly
            20                  25                  30

Ala Arg Thr Thr Pro Ser Val Ile Ala Tyr Leu Asp Gly Gly Glu Ile
        35                  40                  45

Leu Val Gly Ala Pro Ala Lys Arg Gln Ala Val Thr Asn Ala Lys Asn
 50                  55                  60

Thr Ile Tyr Ala Ala Lys Arg Leu Ile Gly His Lys Phe Glu Asp Lys
 65                  70                  75                  80

Pro Ala Tyr Phe Asn Asp Ser Gln Arg Gln Ala Thr Lys Asp Ala Gly
                85                  90                  95

Arg Ile Ala Gly Leu Asp Val Lys Arg Ile Ile Asn Glu Pro Thr Ala
            100                 105                 110

Ala Ala Leu Ala Phe Gly Met Asp Lys Gly Asp Asn Lys Asp Arg Lys
        115                 120                 125

Val Ala Val Tyr Asp Leu Gly Gly Gly Thr Phe Asp Ile Ser Ile Ile
    130                 135                 140

Glu Ile Ala Asn Leu Asp Gly Asp Lys Gln Phe Glu Val Leu Ala Thr
145                 150                 155                 160

Asn Gly Asp Thr Phe Leu Gly Gly Glu Asp Phe Asp Gln Arg Leu Ile
                165                 170                 175

Asp His Ile Ile Ala Glu Phe Lys Lys Glu Gln Gly Ile Asp Leu Lys
            180                 185                 190

Gln Asp Val Met Ala Leu Gln Arg Leu Lys Glu Ala Ala Glu Lys Ala
        195                 200                 205

Lys Ile Glu Leu Ser Ser Gly Gln Gln Thr Glu Ile Asn Leu Pro Tyr
    210                 215                 220

Ile Thr Met Asp Ala Thr Gly Pro Lys His Leu Ala Met Lys Ile Thr
225                 230                 235                 240

Arg Ala Lys Phe Glu Ser Leu Val Glu Asp Leu Ile Thr Arg Ser Ile
                245                 250                 255

Glu Pro Cys Lys Ile Ala Leu Lys Asp Ala Gly Leu Ser Thr Gly Asp
            260                 265                 270

Ile Asp Asp Val Ile Leu Val Gly Gly Gln Ser Arg Met Pro Lys Val
        275                 280                 285

Gln Glu Ala Val Lys Ala Phe Phe Gly Lys Glu Pro Arg Lys Asp Val
    290                 295                 300

Asn Pro Asp Glu Ala Val Ala Val Gly Ala Ala Ile Gln Gly Glu Val
305                 310                 315                 320

Leu Ser Gly Gly Arg Ser Asp Val Leu Leu Asp Val Thr Pro Leu
                325                 330                 335

Ser Leu Gly Ile Glu Thr Met Gly Gly Val Met Thr Lys Leu Ile Gln
            340                 345                 350

Lys Asn Thr Thr Ile Pro Thr Lys Ala Ser Gln Val Phe Ser Thr Ala
        355                 360                 365
```

```
Glu Asp Asn Gln Ser Ala Val Thr Ile His Val Leu Gln Gly Glu Arg
    370                 375                 380

Glu Arg Ala Ser Ala Asn Lys Ser Leu Gly Gln Phe Asn Leu Gly Asp
385                 390                 395                 400

Ile Ala Pro Ala Pro Arg Gly Met Pro Gln Ile Glu Val Thr Phe
                405                 410                 415

<210> SEQ ID NO 13
<211> LENGTH: 642
<212> TYPE: PRT
<213> ORGANISM: Neisseria meningitidis

<400> SEQUENCE: 13

Met Ala Lys Val Ile Gly Ile Asp Leu Gly Thr Thr Asn Ser Cys Leu
  1               5                  10                  15

Ala Ile Ser Glu Asn Gly Gln Thr Lys Val Ile Glu Asn Ala Glu Gly
                 20                  25                  30

Ala Arg Thr Thr Pro Ser Val Ile Ala Tyr Leu Asp Gly Gly Glu Ile
             35                  40                  45

Leu Val Gly Ala Pro Ala Lys Arg Gln Ala Val Thr Asn Ala Lys Asn
     50                  55                  60

Thr Ile Tyr Ala Ala Lys Arg Leu Ile Gly His Lys Phe Glu Asp Lys
 65                  70                  75                  80

Glu Val Gln Arg Asp Ile Glu Ser Met Pro Phe Glu Ile Ile Lys Ala
                 85                  90                  95

Asn Asn Gly Asp Ala Trp Val Lys Ala Gln Gly Lys Glu Leu Ser Pro
                100                 105                 110

Pro Gln Ile Ser Ala Glu Val Leu Arg Lys Met Lys Glu Ala Ala Glu
            115                 120                 125

Ala Tyr Leu Gly Glu Lys Val Thr Glu Ala Val Ile Thr Val Pro Ala
130                 135                 140

Tyr Phe Asn Asp Ser Gln Arg Gln Ala Thr Lys Asp Ala Gly Arg Ile
145                 150                 155                 160

Ala Gly Leu Asp Val Lys Arg Ile Ile Asn Glu Pro Thr Ala Ala Ala
                165                 170                 175

Leu Ala Phe Gly Met Asp Lys Gly Asp Asn Lys Asp Arg Lys Val Ala
            180                 185                 190

Val Tyr Asp Leu Gly Gly Gly Thr Phe Asp Ile Ser Ile Ile Glu Ile
        195                 200                 205

Ala Asn Leu Asp Gly Asp Lys Gln Phe Glu Val Leu Ala Thr Asn Gly
210                 215                 220

Asp Thr Phe Leu Gly Gly Glu Asp Phe Asp Gln Arg Leu Ile Asp His
225                 230                 235                 240

Ile Ile Ala Glu Phe Lys Lys Glu Gln Gly Ile Asp Leu Lys Gln Asp
                245                 250                 255

Val Met Ala Leu Gln Arg Leu Lys Glu Ala Ala Glu Lys Ala Lys Ile
            260                 265                 270

Glu Leu Ser Ser Gly Gln Gln Thr Glu Ile Asn Leu Pro Tyr Ile Thr
        275                 280                 285

Met Asp Ala Thr Gly Pro Lys His Leu Ala Met Lys Ile Thr Arg Ala
    290                 295                 300

Lys Phe Glu Ser Leu Val Glu Asp Leu Ile Thr Arg Ser Ile Glu Pro
305                 310                 315                 320

Cys Lys Ile Ala Leu Lys Asp Ala Gly Leu Ser Thr Gly Asp Ile Asp
                325                 330                 335
```

-continued

```
Asp Val Ile Leu Val Gly Gly Gln Ser Arg Met Pro Lys Val Gln Glu
            340                 345                 350

Ala Val Lys Ala Phe Phe Gly Lys Glu Pro Arg Lys Asp Val Asn Pro
            355                 360                 365

Asp Glu Ala Val Ala Val Gly Ala Ala Ile Gln Gly Glu Val Leu Ser
            370                 375                 380

Gly Gly Arg Ser Asp Val Leu Leu Asp Val Thr Pro Leu Ser Leu
385                 390                 395                 400

Gly Ile Glu Thr Met Gly Gly Val Met Thr Lys Leu Ile Gln Lys Asn
            405                 410                 415

Thr Thr Ile Pro Thr Lys Ala Ser Gln Val Phe Ser Thr Ala Glu Asp
            420                 425                 430

Asn Gln Ser Ala Val Thr Ile His Val Leu Gln Gly Glu Arg Glu Arg
            435                 440                 445

Ala Ser Ala Asn Lys Ser Leu Gly Gln Phe Asn Leu Gly Asp Ile Ala
            450                 455                 460

Pro Ala Pro Arg Gly Met Pro Gln Ile Glu Val Thr Phe Asp Ile Asp
465                 470                 475                 480

Ala Asn Gly Ile Leu His Val Ser Ala Lys Asp Lys Gly Thr Gly Lys
            485                 490                 495

Ala Ala Asn Ile Thr Ile Gln Gly Ser Ser Gly Leu Gly Glu Glu
            500                 505                 510

Ile Glu Arg Met Val Lys Asp Ala Glu Ala Asn Ala Glu Glu Asp Lys
            515                 520                 525

Lys Leu Thr Glu Leu Val Ala Ser Arg Asn Gln Ala Glu Ala Leu Ile
            530                 535                 540

His Ser Val Lys Lys Ser Leu Ala Asp Tyr Gly Asp Lys Leu Asp Ala
545                 550                 555                 560

Ala Glu Lys Glu Lys Ile Glu Ala Ala Leu Lys Glu Ala Glu Glu Ala
            565                 570                 575

Val Lys Gly Asp Asp Lys Ala Ala Ile Asp Ala Lys Thr Glu Ala Leu
            580                 585                 590

Gly Ala Ala Ser Gln Lys Leu Gly Glu Met Val Tyr Ala Gln Ala Gln
            595                 600                 605

Ala Glu Ala Gln Ala Gly Glu Ser Glu Gln Ala Asn Ala Ser Ala Lys
            610                 615                 620

Lys Asp Asp Asp Val Val Asp Ala Asp Phe Glu Glu Val Lys Asp Asp
625                 630                 635                 640

Lys Lys
```

<210> SEQ ID NO 14
<211> LENGTH: 562
<212> TYPE: PRT
<213> ORGANISM: Neisseria meningitidis

<400> SEQUENCE: 14

```
Glu Val Gln Arg Asp Ile Glu Ser Met Pro Phe Glu Ile Ile Lys Ala
  1                 5                  10                  15

Asn Asn Gly Asp Ala Trp Val Lys Ala Gln Gly Lys Glu Leu Ser Pro
            20                  25                  30

Pro Gln Ile Ser Ala Glu Val Leu Arg Lys Met Lys Glu Ala Ala Glu
            35                  40                  45

Ala Tyr Leu Gly Glu Lys Val Thr Glu Ala Val Ile Thr Val Pro Ala
            50                  55                  60
```

```
Tyr Phe Asn Asp Ser Gln Arg Gln Ala Thr Lys Asp Ala Gly Arg Ile
 65                  70                  75                  80

Ala Gly Leu Asp Val Lys Arg Ile Ile Asn Glu Pro Thr Ala Ala Ala
                 85                  90                  95

Leu Ala Phe Gly Met Asp Lys Gly Asp Asn Lys Asp Arg Lys Val Ala
            100                 105                 110

Val Tyr Asp Leu Gly Gly Gly Thr Phe Asp Ile Ser Ile Ile Glu Ile
        115                 120                 125

Ala Asn Leu Asp Gly Asp Lys Gln Phe Glu Val Leu Ala Thr Asn Gly
130                 135                 140

Asp Thr Phe Leu Gly Gly Glu Asp Phe Asp Gln Arg Leu Ile Asp His
145                 150                 155                 160

Ile Ile Ala Glu Phe Lys Lys Glu Gln Gly Ile Asp Leu Lys Gln Asp
                165                 170                 175

Val Met Ala Leu Gln Arg Leu Lys Glu Ala Ala Glu Lys Ala Lys Ile
            180                 185                 190

Glu Leu Ser Ser Gly Gln Gln Thr Glu Ile Asn Leu Pro Tyr Ile Thr
        195                 200                 205

Met Asp Ala Thr Gly Pro Lys His Leu Ala Met Lys Ile Thr Arg Ala
210                 215                 220

Lys Phe Glu Ser Leu Val Glu Asp Leu Ile Thr Arg Ser Ile Glu Pro
225                 230                 235                 240

Cys Lys Ile Ala Leu Lys Asp Ala Gly Leu Ser Thr Gly Asp Ile Asp
                245                 250                 255

Asp Val Ile Leu Val Gly Gly Gln Ser Arg Met Pro Lys Val Gln Glu
            260                 265                 270

Ala Val Lys Ala Phe Phe Gly Lys Glu Pro Arg Lys Asp Val Asn Pro
        275                 280                 285

Asp Glu Ala Val Ala Val Gly Ala Ala Ile Gln Gly Glu Val Leu Ser
290                 295                 300

Gly Gly Arg Ser Asp Val Leu Leu Leu Asp Val Thr Pro Leu Ser Leu
305                 310                 315                 320

Gly Ile Glu Thr Met Gly Gly Val Met Thr Lys Leu Ile Gln Lys Asn
                325                 330                 335

Thr Thr Ile Pro Thr Lys Ala Ser Gln Val Phe Ser Thr Ala Glu Asp
            340                 345                 350

Asn Gln Ser Ala Val Thr Ile His Val Leu Gln Gly Glu Arg Glu Arg
        355                 360                 365

Ala Ser Ala Asn Lys Ser Leu Gly Gln Phe Asn Leu Gly Asp Ile Ala
370                 375                 380

Pro Ala Pro Arg Gly Met Pro Gln Ile Glu Val Thr Phe Asp Ile Asp
385                 390                 395                 400

Ala Asn Gly Ile Leu His Val Ser Ala Lys Asp Lys Gly Thr Gly Lys
                405                 410                 415

Ala Ala Asn Ile Thr Ile Gln Gly Ser Ser Gly Leu Ser Glu Glu Glu
            420                 425                 430

Ile Glu Arg Met Val Lys Asp Ala Glu Ala Asn Ala Glu Glu Asp Lys
        435                 440                 445

Lys Leu Thr Glu Leu Val Ala Ser Arg Asn Gln Ala Glu Ala Leu Ile
450                 455                 460

His Ser Val Lys Lys Ser Leu Ala Asp Tyr Gly Asp Lys Leu Asp Ala
465                 470                 475                 480
```

```
Ala Glu Lys Glu Lys Ile Glu Ala Ala Leu Lys Glu Ala Glu Ala
            485                 490                 495

Val Lys Gly Asp Asp Lys Ala Ala Ile Asp Ala Lys Thr Glu Ala Leu
        500                 505                 510

Gly Ala Ala Ser Gln Lys Leu Gly Glu Met Val Tyr Ala Gln Ala Gln
            515                 520                 525

Ala Glu Ala Gln Ala Gly Glu Ser Glu Gln Ala Asn Ala Ser Ala Lys
        530                 535                 540

Lys Asp Asp Val Val Asp Ala Asp Phe Glu Glu Val Lys Asp Asp
545                 550                 555                 560

Lys Lys

<210> SEQ ID NO 15
<211> LENGTH: 642
<212> TYPE: PRT
<213> ORGANISM: Neisseria meningitidis

<400> SEQUENCE: 15

Met Ala Lys Val Ile Gly Ile Asp Leu Gly Thr Thr Asn Ser Cys Leu
 1                5                  10                  15

Ala Ile Ser Glu Asn Gly Gln Thr Lys Val Ile Glu Asn Ala Glu Gly
            20                  25                  30

Ala Arg Thr Thr Pro Ser Val Ile Ala Tyr Leu Asp Gly Gly Glu Ile
        35                  40                  45

Leu Val Gly Ala Pro Ala Lys Arg Gln Ala Val Thr Asn Ala Lys Asn
    50                  55                  60

Thr Ile Tyr Ala Ala Lys Arg Leu Ile Gly His Lys Phe Glu Asp Lys
65                  70                  75                  80

Glu Val Gln Arg Asp Ile Glu Ser Met Pro Phe Glu Ile Ile Lys Ala
                85                  90                  95

Asn Asn Gly Asp Ala Trp Val Lys Ala Gln Gly Lys Glu Leu Ser Pro
            100                 105                 110

Pro Gln Ile Ser Ala Glu Val Leu Arg Lys Met Lys Glu Ala Ala Glu
        115                 120                 125

Ala Tyr Leu Gly Glu Lys Val Thr Glu Ala Val Ile Thr Val Pro Ala
    130                 135                 140

Tyr Phe Asn Asp Ser Gln Arg Gln Ala Thr Lys Asp Ala Gly Arg Ile
145                 150                 155                 160

Ala Gly Leu Asp Val Lys Arg Ile Ile Asn Glu Pro Thr Ala Ala Ala
                165                 170                 175

Leu Ala Phe Gly Met Asp Lys Gly Asp Asn Lys Asp Arg Lys Val Ala
            180                 185                 190

Val Tyr Asp Leu Gly Gly Gly Thr Phe Asp Ile Ser Ile Ile Glu Ile
        195                 200                 205

Ala Asn Leu Asp Gly Asp Lys Gln Phe Glu Val Leu Ala Thr Asn Gly
    210                 215                 220

Asp Thr Phe Leu Gly Gly Glu Asp Phe Asp Gln Arg Leu Ile Asp His
225                 230                 235                 240

Ile Ile Ala Glu Phe Lys Lys Glu Gln Gly Ile Asp Leu Lys Gln Asp
                245                 250                 255

Val Met Ala Leu Gln Arg Leu Lys Glu Ala Ala Glu Lys Ala Lys Ile
            260                 265                 270

Glu Leu Ser Ser Gly Gln Gln Thr Glu Ile Asn Leu Pro Tyr Ile Thr
        275                 280                 285
```

```
Met Asp Ala Thr Gly Pro Lys His Leu Ala Met Lys Ile Thr Arg Ala
    290                 295                 300

Lys Phe Glu Ser Leu Val Glu Asp Leu Ile Thr Arg Ser Ile Glu Pro
305                 310                 315                 320

Cys Lys Ile Ala Leu Lys Asp Ala Gly Leu Ser Thr Gly Asp Ile Asp
                325                 330                 335

Asp Val Ile Leu Val Gly Gly Gln Ser Arg Met Pro Lys Val Gln Glu
            340                 345                 350

Ala Val Lys Ala Phe Phe Gly Lys Glu Pro Arg Lys Asp Val Asn Pro
        355                 360                 365

Asp Glu Ala Val Ala Val Gly Ala Ala Ile Gln Gly Glu Val Leu Ser
    370                 375                 380

Gly Gly Arg Ser Asp Val Leu Leu Leu Asp Val Thr Pro Leu Ser Leu
385                 390                 395                 400

Gly Ile Glu Thr Met Gly Gly Val Met Thr Lys Leu Ile Gln Lys Asn
                405                 410                 415

Thr Thr Ile Pro Thr Lys Ala Ser Gln Val Phe Ser Thr Ala Glu Asp
            420                 425                 430

Asn Gln Ser Ala Val Thr Ile His Val Leu Gln Gly Glu Arg Glu Arg
        435                 440                 445

Ala Ser Ala Asn Lys Ser Leu Gly Gln Phe Asn Leu Gly Asp Ile Ala
    450                 455                 460

Pro Ala Pro Arg Gly Met Pro Gln Ile Glu Val Thr Phe Asp Ile Asp
465                 470                 475                 480

Ala Asn Gly Ile Leu His Val Ser Ala Lys Asp Lys Gly Thr Gly Lys
                485                 490                 495

Ala Ala Asn Ile Thr Ile Gln Gly Ser Ser Gly Leu Ser Glu Glu Glu
            500                 505                 510

Ile Glu Arg Met Val Lys Asp Ala Glu Ala Asn Ala Glu Glu Asp Lys
        515                 520                 525

Lys Leu Thr Glu Leu Val Ala Ser Arg Asn Gln Ala Glu Ala Leu Ile
    530                 535                 540

His Ser Val Lys Lys Ser Leu Ala Asp Tyr Gly Asp Lys Leu Asp Ala
545                 550                 555                 560

Ala Glu Lys Glu Lys Ile Glu Ala Ala Leu Lys Glu Ala Glu Glu Ala
                565                 570                 575

Val Lys Gly Asp Asp Lys Ala Ala Ile Asp Ala Lys Thr Glu Ala Leu
            580                 585                 590

Gly Ala Ala Ser Gln Lys Leu Gly Glu Met Val Tyr Ala Gln Ala Gln
        595                 600                 605

Ala Glu Ala Gln Ala Gly Glu Ser Gln Ala Asn Ala Ser Ala Lys
    610                 615                 620

Lys Asp Asp Asp Val Val Asp Ala Asp Phe Glu Glu Val Lys Asp Asp
625                 630                 635                 640

Lys Lys

<210> SEQ ID NO 16
<211> LENGTH: 662
<212> TYPE: PRT
<213> ORGANISM: Neisseria meningitidis

<400> SEQUENCE: 16

Met Gly Ser Ser His His His His His His Ser Ser Gly Leu Val Pro
1               5                   10                  15
```

-continued

Arg Gly Ser His Met Ala Lys Val Ile Gly Ile Asp Leu Gly Thr Thr
                20                  25                  30
Asn Ser Cys Leu Ala Ile Ser Glu Asn Gly Gln Thr Lys Val Ile Glu
            35                  40                  45
Asn Ala Glu Gly Ala Arg Thr Thr Pro Ser Val Ile Ala Tyr Leu Asp
50                  55                  60
Gly Gly Glu Ile Leu Val Gly Ala Pro Ala Lys Arg Gln Ala Val Thr
65                  70                  75                  80
Asn Ala Lys Asn Thr Ile Tyr Ala Ala Lys Arg Leu Ile Gly His Lys
                85                  90                  95
Phe Glu Asp Lys Glu Val Gln Arg Asp Ile Glu Ser Met Pro Phe Glu
            100                 105                 110
Ile Ile Lys Ala Asn Asn Gly Asp Ala Trp Val Lys Ala Gln Gly Lys
        115                 120                 125
Glu Leu Ser Pro Pro Gln Ile Ser Ala Glu Val Leu Arg Lys Met Lys
    130                 135                 140
Glu Ala Glu Ala Tyr Leu Gly Glu Lys Val Thr Glu Ala Val Ile
145                 150                 155                 160
Thr Val Pro Ala Tyr Phe Asn Asp Ser Gln Arg Gln Ala Thr Lys Asp
                165                 170                 175
Ala Gly Arg Ile Ala Gly Leu Asp Val Lys Arg Ile Ile Asn Glu Pro
            180                 185                 190
Thr Ala Ala Ala Leu Ala Phe Gly Met Asp Lys Gly Asp Asn Lys Asp
        195                 200                 205
Arg Lys Val Ala Val Tyr Asp Leu Gly Gly Gly Thr Phe Asp Ile Ser
    210                 215                 220
Ile Ile Glu Ile Ala Asn Leu Asp Gly Asp Lys Gln Phe Glu Val Leu
225                 230                 235                 240
Ala Thr Asn Gly Asp Thr Phe Leu Gly Gly Glu Asp Phe Asp Gln Arg
                245                 250                 255
Leu Ile Asp His Ile Ile Ala Glu Phe Lys Lys Glu Gln Gly Ile Asp
            260                 265                 270
Leu Lys Gln Asp Val Met Ala Leu Gln Arg Leu Lys Glu Ala Ala Glu
    275                 280                 285
Lys Ala Lys Ile Glu Leu Ser Ser Gly Gln Gln Thr Glu Ile Asn Leu
290                 295                 300
Pro Tyr Ile Thr Met Asp Ala Thr Gly Pro Lys His Leu Ala Met Lys
305                 310                 315                 320
Ile Thr Arg Ala Lys Phe Glu Ser Leu Val Glu Asp Leu Ile Thr Arg
                325                 330                 335
Ser Ile Glu Pro Cys Lys Ile Ala Leu Lys Asp Ala Gly Leu Ser Thr
            340                 345                 350
Gly Asp Ile Asp Asp Val Ile Leu Val Gly Gly Gln Ser Arg Met Pro
        355                 360                 365
Lys Val Gln Glu Ala Val Lys Ala Phe Phe Gly Lys Glu Pro Arg Lys
    370                 375                 380
Asp Val Asn Pro Asp Glu Ala Val Ala Val Gly Ala Ala Ile Gln Gly
385                 390                 395                 400
Glu Val Leu Ser Gly Gly Arg Ser Asp Val Leu Leu Leu Asp Val Thr
                405                 410                 415
Pro Leu Ser Leu Gly Ile Glu Thr Met Gly Gly Val Met Thr Lys Leu
            420                 425                 430
Ile Gln Lys Asn Thr Thr Ile Pro Thr Lys Ala Ser Gln Val Phe Ser

-continued

```
                435                 440                 445
Thr Ala Glu Asp Asn Gln Ser Ala Val Thr Ile His Val Leu Gln Gly
            450                 455                 460
Glu Arg Glu Arg Ala Ser Ala Asn Lys Ser Leu Gly Gln Phe Asn Leu
465                 470                 475                 480
Gly Asp Ile Ala Pro Ala Pro Arg Gly Met Pro Gln Ile Glu Val Thr
                485                 490                 495
Phe Asp Ile Asp Ala Asn Gly Ile Leu His Val Ser Ala Lys Asp Lys
                500                 505                 510
Gly Thr Gly Lys Ala Ala Asn Ile Thr Ile Gln Gly Ser Ser Gly Leu
            515                 520                 525
Ser Glu Glu Ile Glu Arg Met Val Lys Asp Ala Glu Ala Asn Ala
        530                 535                 540
Glu Glu Asp Lys Lys Leu Thr Glu Leu Val Ala Ser Arg Asn Gln Ala
545                 550                 555                 560
Glu Ala Leu Ile His Ser Val Lys Lys Ser Leu Ala Asp Tyr Gly Asp
                565                 570                 575
Lys Leu Asp Ala Ala Glu Lys Glu Lys Ile Glu Ala Ala Leu Lys Glu
            580                 585                 590
Ala Glu Glu Ala Val Lys Gly Asp Asp Lys Ala Ala Ile Asp Ala Lys
        595                 600                 605
Thr Glu Ala Leu Gly Ala Ala Ser Gln Lys Leu Gly Glu Met Val Tyr
        610                 615                 620
Ala Gln Ala Gln Ala Glu Ala Gln Ala Gly Glu Ser Glu Gln Ala Asn
625                 630                 635                 640
Ala Ser Ala Lys Lys Asp Asp Asp Val Val Asp Ala Asp Phe Glu Glu
                645                 650                 655
Val Lys Asp Asp Lys Lys
            660

<210> SEQ ID NO 17
<211> LENGTH: 37
<212> TYPE: PRT
<213> ORGANISM: aspergillus fumigatus

<400> SEQUENCE: 17

Met Gln Arg Ala Leu Ser Ser Arg Thr Ser Val Leu Ser Ala Ser
1               5                   10                  15
Lys Arg Ala Ala Phe Thr Lys Pro Ala Gly Leu Asn Leu Gln Gln Gln
            20                  25                  30
Arg Phe Ala His Lys
        35

<210> SEQ ID NO 18
<211> LENGTH: 48
<212> TYPE: PRT
<213> ORGANISM: aspergillus fumigatus

<400> SEQUENCE: 18

Glu Leu Lys Phe Gly Val Glu Ala Arg Ala Gln Leu Leu Lys Gly Val
1               5                   10                  15
Asp Thr Leu Ala Lys Ala Val Thr Ser Thr Leu Gly Pro Lys Gly Arg
            20                  25                  30
Asn Val Leu Ile Glu Ser Pro Tyr Gly Ser Pro Lys Ile Thr Lys Asp
            35                  40                  45
```

-continued

```
<210> SEQ ID NO 19
<211> LENGTH: 502
<212> TYPE: PRT
<213> ORGANISM: aspergillus fumigatus

<400> SEQUENCE: 19
```

| | | | | | | | | | | | | | | | |
|---|---|---|---|---|---|---|---|---|---|---|---|---|---|---|---|
| Gly | Val | Ser | Val | Ala | Lys | Ala | Ile | Thr | Leu | Gln | Asp | Lys | Phe | Glu | Asn |
| 1 | | | | 5 | | | | | 10 | | | | | 15 | |
| Leu | Gly | Ala | Arg | Leu | Leu | Gln | Asp | Val | Ala | Ser | Lys | Thr | Asn | Glu | Ile |
| | | | 20 | | | | | 25 | | | | | 30 | | |
| Ala | Gly | Asp | Gly | Thr | Thr | Thr | Ala | Thr | Val | Leu | Ala | Arg | Ala | Ile | Phe |
| | | 35 | | | | | 40 | | | | | 45 | | | |
| Ser | Glu | Thr | Val | Lys | Asn | Val | Ala | Ala | Gly | Cys | Asn | Pro | Met | Asp | Leu |
| | 50 | | | | | 55 | | | | | 60 | | | | |
| Arg | Arg | Gly | Ile | Gln | Ala | Ala | Val | Asp | Ala | Val | Val | Asp | Tyr | Leu | Gln |
| 65 | | | | | 70 | | | | | 75 | | | | | 80 |
| Lys | Asn | Lys | Arg | Asp | Ile | Thr | Thr | Gly | Glu | Glu | Ile | Ala | Gln | Val | Ala |
| | | | | 85 | | | | | 90 | | | | | 95 | |
| Thr | Ile | Ser | Ala | Asn | Gly | Asp | Thr | His | Ile | Gly | Lys | Leu | Ile | Ser | Thr |
| | | | | 100 | | | | | 105 | | | | | 110 | |
| Ala | Met | Glu | Arg | Val | Gly | Lys | Glu | Gly | Val | Ile | Thr | Val | Lys | Glu | Gly |
| | | | 115 | | | | | 120 | | | | | 125 | | |
| Lys | Thr | Ile | Glu | Asp | Glu | Leu | Glu | Val | Thr | Glu | Gly | Met | Arg | Phe | Asp |
| | 130 | | | | | 135 | | | | | 140 | | | | |
| Arg | Gly | Tyr | Thr | Ser | Pro | Tyr | Phe | Ile | Thr | Asp | Thr | Lys | Ser | Gln | Lys |
| 145 | | | | | 150 | | | | | 155 | | | | | 160 |
| Val | Glu | Phe | Glu | Lys | Pro | Leu | Ile | Leu | Leu | Ser | Glu | Lys | Lys | Ile | Ser |
| | | | | 165 | | | | | 170 | | | | | 175 | |
| Ala | Val | Gln | Asp | Ile | Ile | Pro | Ala | Leu | Glu | Ala | Ser | Thr | Thr | Leu | Arg |
| | | | 180 | | | | | 185 | | | | | 190 | | |
| Arg | Pro | Leu | Val | Ile | Ile | Ala | Glu | Asp | Ile | Glu | Gly | Glu | Ala | Leu | Ala |
| | | 195 | | | | | 200 | | | | | 205 | | | |
| Val | Cys | Ile | Leu | Asn | Lys | Leu | Arg | Gly | Gln | Leu | Gln | Val | Ala | Ala | Val |
| | 210 | | | | | 215 | | | | | 220 | | | | |
| Lys | Ala | Pro | Gly | Phe | Gly | Asp | Asn | Arg | Lys | Ser | Ile | Leu | Gly | Asp | Leu |
| 225 | | | | | 230 | | | | | 235 | | | | | 240 |
| Ala | Val | Leu | Thr | Asn | Gly | Thr | Val | Phe | Thr | Asp | Glu | Leu | Asp | Ile | Lys |
| | | | | 245 | | | | | 250 | | | | | 255 | |
| Leu | Glu | Lys | Leu | Thr | Pro | Asp | Met | Leu | Gly | Ser | Thr | Gly | Ala | Ile | Thr |
| | | | 260 | | | | | 265 | | | | | 270 | | |
| Ile | Thr | Lys | Glu | Asp | Thr | Ile | Ile | Leu | Asn | Gly | Glu | Gly | Ser | Lys | Asp |
| | 275 | | | | | 280 | | | | | 285 | | | | |
| Ala | Ile | Ala | Gln | Arg | Cys | Glu | Gln | Ile | Arg | Gly | Val | Met | Ala | Asp | Pro |
| 290 | | | | | 295 | | | | | 300 | | | | | |
| Ser | Thr | Ser | Glu | Tyr | Glu | Lys | Glu | Lys | Leu | Gln | Glu | Arg | Leu | Ala | Lys |
| 305 | | | | | 310 | | | | | 315 | | | | | 320 |
| Leu | Ser | Gly | Gly | Val | Ala | Val | Ile | Lys | Val | Gly | Gly | Ala | Ser | Glu | Val |
| | | | | 325 | | | | | 330 | | | | | 335 | |
| Glu | Val | Gly | Glu | Lys | Lys | Asp | Arg | Val | Val | Asp | Ala | Leu | Asn | Ala | Thr |
| | | | 340 | | | | | 345 | | | | | 350 | | |
| Arg | Ala | Ala | Val | Glu | Glu | Gly | Ile | Leu | Pro | Gly | Gly | Thr | Ala | Leu |
| | | 355 | | | | | 360 | | | | | 365 | | | |
| Leu | Lys | Ala | Ala | Ala | Asn | Gly | Leu | Asp | Asn | Val | Lys | Pro | Glu | Asn | Phe |
| | 370 | | | | | 375 | | | | | 380 | | | | |

-continued

```
Asp Gln Gln Leu Gly Val Ser Ile Ile Lys Asn Ala Ile Thr Arg Pro
385                 390                 395                 400

Ala Arg Thr Ile Val Glu Asn Ala Gly Leu Glu Gly Ser Val Ile Val
            405                 410                 415

Gly Lys Leu Thr Asp Glu Phe Ala Lys Asp Phe Asn Arg Gly Phe Asp
                420                 425                 430

Ser Ser Lys Gly Glu Tyr Val Asp Met Ile Ser Ser Gly Ile Leu Asp
            435                 440                 445

Pro Leu Lys Val Val Arg Thr Ala Leu Leu Asp Ala Ser Gly Val Ala
        450                 455                 460

Ser Leu Gly Thr Thr Glu Val Ala Ile Val Glu Ala Pro Glu Glu
465                 470                 475                 480

Lys Gly Pro Ala Ala Pro Gly Met Gly Gly Met Gly Gly Met Gly Gly
                485                 490                 495

Met Gly Gly Gly Met Phe
            500

<210> SEQ ID NO 20
<211> LENGTH: 550
<212> TYPE: PRT
<213> ORGANISM: aspergillus fumigatus

<400> SEQUENCE: 20

Met Lys Glu Leu Lys Phe Gly Val Glu Ala Arg Ala Gln Leu Leu Lys
1               5                   10                  15

Gly Val Asp Thr Leu Ala Lys Ala Val Thr Ser Thr Leu Gly Pro Lys
            20                  25                  30

Gly Arg Asn Val Leu Ile Glu Ser Pro Tyr Gly Ser Pro Lys Ile Thr
        35                  40                  45

Lys Asp Gly Val Ser Val Ala Lys Ala Ile Thr Leu Gln Asp Lys Phe
    50                  55                  60

Glu Asn Leu Gly Ala Arg Leu Leu Gln Asp Val Ala Ser Lys Thr Asn
65                  70                  75                  80

Glu Ile Ala Gly Asp Gly Thr Thr Thr Ala Thr Val Leu Ala Arg Ala
                85                  90                  95

Ile Phe Ser Glu Thr Val Lys Asn Val Ala Ala Gly Cys Asn Pro Met
            100                 105                 110

Asp Leu Arg Arg Gly Ile Gln Ala Ala Val Asp Ala Val Val Asp Tyr
        115                 120                 125

Leu Gln Lys Asn Lys Arg Asp Ile Thr Thr Gly Glu Glu Ile Ala Gln
    130                 135                 140

Val Ala Thr Ile Ser Ala Asn Gly Asp Thr His Ile Gly Lys Leu Ile
145                 150                 155                 160

Ser Thr Ala Met Glu Arg Val Gly Lys Glu Gly Val Ile Thr Val Lys
                165                 170                 175

Glu Gly Lys Thr Ile Glu Asp Glu Leu Glu Val Thr Glu Gly Met Arg
            180                 185                 190

Phe Asp Arg Gly Tyr Thr Ser Pro Tyr Phe Ile Thr Asp Thr Lys Ser
        195                 200                 205

Gln Lys Val Glu Phe Glu Lys Pro Leu Ile Leu Leu Ser Glu Lys Lys
    210                 215                 220

Ile Ser Ala Val Gln Asp Ile Ile Pro Ala Leu Glu Ala Ser Thr Thr
225                 230                 235                 240

Leu Arg Arg Pro Leu Val Ile Ile Ala Glu Asp Ile Glu Gly Glu Ala
                245                 250                 255
```

```
Leu Ala Val Cys Ile Leu Asn Lys Leu Arg Gly Gln Leu Gln Val Ala
                260                 265                 270

Ala Val Lys Ala Pro Gly Phe Gly Asp Asn Arg Lys Ser Ile Leu Gly
            275                 280                 285

Asp Leu Ala Val Leu Thr Asn Gly Thr Val Phe Thr Asp Glu Leu Asp
        290                 295                 300

Ile Lys Leu Glu Lys Leu Thr Pro Asp Met Leu Gly Ser Thr Gly Ala
305                 310                 315                 320

Ile Thr Ile Thr Lys Glu Asp Thr Ile Ile Leu Asn Gly Glu Gly Ser
                325                 330                 335

Lys Asp Ala Ile Ala Gln Arg Cys Glu Gln Ile Arg Gly Val Met Ala
            340                 345                 350

Asp Pro Ser Thr Ser Glu Tyr Glu Lys Glu Lys Leu Gln Glu Arg Leu
        355                 360                 365

Ala Lys Leu Ser Gly Gly Val Ala Val Ile Lys Val Gly Gly Ala Ser
    370                 375                 380

Glu Val Glu Val Gly Glu Lys Lys Asp Arg Val Val Asp Ala Leu Asn
385                 390                 395                 400

Ala Thr Arg Ala Ala Val Glu Glu Gly Ile Leu Pro Gly Gly Gly Thr
                405                 410                 415

Ala Leu Leu Lys Ala Ala Ala Asn Gly Leu Asp Asn Val Lys Pro Glu
            420                 425                 430

Asn Phe Asp Gln Gln Leu Gly Val Ser Ile Ile Lys Asn Ala Ile Thr
        435                 440                 445

Arg Pro Ala Arg Thr Ile Val Glu Asn Ala Gly Leu Glu Gly Ser Val
    450                 455                 460

Ile Val Gly Lys Leu Thr Asp Glu Phe Ala Lys Asp Phe Asn Arg Gly
465                 470                 475                 480

Phe Asp Ser Ser Lys Gly Glu Tyr Val Asp Met Ile Ser Ser Gly Ile
                485                 490                 495

Leu Asp Pro Leu Lys Val Val Arg Thr Ala Leu Leu Asp Ala Ser Gly
            500                 505                 510

Val Ala Ser Leu Leu Gly Thr Thr Glu Val Ala Ile Val Glu Ala Pro
        515                 520                 525

Glu Glu Lys Gly Pro Ala Ala Pro Gly Met Gly Gly Met Gly Gly Met
    530                 535                 540

Gly Gly Met Gly Gly Met
545                 550

<210> SEQ ID NO 21
<211> LENGTH: 570
<212> TYPE: PRT
<213> ORGANISM: aspergillus fumigatus

<400> SEQUENCE: 21

Met Gly Ser Ser His His His His His His Ser Ser Gly Leu Val Pro
  1               5                  10                  15

Arg Gly Ser His Met Lys Glu Leu Lys Phe Gly Val Glu Ala Arg Ala
                20                  25                  30

Gln Leu Leu Lys Gly Val Asp Thr Leu Ala Lys Ala Val Thr Ser Thr
            35                  40                  45

Leu Gly Pro Lys Gly Arg Asn Val Leu Ile Glu Ser Pro Tyr Gly Ser
        50                  55                  60

Pro Lys Ile Thr Lys Asp Gly Val Ser Val Ala Lys Ala Ile Thr Leu
```

-continued

```
 65                  70                  75                  80

Gln Asp Lys Phe Glu Asn Leu Gly Ala Arg Leu Leu Gln Asp Val Ala
                 85                  90                  95

Ser Lys Thr Asn Glu Ile Ala Gly Asp Gly Thr Thr Thr Ala Thr Val
                100                 105                 110

Leu Ala Arg Ala Ile Phe Ser Glu Thr Val Lys Asn Val Ala Ala Gly
            115                 120                 125

Cys Asn Pro Met Asp Leu Arg Arg Gly Ile Gln Ala Ala Val Asp Ala
130                 135                 140

Val Val Asp Tyr Leu Gln Lys Asn Lys Arg Asp Ile Thr Thr Gly Glu
145                 150                 155                 160

Glu Ile Ala Gln Val Ala Thr Ile Ser Ala Asn Gly Asp Thr His Ile
                165                 170                 175

Gly Lys Leu Ile Ser Thr Ala Met Glu Arg Val Gly Lys Glu Gly Val
                180                 185                 190

Ile Thr Val Lys Glu Gly Lys Thr Ile Glu Asp Glu Leu Glu Val Thr
            195                 200                 205

Glu Gly Met Arg Phe Asp Arg Gly Tyr Thr Ser Pro Tyr Phe Ile Thr
210                 215                 220

Asp Thr Lys Ser Gln Lys Val Glu Phe Glu Lys Pro Leu Ile Leu Leu
225                 230                 235                 240

Ser Glu Lys Lys Ile Ser Ala Val Gln Asp Ile Ile Pro Ala Leu Glu
                245                 250                 255

Ala Ser Thr Thr Leu Arg Arg Pro Leu Val Ile Ile Ala Glu Asp Ile
                260                 265                 270

Glu Gly Glu Ala Leu Ala Val Cys Ile Leu Asn Lys Leu Arg Gly Gln
            275                 280                 285

Leu Gln Val Ala Ala Val Lys Ala Pro Gly Phe Gly Asp Asn Arg Lys
290                 295                 300

Ser Ile Leu Gly Asp Leu Ala Val Leu Thr Asn Gly Thr Val Phe Thr
305                 310                 315                 320

Asp Glu Leu Asp Ile Lys Leu Glu Lys Leu Thr Pro Asp Met Leu Gly
                325                 330                 335

Ser Thr Gly Ala Ile Thr Ile Thr Lys Glu Asp Thr Ile Ile Leu Asn
                340                 345                 350

Gly Glu Gly Ser Lys Asp Ala Ile Ala Gln Arg Cys Glu Gln Ile Arg
            355                 360                 365

Gly Val Met Ala Asp Pro Ser Thr Ser Glu Tyr Glu Lys Glu Lys Leu
370                 375                 380

Gln Glu Arg Leu Ala Lys Leu Ser Gly Gly Val Ala Val Ile Lys Val
385                 390                 395                 400

Gly Gly Ala Ser Glu Val Glu Val Gly Glu Lys Lys Asp Arg Val Val
                405                 410                 415

Asp Ala Leu Asn Ala Thr Arg Ala Ala Val Glu Glu Gly Ile Leu Pro
                420                 425                 430

Gly Gly Gly Thr Ala Leu Leu Lys Ala Ala Ala Asn Gly Leu Asp Asn
            435                 440                 445

Val Lys Pro Glu Asn Phe Asp Gln Gln Leu Gly Val Ser Ile Ile Lys
450                 455                 460

Asn Ala Ile Thr Arg Pro Ala Arg Thr Ile Val Glu Asn Ala Gly Leu
465                 470                 475                 480

Glu Gly Ser Val Ile Val Gly Lys Leu Thr Asp Glu Phe Ala Lys Asp
                485                 490                 495
```

-continued

```
Phe Asn Arg Gly Phe Asp Ser Ser Lys Gly Glu Tyr Val Asp Met Ile
            500                 505                 510
Ser Ser Gly Ile Leu Asp Pro Leu Lys Val Val Arg Thr Ala Leu Leu
            515                 520                 525
Asp Ala Ser Gly Val Ala Ser Leu Leu Gly Thr Thr Glu Val Ala Ile
            530                 535                 540
Val Glu Ala Pro Glu Glu Lys Gly Pro Ala Ala Pro Gly Met Gly Gly
545                 550                 555                 560
Met Gly Gly Met Gly Gly Met Gly Gly Met
                565                 570

<210> SEQ ID NO 22
<211> LENGTH: 568
<212> TYPE: PRT
<213> ORGANISM: Candida glabrata

<400> SEQUENCE: 22

Met Leu Arg Ala Val Ala Arg Ser Gln Val Arg Ser Leu Arg Asn Ala
1               5                   10                  15
Arg Leu Tyr Ser Ser Phe Lys Glu Leu Lys Phe Gly Val Glu Gly Arg
            20                  25                  30
Ala Ala Leu Leu Arg Gly Val Glu Thr Leu Ala Asp Ala Val Ser Ala
            35                  40                  45
Thr Leu Gly Pro Lys Gly Arg Asn Val Leu Ile Glu Gln Pro Phe Gly
    50                  55                  60
Ala Pro Lys Ile Thr Lys Asp Gly Val Thr Val Ala Arg Ser Ile Thr
65                  70                  75                  80
Leu Glu Asp Lys Phe Glu Asn Met Gly Ala Lys Leu Leu Gln Glu Val
                85                  90                  95
Ala Ser Lys Thr Asn Glu Ala Ala Gly Asp Gly Thr Thr Ser Ala Thr
            100                 105                 110
Val Leu Gly Arg Ala Ile Phe Thr Glu Ser Val Lys Asn Val Ala Ala
            115                 120                 125
Gly Cys Asn Pro Met Asp Leu Arg Arg Gly Ser Gln Ala Ala Val Glu
    130                 135                 140
Lys Val Ile Gln Phe Leu Thr Glu Asn Lys Lys Glu Ile Thr Thr Ser
145                 150                 155                 160
Glu Glu Ile Ala Gln Val Ala Thr Ile Ser Ala Asn Gly Asp Ala His
                165                 170                 175
Val Gly Lys Leu Leu Ala Ser Ala Met Glu Lys Val Gly Lys Glu Gly
            180                 185                 190
Val Ile Thr Ile Arg Glu Gly Arg Thr Leu Glu Asp Glu Leu Glu Val
            195                 200                 205
Thr Glu Gly Met Arg Phe Asp Arg Gly Phe Ile Ser Pro Tyr Phe Ile
    210                 215                 220
Thr Asp Ala Lys Ser Gly Lys Val Glu Phe Glu Lys Pro Leu Leu Leu
225                 230                 235                 240
Leu Ser Glu Lys Lys Ile Ser Ser Ile Gln Asp Ile Leu Pro Ala Leu
                245                 250                 255
Glu Leu Ser Asn Gln Ser Arg Arg Pro Leu Leu Ile Ile Ala Glu Asp
            260                 265                 270
Val Asp Gly Glu Ala Leu Ala Ala Cys Ile Leu Asn Lys Leu Arg Gly
            275                 280                 285
Gln Val Lys Val Cys Ala Val Lys Ala Pro Gly Phe Gly Asp Asn Arg
```

-continued

```
            290                 295                 300
Lys Asn Ile Leu Gly Asp Val Ala Ile Leu Thr Gly Ser Thr Val Phe
305                 310                 315                 320

Thr Glu Glu Leu Asp Leu Lys Pro Glu Gln Ala Thr Met Glu His Leu
                325                 330                 335

Gly Ser Cys Asp Ser Ile Thr Ile Thr Lys Glu Asp Thr Val Ile Leu
            340                 345                 350

Asn Gly Asn Gly Ser Lys Asp Ser Ile Gln Glu Arg Ile Glu Gln Ile
        355                 360                 365

Lys Asn Ser Ile Asp Val Thr Thr Asn Ser Tyr Glu Lys Glu Lys
370                 375                 380

Leu Gln Glu Arg Leu Ala Lys Leu Ser Gly Val Ala Val Ile Arg
385                 390                 395                 400

Val Gly Gly Ala Ser Glu Val Glu Val Gly Glu Lys Lys Asp Arg Tyr
                405                 410                 415

Asp Asp Ala Leu Asn Ala Thr Arg Ala Ala Val Glu Glu Gly Ile Leu
            420                 425                 430

Pro Gly Gly Gly Thr Ala Leu Val Lys Ala Ser Arg Val Leu Asp Glu
        435                 440                 445

Val Lys Thr Glu Asn Phe Asp Gln Lys Leu Gly Val Asp Ile Ile Arg
450                 455                 460

Lys Ala Ile Thr Arg Pro Ala Lys Gln Ile Ile Glu Asn Ala Gly Glu
465                 470                 475                 480

Glu Gly Ser Val Ile Val Gly Lys Leu Val Asp Glu Phe Gly Glu Asp
                485                 490                 495

Phe Ala Lys Gly Tyr Asp Ser Ala Lys Gly Glu Phe Thr Asp Met Leu
            500                 505                 510

Ala Ala Gly Ile Ile Asp Pro Phe Lys Val Val Arg Ser Gly Leu Val
        515                 520                 525

Asp Ala Ser Gly Val Ala Ser Leu Leu Ala Thr Thr Glu Val Ala Ile
530                 535                 540

Val Asp Ala Pro Glu Pro Ala Pro Ala Ala Gly Ala Pro Gly Gly Gly
545                 550                 555                 560

Met Pro Gly Met Pro Gly Met Met
                565
```

<210> SEQ ID NO 23
<211> LENGTH: 548
<212> TYPE: PRT
<213> ORGANISM: Candida glabrata

<400> SEQUENCE: 23

```
Met Ala Lys Glu Leu Lys Phe Gly Val Glu Gly Arg Ala Ala Leu Leu
 1               5                  10                  15

Arg Gly Val Glu Thr Leu Ala Asp Ala Val Ser Ala Thr Leu Gly Pro
                20                  25                  30

Lys Gly Arg Asn Val Leu Ile Glu Gln Pro Phe Gly Ala Pro Lys Ile
            35                  40                  45

Thr Lys Asp Gly Val Thr Val Ala Arg Ser Ile Thr Leu Glu Asp Lys
        50                  55                  60

Phe Glu Asn Met Gly Ala Lys Leu Leu Gln Glu Val Ala Ser Lys Thr
65                  70                  75                  80

Asn Glu Ala Ala Gly Asp Gly Thr Thr Ser Ala Thr Val Leu Gly Arg
                85                  90                  95
```

```
Ala Ile Phe Thr Glu Ser Val Lys Asn Val Ala Ala Gly Cys Asn Pro
            100                 105                 110

Met Asp Leu Arg Arg Gly Ser Gln Ala Ala Val Glu Lys Val Ile Gln
            115                 120                 125

Phe Leu Thr Glu Asn Lys Lys Glu Ile Thr Thr Ser Glu Glu Ile Ala
            130                 135                 140

Gln Val Ala Thr Ile Ser Ala Asn Gly Asp Ala His Val Gly Lys Leu
145                 150                 155                 160

Leu Ala Ser Ala Met Glu Lys Val Gly Lys Glu Gly Val Ile Thr Ile
                165                 170                 175

Arg Glu Gly Arg Thr Leu Glu Asp Glu Leu Glu Val Thr Glu Gly Met
                180                 185                 190

Arg Phe Asp Arg Gly Phe Ile Ser Pro Tyr Phe Ile Thr Asp Ala Lys
            195                 200                 205

Ser Gly Lys Val Glu Phe Glu Lys Pro Leu Leu Leu Ser Glu Lys
            210                 215                 220

Lys Ile Ser Ser Ile Gln Asp Ile Leu Pro Ala Leu Glu Leu Ser Asn
225                 230                 235                 240

Gln Ser Arg Arg Pro Leu Leu Ile Ile Ala Glu Asp Val Asp Gly Glu
                245                 250                 255

Ala Leu Ala Ala Cys Ile Leu Asn Lys Leu Arg Gly Gln Val Lys Val
            260                 265                 270

Cys Ala Val Lys Ala Pro Gly Phe Gly Asp Asn Arg Lys Asn Ile Leu
            275                 280                 285

Gly Asp Val Ala Ile Leu Thr Gly Ser Thr Val Phe Thr Glu Glu Leu
            290                 295                 300

Asp Leu Lys Pro Glu Gln Ala Thr Met Glu His Leu Gly Ser Cys Asp
305                 310                 315                 320

Ser Ile Thr Ile Thr Lys Glu Asp Thr Val Ile Leu Asn Gly Asn Gly
                325                 330                 335

Ser Lys Asp Ser Ile Gln Glu Arg Ile Glu Gln Ile Lys Asn Ser Ile
                340                 345                 350

Asp Val Thr Thr Thr Asn Ser Tyr Glu Lys Glu Lys Leu Gln Glu Arg
                355                 360                 365

Leu Ala Lys Leu Ser Gly Gly Val Ala Val Ile Arg Val Gly Gly Ala
            370                 375                 380

Ser Glu Val Glu Val Gly Glu Lys Lys Asp Arg Tyr Asp Asp Ala Leu
385                 390                 395                 400

Asn Ala Thr Arg Ala Ala Val Glu Glu Gly Ile Leu Pro Gly Gly Gly
                405                 410                 415

Thr Ala Leu Val Lys Ala Ser Arg Val Leu Asp Glu Val Lys Thr Glu
                420                 425                 430

Asn Phe Asp Gln Lys Leu Gly Val Asp Ile Ile Arg Lys Ala Ile Thr
            435                 440                 445

Arg Pro Ala Lys Gln Ile Ile Glu Asn Ala Gly Glu Glu Gly Ser Val
450                 455                 460

Ile Val Gly Lys Leu Val Asp Glu Phe Gly Glu Asp Phe Ala Lys Gly
465                 470                 475                 480

Tyr Asp Ser Ala Lys Gly Glu Phe Thr Asp Met Leu Ala Ala Gly Ile
                485                 490                 495

Ile Asp Pro Phe Lys Val Val Arg Ser Gly Leu Val Asp Ala Ser Gly
            500                 505                 510

Val Ala Ser Leu Leu Ala Thr Thr Glu Val Ala Ile Val Asp Ala Pro
```

```
                515                 520                 525
Glu Pro Ala Pro Ala Gly Ala Pro Gly Gly Met Pro Gly Met
    530                 535                 540
Pro Gly Met Met
545

<210> SEQ ID NO 24
<211> LENGTH: 568
<212> TYPE: PRT
<213> ORGANISM: Candida glabrata

<400> SEQUENCE: 24

Met Gly Ser Ser His His His His His His Ser Gly Leu Val Pro
1               5                   10                  15

Arg Gly Ser His Met Ala Lys Glu Leu Lys Phe Gly Val Glu Gly Arg
            20                  25                  30

Ala Ala Leu Leu Arg Gly Val Glu Thr Leu Ala Asp Ala Val Ser Ala
            35                  40                  45

Thr Leu Gly Pro Lys Gly Arg Asn Val Leu Ile Glu Gln Pro Phe Gly
    50                  55                  60

Ala Pro Lys Ile Thr Lys Asp Gly Val Thr Val Ala Arg Ser Ile Thr
65                  70                  75                  80

Leu Glu Asp Lys Phe Glu Asn Met Gly Ala Lys Leu Leu Gln Glu Val
                85                  90                  95

Ala Ser Lys Thr Asn Glu Ala Ala Gly Asp Gly Thr Thr Ser Ala Thr
            100                 105                 110

Val Leu Gly Arg Ala Ile Phe Thr Glu Ser Val Lys Asn Val Ala Ala
            115                 120                 125

Gly Cys Asn Pro Met Asp Leu Arg Arg Gly Ser Gln Ala Ala Val Glu
130                 135                 140

Lys Val Ile Gln Phe Leu Thr Glu Asn Lys Lys Glu Ile Thr Thr Ser
145                 150                 155                 160

Glu Glu Ile Ala Gln Val Ala Thr Ile Ser Ala Asn Gly Asp Ala His
                165                 170                 175

Val Gly Lys Leu Leu Ala Ser Ala Met Glu Lys Val Gly Lys Glu Gly
            180                 185                 190

Val Ile Thr Ile Arg Glu Gly Arg Thr Leu Glu Asp Glu Leu Glu Val
            195                 200                 205

Thr Glu Gly Met Arg Phe Asp Arg Gly Phe Ile Ser Pro Tyr Phe Ile
    210                 215                 220

Thr Asp Ala Lys Ser Gly Lys Val Glu Phe Glu Lys Pro Leu Leu Leu
225                 230                 235                 240

Leu Ser Glu Lys Lys Ile Ser Ser Ile Gln Asp Ile Leu Pro Ala Leu
                245                 250                 255

Glu Leu Ser Asn Gln Ser Arg Arg Pro Leu Leu Ile Ile Ala Glu Asp
            260                 265                 270

Val Asp Gly Glu Ala Leu Ala Ala Cys Ile Leu Asn Lys Leu Arg Gly
            275                 280                 285

Gln Val Lys Val Cys Ala Val Lys Ala Pro Gly Phe Gly Asp Asn Arg
    290                 295                 300

Lys Asn Ile Leu Gly Asp Val Ala Ile Leu Thr Gly Ser Thr Val Phe
305                 310                 315                 320

Thr Glu Glu Leu Asp Leu Lys Pro Glu Gln Ala Thr Met Glu His Leu
                325                 330                 335
```

-continued

```
Gly Ser Cys Asp Ser Ile Thr Ile Thr Lys Glu Asp Thr Val Ile Leu
            340                 345                 350
Asn Gly Asn Gly Ser Lys Asp Ser Ile Gln Glu Arg Ile Glu Gln Ile
        355                 360                 365

Lys Asn Ser Ile Asp Val Thr Thr Thr Asn Ser Tyr Glu Lys Glu Lys
    370                 375                 380

Leu Gln Glu Arg Leu Ala Lys Leu Ser Gly Gly Val Ala Val Ile Arg
385                 390                 395                 400

Val Gly Gly Ala Ser Glu Val Glu Val Gly Glu Lys Lys Asp Arg Tyr
                405                 410                 415

Asp Asp Ala Leu Asn Ala Thr Arg Ala Ala Val Glu Glu Gly Ile Leu
            420                 425                 430
Pro Gly Gly Gly Thr Ala Leu Val Lys Ala Ser Arg Val Leu Asp Glu
        435                 440                 445

Val Lys Thr Glu Asn Phe Asp Gln Lys Leu Gly Val Asp Ile Ile Arg
    450                 455                 460

Lys Ala Ile Thr Arg Pro Ala Lys Gln Ile Ile Glu Asn Ala Gly Glu
465                 470                 475                 480
Glu Gly Ser Val Ile Val Gly Lys Leu Val Asp Glu Phe Gly Glu Asp
                485                 490                 495

Phe Ala Lys Gly Tyr Asp Ser Ala Lys Gly Glu Phe Thr Asp Met Leu
            500                 505                 510
Ala Ala Gly Ile Ile Asp Pro Phe Lys Val Val Arg Ser Gly Leu Val
        515                 520                 525

Asp Ala Ser Gly Val Ala Ser Leu Leu Ala Thr Thr Glu Val Ala Ile
    530                 535                 540

Val Asp Ala Pro Glu Pro Ala Pro Ala Ala Gly Ala Pro Gly Gly Gly
545                 550                 555                 560
Met Pro Gly Met Pro Gly Met Met
                565
```

<210> SEQ ID NO 25
<211> LENGTH: 19
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors

<400> SEQUENCE: 25
ctgccgtaca tcaccatgg 19

<210> SEQ ID NO 26
<211> LENGTH: 19
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors

<400> SEQUENCE: 26
ggcttcttgt actttcggc 19

<210> SEQ ID NO 27
<211> LENGTH: 18
<212> TYPE: DNA
<213> ORGANISM: Artificial Sequence
<220> FEATURE:

-continued

<223> OTHER INFORMATION: Primer Used to clone Neisseria meningitidis Hsp70 gene and to contruct Neisseria meningitidis Hsp70 expression vectors

<400> SEQUENCE: 27
tgaccttgtt gaacgtac 18

<210> SEQ ID NO 28
<211> LENGTH: 17
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors

<400> SEQUENCE: 28
acttcatcag ggtttac 17

<210> SEQ ID NO 29
<211> LENGTH: 6
<212> TYPE: PRT
<213> ORGANISM: Neisseria meningitidis

<400> SEQUENCE: 29

Pro Ala Tyr Phe Asn Asp
1 5

<210> SEQ ID NO 30
<211> LENGTH: 18
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors
<220> FEATURE:
<221> NAME/KEY: misc_feature
<222> LOCATION: (1)...(18)
<223> OTHER INFORMATION: n = A,T,C or G

<400> SEQUENCE: 30
ccngcntayt tyaaygay 18

<210> SEQ ID NO 31
<211> LENGTH: 7
<212> TYPE: PRT
<213> ORGANISM: Neisseria meningitidis

<400> SEQUENCE: 31

Pro Gln Ile Glu Val Thr Phe
1 5

<210> SEQ ID NO 32
<211> LENGTH: 21
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors
<220> FEATURE:
<221> NAME/KEY: misc_feature
<222> LOCATION: (1)...(21)
<223> OTHER INFORMATION: n = A,T,C or G

<400> SEQUENCE: 32
raangtnacy tcdatytgng g 21

<210> SEQ ID NO 33
<211> LENGTH: 16
<212> TYPE: DNA
<213> ORGANISM: Artificial Sequence
<220> FEATURE:
<223> OTHER INFORMATION: Primer Used to clone Neisseria meningitidis
      Hsp70 gene and to contruct Neisseria meningitidis Hsp70 expression
      vectors

<400> SEQUENCE: 33
gtaaaacgac ggccag 16

<210> SEQ ID NO 34
<211> LENGTH: 17
<212> TYPE: DNA
<213> ORGANISM: Artificial Sequence
<220> FEATURE:
<223> OTHER INFORMATION: Primer Used to clone Neisseria meningitidis
Hsp70 gene and to contruct Neisseria meningitidis Hsp70 expression
vectors

<400> SEQUENCE: 34
caggaaacag ctatgac 17

<210> SEQ ID NO 35
<211> LENGTH: 27
<212> TYPE: DNA
<213> ORGANISM: Artificial Sequence
<220> FEATURE:
<223> OTHER INFORMATION: Primer Used to clone Neisseria meningitidis
Hsp70 gene and to contruct Neisseria meningitidis Hsp70 expression
vectors

<400> SEQUENCE: 35
ggtcggctcg ttgatgatgc gtttcac 27

<210> SEQ ID NO 36
<211> LENGTH: 27
<212> TYPE: DNA
<213> ORGANISM: Artificial Sequence
<220> FEATURE:
<223> OTHER INFORMATION: Primer Used to clone Neisseria meningitidis
Hsp70 gene and to contruct Neisseria meningitidis Hsp70 expression
vectors

<400> SEQUENCE: 36
gcttctgcca acaaatcttt gggtcag 27

<210> SEQ ID NO 37
<211> LENGTH: 24
<212> TYPE: DNA
<213> ORGANISM: Artificial Sequence
<220> FEATURE:
<223> OTHER INFORMATION: Primer Used to clone Neisseria meningitidis
Hsp70 gene and to contruct Neisseria meningitidis Hsp70 expression
vectors

<400> SEQUENCE: 37
gccgctttgg cattcgttat ggac 24

<210> SEQ ID NO 38
<211> LENGTH: 24
<212> TYPE: DNA
<213> ORGANISM: Artificial Sequence
<220> FEATURE:
<223> OTHER INFORMATION: Primer Used to clone Neisseria meningitidis
Hsp70 gene and to contruct Neisseria meningitidis Hsp70 expression vectors

<400> SEQUENCE: 38
gcgttcgcgt tcgccttgca gtac                                              24

<210> SEQ ID NO 39
<211> LENGTH: 18
<212> TYPE: DNA
<213> ORGANISM: Artificial Sequence
<220> FEATURE:
<223> OTHER INFORMATION: Primer Used to clone Neisseria meningitidis
     Hsp70 gene and to construct Neisseria meningitidis Hsp70 expression
     vectors

<400> SEQUENCE: 39
ttccgaaaac ggtcaaac                                                     18

<210> SEQ ID NO 40
<211> LENGTH: 18
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors

<400> SEQUENCE: 40
atggccaaac aagagttg 18

<210> SEQ ID NO 41
<211> LENGTH: 26
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors

<400> SEQUENCE: 41
tacatatggc aaaagtaatc ggtatc 26

<210> SEQ ID NO 42
<211> LENGTH: 22
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors

<400> SEQUENCE: 42
tttatttttt gtcgtctttt ac 22

<210> SEQ ID NO 43
<211> LENGTH: 19
<212> TYPE: DNA
<213> ORGANISM: Artificial Sequence
<220> FEATURE:
<223> OTHER INFORMATION: Primer Used to clone Neisseria meningitidis Hsp70 gene and to contruct Neisseria meningitidis Hsp70 expression vectors

<400> SEQUENCE: 43
gtccaaataa gcgataacg 19

<210> SEQ ID NO 44
<211> LENGTH: 18

```
<212> TYPE: DNA
<213> ORGANISM: Artificial Sequence
<220> FEATURE:
<223> OTHER INFORMATION: Primer Used to clone Neisseria meningitidis
      Hsp70 gene and to contruct Neisseria meningitidis Hsp70 expression
      vectors

<400> SEQUENCE: 44
gccgccaaac gtttgatc                                              18

<210> SEQ ID NO 45
<211> LENGTH: 18
<212> TYPE: DNA
<213> ORGANISM: Artificial Sequence
<220> FEATURE:
<223> OTHER INFORMATION: Primer Used to clone Neisseria meningitidis
      Hsp70 gene and to contruct Neisseria meningitidis Hsp70 expression
      vectors

<400> SEQUENCE: 45
accatgggcg gcgtgatg                                              18

<210> SEQ ID NO 46
<211> LENGTH: 18
<212> TYPE: DNA
<213> ORGANISM: Artificial Sequence
<220> FEATURE:
<223> OTHER INFORMATION: Primer Used to clone Neisseria meningitidis
      Hsp70 gene and to contruct Neisseria meningitidis Hsp70 expression
      vectors

<400> SEQUENCE: 46
gaagccaatg ccgaggaa                                              18

<210> SEQ ID NO 47
<211> LENGTH: 18
<212> TYPE: DNA
<213> ORGANISM: Artificial Sequence
<220> FEATURE:
<223> OTHER INFORMATION: Primer Used to clone Neisseria meningitidis
      Hsp70 gene and to contruct Neisseria meningitidis Hsp70 expression
      vectors

<400> SEQUENCE: 47
tgcgtcgccg ttgttggc                                              18

<210> SEQ ID NO 48
<211> LENGTH: 18
<212> TYPE: DNA
<213> ORGANISM: Artificial Sequence
<220> FEATURE:
<223> OTHER INFORMATION: Primer Used to clone Neisseria meningitidis
      Hsp70 gene and to contruct Neisseria meningitidis Hsp70 expression
      vectors

<400> SEQUENCE: 48
ggtatcgccg ttggttgc                                              18

<210> SEQ ID NO 49
<211> LENGTH: 18
<212> TYPE: DNA
<213> ORGANISM: Artificial Sequence
<220> FEATURE:
<223> OTHER INFORMATION: Primer Used to clone Neisseria meningitidis
      Hsp70 gene and to contruct Neisseria meningitidis Hsp70 expression
      vectors

<400> SEQUENCE: 49
```

```
gagtttgtcg ccgtagtc                                              18
```

<210> SEQ ID NO 50
<211> LENGTH: 27
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
<220> FEATURE:
<221> NAME/KEY: misc_feature
<222> LOCATION: (1)...(27)
<223> OTHER INFORMATION: n = A,T,C or G

<400> SEQUENCE: 50

```
ccatatgaar ganytnaart tyggngt                                    27
```

<210> SEQ ID NO 51
<211> LENGTH: 20
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
<220> FEATURE:
<221> NAME/KEY: modified_base
<222> LOCATION: (3)...(3)
<223> OTHER INFORMATION: I
<220> FEATURE:
<221> NAME/KEY: modified_base
<222> LOCATION: (6)...(6)
<223> OTHER INFORMATION: I
<220> FEATURE:
<221> NAME/KEY: modified_base
<222> LOCATION: (9)...(9)
<223> OTHER INFORMATION: I
<220> FEATURE:
<221> NAME/KEY: modified_base
<222> LOCATION: (12)...(12)
<223> OTHER INFORMATION: I
<220> FEATURE:
<221> NAME/KEY: modified_base
<222> LOCATION: (18)...(18)
<223> OTHER INFORMATION: I

<400> SEQUENCE: 51

```
aanganttna antttggngt                                            20
```

<210> SEQ ID NO 52
<211> LENGTH: 22
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
<220> FEATURE:
<221> NAME/KEY: misc_feature
<222> LOCATION: (1)...(22)
<223> OTHER INFORMATION: n = A,T,C or G

<400> SEQUENCE: 52

```
cttacatcat nccnggcatn cc                                         22
```

<210> SEQ ID NO 53
<211> LENGTH: 19
<212> TYPE: DNA
<213> ORGANISM: Artificial Sequence
<220> FEATURE:
<223> OTHER INFORMATION: Primer Used to clone Aspergillus fumigatus Hsp60 gene and to contruct Aspergillus fumigatus Hsp60 expression
        plasmids
<220> FEATURE:
<221> NAME/KEY: modified_base
<222> LOCATION: (8)...(8)
<223> OTHER INFORMATION: I
<220> FEATURE:
<221> NAME/KEY: modified_base
<222> LOCATION: (11)...(11)
<223> OTHER INFORMATION: I
<220> FEATURE:
<221> NAME/KEY: modified_base
<222> LOCATION: (17)...(17)
<223> OTHER INFORMATION: I

<400> SEQUENCE: 53
acatcatncc nggcatncc                                                    19

<210> SEQ ID NO 54
<211> LENGTH: 25
<212> TYPE: DNA
<213> ORGANISM: Artificial Sequence
<220> FEATURE:
<223> OTHER INFORMATION: Primer Used to clone Aspergillus fumigatus
        Hsp60 gene and to contruct Aspergillus fumigatus Hsp60 expression
        plasmids
<220> FEATURE:
<221> NAME/KEY: misc_feature
<222> LOCATION: (1)...(25)
<223> OTHER INFORMATION: n = A,T,C or G

<400> SEQUENCE: 54
cttacatncc ncccatnccn cccat                                             25

<210> SEQ ID NO 55
<211> LENGTH: 18
<212> TYPE: DNA
<213> ORGANISM: Artificial Sequence
<220> FEATURE:
<223> OTHER INFORMATION: Primer Used to clone Aspergillus fumigatus
        Hsp60 gene and to contruct Aspergillus fumigatus Hsp60 expression
        plasmids
<220> FEATURE:
<221> NAME/KEY: modified_base
<222> LOCATION: (4)...(4)
<223> OTHER INFORMATION: I
<220> FEATURE:
<221> NAME/KEY: modified_base
<222> LOCATION: (7)...(7)
<223> OTHER INFORMATION: I
<220> FEATURE:
<221> NAME/KEY: modified_base
<222> LOCATION: (13)...(13)
<223> OTHER INFORMATION: I
<220> FEATURE:
<221> NAME/KEY: modified_base
<222> LOCATION: (16)...(16)
<223> OTHER INFORMATION: I

<400> SEQUENCE: 55 catncnccc atnccncc                                                      18

<210> SEQ ID NO 56
<211> LENGTH: 20
<212> TYPE: DNA
<213> ORGANISM: Artificial Sequence
<220> FEATURE:
<223> OTHER INFORMATION: Primer Used to clone Aspergillus fumigatus
        Hsp60 gene and to contruct Aspergillus fumigatus Hsp60 expression
        plasmids
<220> FEATURE:
<221> NAME/KEY: modified_base
<222> LOCATION: (3)...(3)

```
<223> OTHER INFORMATION: I
<220> FEATURE:
<221> NAME/KEY: modified_base
<222> LOCATION: (6)...(6)
<223> OTHER INFORMATION: I
<220> FEATURE:
<221> NAME/KEY: modified_base
<222> LOCATION: (12)...(12)
<223> OTHER INFORMATION: I
<220> FEATURE:
<221> NAME/KEY: modified_base
<222> LOCATION: (15)...(15)
<223> OTHER INFORMATION: I
<220> FEATURE:
<221> NAME/KEY: modified_base
<222> LOCATION: (18)...(18)
<223> OTHER INFORMATION: I

<400> SEQUENCE: 56
gcnggngayg gnacnacnac                                              20

<210> SEQ ID NO 57
<211> LENGTH: 23
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 57
ggwccmaagg ghmgwaatgt ytt                                          23

<210> SEQ ID NO 58
<211> LENGTH: 23
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
<220> FEATURE:
<221> NAME/KEY: misc_feature
<222> LOCATION: (1)...(23)
OTHER INFORMATION: n = A,T,C r G

<400> SEQUENCE: 58
ccnaaratya ctaaggaygg tgt                                          23

<210> SEQ ID NO 59
<211> LENGTH: 20
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
<220> FEATURE:
<221> NAME/KEY: misc_feature
<222> LOCATION: (1)...(20)
<223> OTHER INFORMATION: n = A,T,C or G

<400> SEQUENCE: 59
aarganttna aattyggygt                                              20

<210> SEQ ID NO 60
<211> LENGTH: 20
<212> TYPE: DNA
<213> ORGANISM: Artificial Sequence
<220> FEATURE:
<223> OTHER INFORMATION: Primer Used to clone Aspergillus fumigatus
```

Hsp60 gene and to contruct Aspergillus fumigatus Hsp60 expression
        plasmids
<220> FEATURE:
<221> NAME/KEY: misc_feature
<222> LOCATION: (1)...(20)
<223> OTHER INFORMATION: n = A,T,C or G

<400> SEQUENCE: 60
tccatnggrt trcanccngc                                                    20

<210> SEQ ID NO 61
<211> LENGTH: 20
<212> TYPE: DNA
<213> ORGANISM: Artificial Sequence
<220> FEATURE:
<223> OTHER INFORMATION: Primer Used to clone Aspergillus fumigatus
        Hsp60 gene and to contruct Aspergillus fumigatus Hsp60 expression
        plasmids
<220> FEATURE:
<221> NAME/KEY: misc_feature
<222> LOCATION: (1)...(20)
<223> OTHER INFORMATION: n = A,T,C or G

<400> SEQUENCE: 61
atnacnccyt cyttnccnac                                                    20

<210> SEQ ID NO 62
<211> LENGTH: 18
<212> TYPE: DNA
<213> ORGANISM: Artificial Sequence
<220> FEATURE:
<223> OTHER INFORMATION: Primer Used to clone Aspergillus fumigatus
        Hsp60 gene and to contruct Aspergillus fumigatus Hsp60 expression
        plasmids
<220> FEATURE:
<221> NAME/KEY: misc_feature
<222> LOCATION: (1)...(18)
<223> OTHER INFORMATION: n = A,T,C or G

<400> SEQUENCE: 62
catnccytcn gtnacytc                                                      18

<210> SEQ ID NO 63
<211> LENGTH: 23
<212> TYPE: DNA
<213> ORGANISM: Artificial Sequence
<220> FEATURE:
<223> OTHER INFORMATION: Primer Used to clone Aspergillus fumigatus
        Hsp60 gene and to contruct Aspergillus fumigatus Hsp60 expression
        plasmids

<400> SEQUENCE: 63
acygartgtg cyattgtyga tgc                                                23

<210> SEQ ID NO 64
LENGTH 23
<212> TYPE: DNA
<213> ORGANISM: Artificial Sequence
<220> FEATURE:
<223> OTHER INFORMATION: Primer Used to clone Aspergillus fumigatus
        Hsp60 gene and to contruct Aspergillus fumigatus Hsp60 expression
        plasmids

<400> SEQUENCE: 64
acygargttg cyattgtyga tgc                                                23

<210> SEQ ID NO 65
LENGTH 23
<212> TYPE: DNA

```
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 65
ttagttgatg cttctggtgt ygc                                          23

<210> SEQ ID NO 66
<211> LENGTH: 23
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 66
ttagttgatg ctagyggtgt ygc                                          23

<210> SEQ ID NO 67
<211> LENGTH: 20
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
<220> FEATURE:
<221> NAME/KEY: misc_feature
<222> LOCATION: (1)...(20)
<223> OTHER INFORMATION: n = A,T,C or G

<400> SEQUENCE: 67
garaargara arytncarga                                              20

<210> SEQ ID NO 68
<211> LENGTH: 20
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
<220> FEATURE:
<221> NAME/KEY: misc_feature
<222> LOCATION: (1)...(20)
<223> OTHER INFORMATION: n = A,T,C or G

<400> SEQUENCE: 68
gcngcngtng argarggnat                                              20

<210> SEQ ID NO 69
<211> LENGTH: 27
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 69
ttacatgccg cccatgccgc ccatacc                                      27

<210> SEQ ID NO 70
<211> LENGTH: 24
<212> TYPE: DNA
<213> ORGANISM: Artificial Sequence
```

```
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 70
ttacatcata cctggcatac ctgg                                            24

<210> SEQ ID NO 71
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 71
ccggtggtga tgtcacgc                                                   18

<210> SEQ ID NO 72
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 72
ttgatgacgg caacaccg                                                   18

<210> SEQ ID NO 73
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 73
aactcgtcgg tcagcttg                                                   18

<210> SEQ ID NO 74
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 74
agaacctcgg tgctcgcc                                                   18

<210> SEQ ID NO 75
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 75
cgccatggag cgtgttgg                                                   18
```

```
<210> SEQ ID NO 76
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 76
tgctgttgag gagggtat                                                18

<210> SEQ ID NO 77
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 77
atgatgtcct gaacggca                                                18

<210> SEQ ID NO 78
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 78
ctgggcgatc ttgccgtc                                                18

<210> SEQ ID NO 79
<211> LENGTH: 21
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 79
ggtcgtaacg tccttatcga g                                            21

<210> SEQ ID NO 80
<211> LENGTH: 20
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 80
agagtcgaag tcacggcctt                                              20

<210> SEQ ID NO 81
<211> LENGTH: 22
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids
```

<400> SEQUENCE: 81
cctcaacaat agcgacctca gt                                            22

<210> SEQ ID NO 82
<211> LENGTH: 18
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 82
ccccgctgct cctggcat                                                 18

<210> SEQ ID NO 83
<211> LENGTH: 19
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 83
tcgggcagta gtgttcatc                                                19

<210> SEQ ID NO 84
<211> LENGTH: 33
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 84
tttctcttct atccttggtg atcttagggg agc                                33

<210> SEQ ID NO 85
<211> LENGTH: 31
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 85
tttctcttca gatggtgtct ctgttgccaa g                                  31

<210> SEQ ID NO 86
<211> LENGTH: 27
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 86
ttggattcta catcatacct ggcatac                                       27

<210> SEQ ID NO 87
<211> LENGTH: 19
<212> TYPE: DNA

```
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 87
taatacgact cactatagg                                                19

<210> SEQ ID NO 88
<211> LENGTH: 19
<212> TYPE: DNA
<213> ORGANISM: Artificial Sequence
<220> FEATURE:
<223> OTHER INFORMATION: Primer Used to clone Aspergillus fumigatus
      Hsp60 gene and to contruct Aspergillus fumigatus Hsp60 expression
      plasmids

<400> SEQUENCE: 88
gctagttatt gctcagcgg                                                19

<210> SEQ ID NO 89
<211> LENGTH: 18
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 89
cctatggatt tgagaagg                                                 18

<210> SEQ ID NO 90
<211> LENGTH: 18
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 90
ctgataatgt caactccc                                                 18

<210> SEQ ID NO 91
<211> LENGTH: 19
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 91
gatctcttcc atccaagac                                                19

<210> SEQ ID NO 92
<211> LENGTH: 18
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 92
gtccttggag ccgttacc                                                 18

<210> SEQ ID NO 93
<211> LENGTH: 18
```

<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 93
ggtaacggct ccaaggac                                                 18

<210> SEQ ID NO 94
<211> LENGTH: 19
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 94
gtcttggatg gaagagatc                                                19

<210> SEQ ID NO 95
<211> LENGTH: 18
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 95
ccttctcaaa tccatagg                                                 18

<210> SEQ ID NO 96
<211> LENGTH: 18
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 96
gggagttgac attatcag                                                 18

<210> SEQ ID NO 97
<211> LENGTH: 24
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 97
gttgcttcct tgttggctac tacc                                          24

<210> SEQ ID NO 98
<211> LENGTH: 24
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 98
ccccagcgtg gcagagacag cgtc                                          24

<210> SEQ ID NO 99
<211> LENGTH: 24
<212> TYPE: DNA

-continued

```
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 99
gagaacatgg gtgctaagct tctg                                               24

<210> SEQ ID NO 100
<211> LENGTH: 22
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 100
cagctctgcc ttcgacaccg aa                                                 22

<210> SEQ ID NO 101
<211> LENGTH: 23
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 101
atcaccaagg atggtgtcac cgt                                                23

<210> SEQ ID NO 102
<211> LENGTH: 27
<212> TYPE: DNA
<213> ORGANISM: Artificial Sequence
<220> FEATURE:
<223> OTHER INFORMATION: Primer Used to clone Candida glabrata Hsp60
      gene and to contruct Candida glabrata Hsp60 expression plasmids

<400> SEQUENCE: 102
gatatacata tggccaagga gttgaag                                            27
```

HEAT SHOCK GENES AND PROTEINS FROM *NEISSERIA MENINGITIDIS*, *CANDIDA GLABRATA* AND *ASPERGILLUS FUMIGATUS*

TECHNICAL FIELD OF THE INVENTION

This invention relates to heat shock proteins of the Hsp60 family from *Candida glabrata* and *Aspergillus fumigatus* and a heat shock protein of the Hsp70 family from *Neisseria meningitidis*, including fragments thereof, and uses of such proteins and nucleic acid molecules encoding these proteins.

BACKGROUND OF THE INVENTION

Meningitis is an infection of the fluid of the spinal cord and the fluid that surrounds the brain. The disease is caused either by a viral or a bacterial infection. Viral meningitis is typically less severe than bacterial meningitis and resolves without specific treatment. In contrast, bacterial meningitis can be rather severe and can cause brain damage, hearing loss or learning disability. Symptoms of meningitis are high fever, headache and stiff neck. These symptoms may develop over a span of several hours, or may take 1–2 days. Other symptoms may be nausea, vomiting, discomfort looking into bright light, confusion or sleepiness. In young children, the classical symptoms may be absent or may not be easily detected, and the child may appear to be slow, inactive, irritable, vomiting or feeding poorly. As the disease progresses, seizures may occur.

Bacterial meningitis may be caused by *Haemophilus influenzae, Streptococcus pneumoniae* or *Neisseria meningitidis*. Because all children (in the U.S.) are now given a vaccine against *Haemophilus influenzae* in the course of their routine immunizations, meningitis due to this organism is now relatively uncommon. Thus, the major bacterial disease-causing agents are now *Streptococcus pneumoniae* and *Neisseria meningitidis*.

Early diagnosis and treatment are critically important. It must be determined whether symptoms are due to a viral or bacterial agents, and, if they are caused by a bacterial agent, which bacterium is involved. Present methods of diagnosis are relatively slow. They involve obtaining spinal fluid by performing a spinal tap. Bacteria are identified by cultivation of spinal fluid.

Bacterially-caused meningitis can be treated by antibiotics. However, it is critically important that treatment commence early in the course of the disease. Obviously, antibiotic therapy may be jeopardized by the development of antibiotic-resistant strains of disease-causing bacteria. Because of this concern, and also because of cost-benefit considerations, vaccination against the bacteria causing the disease would be preferable, at least in regions, in which the disease is endemic. As discussed before, U.S. children are routinely vaccinated against *Haemophilus influenzae,* but not against *Neisseria meningitidis* and *Streptococcus pneumoniae.* One such vaccine protects against four strains of *Neisseria meningitidis.* However, the vaccine appears not to be effective in children under 18 months of age. Similarly, a vaccine containing polysaccharide antigens for 14 of the 83 capsular types of *Streptococcus pneumoniae* was developed. The vaccine was found to be 57% effective in two large studies. As with the *Neisseria* vaccine, children under the age of two years do not appear to be protected by the vaccine. Thus, there is a need for improved vaccine against the latter two species of bacteria. The information provided here was obtained from publications by the Division of Bacterial and Mycotic Diseases of the National Center for Infectious Diseases, and the Centers for Disease Control and prevention, by Lonks and Medeiros, Antimicrobial Therapy 1 79:523–535, 1995, by Butler et al., JAMA 270:1826, 1993, and by Gotschlich et al., Antibodies in Human Diagnosis and Therapy 391–402 (Haber and Krause eds., 1977).

Aspergillosis is an opportunistic infection occurring in compromised individuals and is caused by molds of the genus Aspergillus, of which *Aspergillus fumigatus* is an important species. Aspergillus is ubiquitous and is distributed worldwide. Infection generally involves inhalation of fungal elements. Aspergillosis has several clinical manifestations, including colonization of the ear or the lungs, allergic pulmonary involvement, and invasive pulmonary and disseminated infections. The pulmonary invasive and disseminated forms of infections have a grave prognosis, including a high rate of mortality. Susceptible hosts include cancer patients, patients treated with immunosuppressive or cytotoxic drugs, and those otherwise debilitated such as AIDS patients, neutropenic cancer patients, or patients receiving adrenal corticosteroid drugs. Segal, Vaccines against Fungal Infections, CRC Crit. Rev. Microbiology 14:229, 1987. Rolston and Bodey, Infections in patients with cancer, Cancer Medicine (Holland et al. eds), 1997. The true incidence of aspergillosis is not known in the HIV/AIDS population, in part because the condition is frequently not diagnosed. However, it is clear that the incidence is increasing. Ampel has reported that more than 75 cases have been documented in the literature. Ampel, Emerging disease issues and fungal pathogens associated with HIV infection, Emerging Infectious Diseases 2:109–116, 1996. Aspergillosis has been reported to occur in 20–50% of patients with acute leukemia. It is noted that many cases of Aspergillus infection in cancer patients are not diagnosed until an autopsy is performed after death. Clearly, aspergillosis is becoming increasingly common among neutropenic patients and in cancer patients receiving corticosteroid drugs. Rolston and Bodey, supra. An article in 1992 by Bodey et al. reports on the incidence of fungal infections based on an international autopsy survey. Bodey et al., Fungal Infections In Cancer Patients, An International Autopsy Survey, Eur. J. Clin. Microbiol. Infect. Dis. 11:99–109, 1992. Countries included are Austria, Belgium, Canada, Germany, Italy, Japan, Netherlands and the UK. It was concluded that 25% of leukemia patients had fungal infections. Of these infected patients, 66% had candidiasis, and 34% aspergillosis. Estimates of rates of fungal infections in organ transplant patients as high as about 40% were published. Paya, Clin. Infect. Dis. 16:677–688, 1993. More than 80% of these infections were due to Candida and Aspergillus. As alluded to before, diagnosis of aspergillosis is not infrequently missed, and there is therefore a need for improved methods of diagnosis.

Candidiasis is a fungal infection caused by yeasts of the genus Candida. Among the more than 80 known species, only seven species appear to be pathogenic. The major disease-causing species is *Candida albicans.* Among the pathogenic species s also found *Candida glabrata,* formerly known as *Torulopsis glabrata.* Clinical manifestations of Candida infection range from superficial cutaneous infections to disseminated disease. Infections range from acute to chronic. They can involve skin and nails, the mucosal membranes of the mouth and vagina, and various internal organs such as the lungs, gastrointestinal tract, and circulatory and central nervous systems. Manifestations can be oral thrush, vaginitis, balanitis, diaper rash, chronic mucocutaneous conditions, bronchitis or pneumonia, meningitis, endocarditis, and septicemia. While the superficial forms of candidiasis have been well known since antiquity, the incidence of the disseminated forms has increased recently, presumably because of the extensive use of antibiotics, corticosteroids, cytotoxic drugs, organ transplantation and other complex surgical procedures. It is important to note that today the majority of systemic or invasive fungal infections are due to Candida species. Segal, supra. Stringer, Mass. High Tech. 14:3, 1997.

Mortality from systemic candidiasis remains high, in the order of 38–59%. The mainstay for treatment is amphotericin B, and an alternative is fluconazole. In a multicenter trial, amphotericin B was 79% effective, and fluconazole 70%. Note that *Candida glabrata* is resistant to fluconazole. Because mortality remains high, an effective vaccine against candidiasis to be used in high-risk populations would be desirable.

Since *Candida albicans* is the major cause of candidiasis, essentially all work relating to both diagnosis and vaccination concerned this particular species. Thus, it is not clear to what extent diagnostic procedures developed and vaccination approaches taken would also detect or protect against other species such as *Candida glabrata*.

Therefore, there is a need in the art to identify and isolate novel stress proteins and nucleic acids encoding the same from *Neisseria meningitidis, Candida glabrata* and *Aspergillus fumigatus,* which are useful in the detection, diagnosis and treatment of infections caused by these organisms.

SUMMARY OF THE INVENTION

The present invention provides methods and compositions comprising isolated nucleic acid molecules specific to *Neisseria meningitidis, Candida glabrata* and *Aspergillus fumigatus,* as well as vector constructs and isolated polypeptides specific to *Neisseria meningitidis, Candida glabrata* and *Aspergillus fumigatus.* Such compositions and methods are useful for the diagnosis of infection and for generating an immune response to the respective organisms.

Thus, in one aspect the present invention provides an isolated nucleic acid molecule encoding a *Neisseria meningitidis* Hsp70. In some embodiments, the isolated nucleotide molecule is selected from the group consisting of: (a) an isolated nucleic acid molecule comprising the sequence of SEQ ID NO:1 (FIG. 4); (b) an isolated nucleic acid molecule comprising the sequence of SEQ ID NO:1 from nucleotides 358–2286; (c) an isolated nucleic acid molecule comprising the sequence of SEQ ID NO:2 (FIG. 6) from nucleotides 4–1932; (d) an isolated nucleic acid molecule comprising the sequence of SEQ ID NO:3 (FIG. 8); (e) an isolated nucleic acid molecule comprising the sequence of SEQ ID NO:4 (FIG. 9); (f) an isolated nucleic acid molecule complementary to any one of the nucleotides of SEQ ID NOS: 1 to 4 set forth in (a) through (e), respectively.

In another aspect, the present invention provides an isolated nucleic acid molecule which is a variant of, or is substantially similar to, the Neisseria Hsp70 nucleotide molecules described above. In further aspects the present invention provides an isolated nucleic acid molecule comprising a nucleotide sequence that is identical to a segment of contiguous nucleotide bases comprising at least 25% of SEQ ID NOS: 1 to 4 or a complement thereof or an isolated nucleic acid molecule encoding Hsp70 comprising a nucleic acid sequence that encodes a polypeptide comprising any one of SEQ ID NOS: 2, 3, or 4 or a variant Hsp70 that is at least 95% homologous to a polypeptide according to any one of SEQ ID NOS: 2, 3, or 4.

In one embodiment, the present invention provides an isolated nucleic acid molecule as described above, the molecule encoding a polypeptide that is able to be selectively bound by an antibody specific for a *Neisseria meningitidis* Hsp70.

In still another aspect, the present invention provides an isolated nucleic acid molecule encoding at least 8 contiguous amino acids of a *Neisseria meningitis* Hsp70 polypeptide selected from amino acid residues of FIG. 6, wherein the encoded *Neisseria meningitidis* Hsp70 polypeptide is able to bind to a major histocompatibility complex.

In still further aspects the present invention provides an isolated *Neisseria meningitidis* Hsp70 polypeptide.

In some embodiments, the isolated Hsp70 polypeptide comprises the amino acid sequence of FIG. 6, or variants thereof, preferably wherein the polypeptide is able to be selectively bound by an antibody specific for a *Neisseria meningitidis* Hsp70. In further embodiments, the isolated Hsp70 polypeptide is fused to an additional polypeptide to create a fusion protein.

In still yet further aspects the present invention provides an isolated Hsp70 polypeptide comprising at least 8 contiguous amino acids selected from amino acid residues of FIG. 6, wherein the Hsp70 polypeptide is capable of binding to a major histocompatibility complex and eliciting or enhancing an immune response to *Neisseria meningitidis* in a human being.

In certain embodiments, the isolated Hsp70 polypeptide is derived by proteolytic cleavage or chemical synthesis, or is an expression product of a transformed host cell containing a nucleic acid molecule encoding the Hsp70 or portion thereof. In further certain embodiments, the isolated Hsp70 polypeptide comprises greater than 95% homology to the Hsp70 polypeptide of FIG. 6, and the isolated Hsp70 polypeptide is able to be selectively bound by an antibody specific for a *Neisseria meningitidis* Hsp70.

In still yet another aspect the present invention provides an isolated polypeptide wherein the polypeptide is an expression product of a transformed host cell containing one of the aforementioned nucleic acid molecules derived from Neisseria.

In still yet further aspects the present invention provides vectors comprising at least one of the aforementioned nucleic acid molecules derived from Neisseria. In certain embodiments, the vector is an expression vector comprising a promoter in operative linkage with the isolated nucleic acid molecule encoding the Hsp70 or portion thereof, preferably further comprising a selectable or identifiable marker and/or wherein the promoter is a constitutive or an inducible promoter. The present invention also provides host cells containing such vectors. In certain embodiments, the host cell is selected from the group consisting of a bacterial cell, a mammalian cell, a yeast cell, a plant cell and an insect cell.

In still yet other aspects the present invention provides compositions comprising a Neisseria Hsp70 polypeptide in combination with a pharmaceutically acceptable carrier or diluent. In certain embodiments, the composition is suitable for systemic administration, oral administration, intranasal administration or parenteral administration.

In yet other aspects the present invention provides methods for eliciting or enhancing an immune response in a mammal against Neisseria, comprising administering to the mammal in an amount effective to elicit or enhance the response, a Neisseria Hsp70 polypeptide in combination with a pharmaceutically acceptable carrier or diluent; methods for eliciting or enhancing an immune response in a mammal to a polypeptide comprising administering to the mammal a fusion protein containing sequences of the polypeptide fused to the Neisseria Hsp70 polypeptide in combination with a pharmaceutically acceptable carrier or diluent; and methods for eliciting or enhancing an immune response in a mammal against a target antigen comprising administering to the mammal the target antigen joined to a Neisseria Hsp70 polypeptide in combination with a pharmaceutically acceptable carrier or diluent.

In still another aspect, this invention provides PCR primers and probes for detecting DNA encoding a *Neisseria meningitidis*. Hsp70 that includes at least about 15 contiguous bases from any one of SEQ. ID NOS: 1–4, or to compliment thereof. In a related aspect, the invention provides a method for diagnosing the presence of a *Neisseria meningitidis* in a subject sample that includes the steps of obtaining a DNA fraction from the subject sample; and performing a PCR amplification of the DNA fraction using at least one PCR primer that includes at least about 15 contiguous bases from any one of SEQ. ID NOS: 1–4, or a compliment thereof.

The present invention also provides an isolated nucleic acid molecule encoding a *Aspergillus fumigatus* Hsp60. In some embodiments, the isolated nucleotide molecule is selected from the group consisting of: (a) an isolated nucleic acid molecule comprising the sequence of SEQ ID NO:5 (FIG. 14); (b) an isolated nucleic acid molecule comprising the sequence of SEQ ID NO:5 from nucleotides 300–2234; (c) an isolated nucleic acid molecule comprising the sequence of SEQ ID NO:5 from nucleotides 300–410, nucleotides 514–655 and nucleotides 724–2234; (d) an isolated nucleic acid molecule comprising the sequence of SEQ ID NO:6 (FIG. 16); (e) an isolated nucleic acid molecule comprising the sequence of SEQ ID NO:7 (FIG. 18); (f) an isolated nucleic acid molecule complementary to any one of the nucleotides of SEQ ID NOS: 5 to 7 set forth in (a) through (e), respectively.

In another aspect, the present invention provides an isolated nucleic acid molecule that is a variant of, or is substantially similar to, the Aspergillus Hsp60 nucleotide molecules described above. In further aspects, the present invention provides an isolated nucleic acid molecule comprising a nucleotide sequence that is identical to a segment of contiguous nucleotide bases comprising at least 25% of SEQ ID NOS: 5 to 7, or a complement thereof, or an isolated nucleic acid molecule encoding Hsp60 and comprising a nucleic acid sequence of any one of SEQ ID NOS: 5, 6 or 7 or a variant Hsp60 that is at least 95% homologous to a nucleic acid sequence comprising any one of SEQ ID NOS: 5, 6, or 7.

In one embodiment, the present invention provides an isolated nucleic acid molecule according as described above, the molecule encoding a polypeptide that is able to be selectively bound by an antibody specific for a *Aspergillus fumigatus* Hsp60.

In still another aspect in one aspect the present invention provides an isolated nucleic acid molecule encoding at least 8 contiguous amino acids of a *Aspergillus fumigatus* Hsp60 polypeptide selected from amino acid residues according to FIG. 14, wherein the encoded *Aspergillus fumigatus* Hsp60 polypeptide is able to bind to a major histocompatibility complex.

In still further aspects the present invention provides an isolated *Aspergillus fumigatus* Hsp60 polypeptide.

In some embodiments, the isolated Hsp60 polypeptide comprises the amino acid sequence of FIG. 14, or variants thereof, preferably wherein the polypeptide is able to be selectively bound by an antibody specific for a *Aspergillus fumigatus* Hsp60. In further embodiments, the isolated Hsp60 polypeptide is fused to an additional polypeptide to create a fusion protein.

In still yet further aspects the present invention provides an isolated Hsp60 polypeptide comprising at least 8 contiguous amino acids selected from amino acid residues according to FIG. 14, wherein the Hsp60 polypeptide is capable of binding to a major histocompatibility complex and eliciting or enhancing an immune response to *Aspergillus fumigatus* in a human being.

In certain embodiments, the isolated Hsp60 polypeptide is derived from proteolytic cleavage or chemical synthesis, or is an expression product of a transformed host cell containing a nucleic acid molecule encoding the Hsp60 or portion thereof. In certain further embodiments, the isolated Hsp60 polypeptide comprises greater than 95% homology to the Hsp60 polypeptide of FIG. 14, and the isolated Hsp60 polypeptide is able to be selectively bound by an antibody specific for a *Aspergillus fumigatus* Hsp60.

In still yet another aspect the present invention provides an isolated polypeptide wherein the polypeptide is an expression product of a transformed host cell containing at least one of the nucleic acid molecules derived from the aforementioned Aspergillus molecules.

In still yet further aspects the present invention provides vectors comprising at least one of the aforementioned nucleic acid molecules derived from Aspergillus. In certain embodiments, the vector is an expression vector comprising a promoter in operative linkage with the isolated nucleic acid molecule encoding the Hsp60 or portion thereof, preferably further comprising a selectable or identifiable marker and/or wherein the promoter is a constitutive or an inducible promoter. The present invention also provides host cells containing such vectors. In certain embodiments, the host cell is selected from the group consisting of a bacterial cell, a mammalian cell, a yeast cell, a plant cell and an insect cell.

In still yet other aspects the present invention provides compositions comprising an Aspergillus Hsp60 polypeptide in combination with a pharmaceutically acceptable carrier or diluent. In certain embodiments, the composition is suitable for systemic administration, oral administration, intranasal administration or parenteral administration.

In yet other aspects the present invention provides methods for eliciting or enhancing an immune response in a mammal against Aspergillus, comprising administering to the mammal in an amount effective to elicit or enhance the response, an Aspergilllus Hsp60 polypeptide in combination with a pharmaceutically acceptable carrier or diluent; methods for eliciting or enhancing an immune response in a mammal to a polypeptide comprising administering to the mammal a fusion protein containing sequences of the polypeptide fused to the Hsp60 polypeptide in combination with a pharmaceutically acceptable carrier or diluent; and methods for eliciting or enhancing an immune response in a mammal against a target antigen comprising administering to the mammal the target antigen joined to an Aspergillus Hsp60 polypeptide in combination with a pharmaceutically acceptable carrier or diluent.

In still another aspect, this invention provides PCR primers and probes for detecting DNA encoding a *Aspergillus fumigatus* Hsp60 that includes at least about 15 contiguous bases from any one of SEQ. ID NOS: 5–7, or to compliment thereof. In a related aspect, the invention provides a method for diagnosing the presence of a *Aspergillus fumigatus* in a subject sample that includes the steps of obtaining a DNA fraction from the subject sample; and performing a PCR amplification of the DNA fraction using at least one PCR primer that includes at least about 15 contiguous bases from any one of SEQ. ID NOS: 5–7, or a compliment thereof.

The present invention further provides an isolated nucleic acid molecule encoding a *Candida glabrata* Hsp60. In some embodiments, the isolated nucleotide molecule is selected from the group consisting of: (a) an isolated nucleic acid molecule comprising the sequence of SEQ ID NO:8 (FIG. 21); (b) an isolated nucleic acid molecule comprising the sequence of SEQ ID NO:8 from nucleotides 258–1964; (c) an isolated nucleic acid molecule comprising the sequence of SEQ ID NO:9 (FIG. 23); (d) an isolated nucleic acid molecule comprising the sequence of SEQ ID NO:10 (FIG. 25); (e) an isolated nucleic acid molecule complementary to any one of the nucleotides of SEQ ID NOS: 8 to 10 set forth in (a) through (d), respectively.

In another aspect, the present invention provides an isolated nucleic acid molecule which is a variant of, or is substantially similar to, the Candida Hsp60 nucleotide molecules described above. In further aspects the present invention provides an isolated nucleic acid molecule comprising a nucleotide sequence that is identical to a segment of contiguous nucleotide bases comprising at least 25% of SEQ ID NOS: 8 to 10 or a complement thereof or an isolated nucleic acid molecule encoding Hsp60 comprising a nucleic acid sequence that encodes a polypeptide comprising any one of the polypeptides according to FIG. 21, 23 or 25, or a variant Hsp60 that is at least 95% homologous to a polypeptide according to any one of FIG. 21, 23 or 25.

In one embodiment, the present invention provides an isolated nucleic acid molecule according as described above, the molecule encoding a polypeptide that is able to be selectively bound by an antibody specific for a *Candida glabrata* Hsp60.

In still another aspect in one aspect the present invention provides an isolated nucleic acid molecule encoding at least 8 contiguous amino acids of a *Candida glabrata* Hsp60 polypeptide selected from amino acid residues according to FIG. 21, wherein the encoded *Candida glabrata* Hsp60 polypeptide is able to bind to a major histocompatibility complex.

In still further aspects the present invention provides an isolated *Candida glabrata* Hsp60 polypeptide.

In some embodiments, the isolated Hsp60 polypeptide comprises the amino acid sequence of FIG. 21, or variants thereof, preferably wherein the polypeptide is able to be selectively bound by an antibody specific for a *Candida glabrata* Hsp60. In further embodiments, the isolated Hsp60 polypeptide is fused to an additional polypeptide to create a fusion protein.

In still yet further aspects the present invention provides an isolated Hsp60 polypeptide comprising at least 8 contiguous amino acids selected from amino acid residues according to FIG. 21, wherein the Hsp60 polypeptide is capable of binding to a major histocompatibility complex and eliciting or enhancing an immune response to *Candida glabrata* in a human being.

In certain embodiments, the isolated Hsp60 polypeptide is derived from proteolytic cleavage or chemical synthesis, or is an expression product of a transformed host cell containing a nucleic acid molecule encoding the Hsp60 or portion thereof. In further certain embodiments, the isolated Hsp60 polypeptide comprises greater than 95% homology to the Hsp60 polypeptide of FIG. 21, and the isolated Hsp60 polypeptide is able to be selectively bound by an antibody specific for a *Candida glabrata* Hsp60.

In still yet another aspect the present invention provides an isolated polypeptide wherein the polypeptide is an expression product of a transformed host cell containing at least one of the aforementioned nucleic acid molecules derived from Candida.

In still yet further aspects the present invention provides vectors comprising at least one of the aforementioned nucleic acid molecules derived from Candida. In certain embodiments, the vector is an expression vector comprising a promoter in operative linkage with the isolated nucleic acid molecule encoding the Hsp60 or portion thereof, preferably further comprising a selectable or identifiable marker and/or wherein the promoter is a constitutive or an inducible promoter. The present invention also provides host cells containing such vectors. In certain embodiments, the host cell is selected from the group consisting of a bacterial cell, a mammalian cell, a yeast cell, a plant cell and an insect cell.

In still yet other aspects the present invention provides compositions comprising a Candida Hsp60 polypeptide in combination with a pharmaceutically acceptable carrier or diluent. In certain embodiments, the composition is suitable for systemic administration, oral administration, intranasal administration or parenteral administration.

In yet other aspects the present invention provides methods for eliciting or enhancing an immune response in a mammal against Candida, comprising administering to the mammal in an amount effective to elicit or enhance the response, a Candida Hsp60 polypeptide in combination with a pharmaceutically acceptable carrier or diluent; methods for eliciting or enhancing an immune response in a mammal to a polypeptide comprising administering to the mammal a fusion protein containing sequences of the polypeptide fused to the Candida Hsp60 polypeptide in combination with a pharmaceutically acceptable carrier or diluent; and methods for eliciting or enhancing an immune response in a mammal against a target antigen comprising administering to the mammal the target antigen joined to a Candida Hsp60 polypeptide in combination with a pharmaceutically acceptable carrier or diluent.

In still another aspect, this invention provides PCR primers and probes for detecting DNA encoding a *Candida glabrata* Hsp60 that includes at least about 15 contiguous bases from any one of SEQ. ID NOS: 8–10, or to compliment thereof. In a related aspect, the invention provides a method for diagnosing the presence of *Candida glabrata* in a subject sample that includes the steps of obtaining a DNA fraction from the subject sample; and performing a PCR amplification of the DNA fraction using at least one PCR primer that includes at least about 15 contiguous bases from any one of SEQ. ID NOS: 8–10, or a compliment thereof.

These and other aspects of the present invention will become evident upon reference to the present specification and the attached drawings. In addition, various references are set forth herein that describe in more detail certain procedures or compositions (e.g., plasmids, etc.); all such references are incorporated herein in their entirety by reference.

BRIEF DESCRIPTION OF THE DRAWINGS

FIG. 1 illustrates the strategy employed to obtain the nucleotide sequence of an internal fragment of the *Neisseria meningitidis* Hsp70 gene.

FIG. 2 depicts the nucleotide and amino acid sequences (SEQ ID NOs: 11 and 12 respectively) of an internal fragment of the *Neisseria meningitidis* Hsp70 gene.

FIG. 3 illustrates the strategy used to obtain the nucleotide and amino acid sequences of the *Neisseria meningitidis* Hsp70 gene.

FIG. 4 depicts first nucleotide and amino acid sequences of *Neisseria meningitis* Hsp70 gene. SEQ.ID.NO.1 (and SEQ.ID.NO.13 respectively).

FIG. 6 depicts second nucleotide and amino acid sequences of *Neisseria meningitis* Hsp70 gene. SEQ.ID.NO.2 (and SEQ.ID.NO.14 respectively).

FIG. 8 depicts the nucleotide and amino acid sequences of *Neisseria meningitidis* Hsp70 gene cloned into pET24A+. SEQ.ID.NO.3 (and SEQ.ID.NO.15 respectively).

FIG. 9 depicts the nucleotide and amino acid sequences of *Neisseria meningitidis* Hsp70 gene cloned into pET28A+. SEQ.ID.NO.4 (and SEQ.ID.NO 16 respectively).

FIG. 14 depicts the nucleotide and amino acid sequences of *Aspergillus fumigatus* Hsp60 gene. SEQ.ID.NO.5 (and SEQ.ID.NOs. 17,18, and 19 respectively).

FIG. 16 depicts the nucleotide and amino acid sequences of *Aspergillus fumigatus* Hsp60 gene in plasmid pETAF60. SEQ.ID.NO.6 (and SEQ.ID.NO 20 respectively).

FIG. 18 depicts the nucleotide and amino acid sequences of *Aspergillus fumigatus* Hsp60 gene in plasmid pETAF60H. SEQ.ID.NO.7 (SEQ.ID.NO.21 respectively).

FIG. 21 depicts the nucleotide and amino acid sequences of *Candida glabrata* Hsp60 gene. SEQ.ID.NO.8 (SEQ.ID.NO 22 respectively).

FIG. 23 depicts the nucleotide and amino acid sequences of *Candida glabrata* Hsp60 gene in plasmid pETCG60A. SEQ.ID.NO.9 (and SEQ ID NO 23 respectively).

FIG. 25 depicts the nucleotide and amino acid sequences of *Candida glabrata* Hsp60 gene in plasmid pETCGA60H. SEQ.ID.NO.10 (and SEQ.ID.NO 24 respectively).

DETAILED DESCRIPTION OF THE INVENTION

Figure 5:
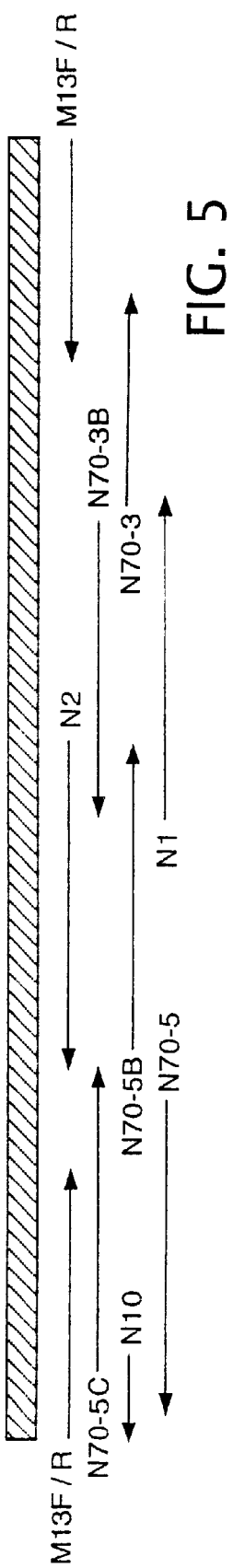
FIG. 5 illustrates strategy employed to obtain second nucleic acid and amino acid sequences of the *Neisseria meningitidis* Hsp70 gene.

The present invention provides methods and compositions comprising isolated nucleic acid molecules and polypeptides specific to *Neisseria meningitidis, Aspergillus fumigatus* and *Candida glabrata,* as well as vector constructs, antibodies and other materials related to isolated nucleic acid molecules and polypeptides. Such compositions and methods are useful for the diagnosis of Neisserial, Aspergillal and Candidal infection and for generating (eliciting or enhancing) an immune response to these organisms.

Prior to setting forth the invention, it may be helpful to an understanding thereof to set forth definitions of certain terms to be used hereafter.

A "stress gene," also known as "heat shock gene," is a gene that is activated or otherwise detectably upregulated due to the contact or exposure of an organism (containing the gene) to a stressor, such as heat shock or glucose deprivation or glucose addition. A given "stress gene" also includes homologous genes within known stress gene families, such as certain genes within the Hsp60, Hsp70 and Hsp90 stress gene families, even though such homologous genes are not themselves induced by a stressor.

A "stress protein," also known as a "heat shock protein," ("Hsp") is a protein that is encoded by a stress gene, and is therefore typically produced in significantly greater amounts upon the contact or exposure to the stressor of the organism. Each of the terms stress gene and stress protein as used in the present specification are inclusive of the other, unless the context indicates otherwise. Neisserial, Aspergillal and Candidal Hsps, as well as Hsps from other organisms, appear to participate in important cellular processes such as protein synthesis and assembly and disassembly of protein complexes.

As used herein, "polypeptide" refers to full length proteins and fragments thereof.

As used herein, "peptide" refers to a fragment of the whole protein, whether chemically or biologically produced.

As used herein, "immunogenic" refers to an antigen or composition that elicits an immune response.

An "isolated nucleic acid molecule" refers to a polynucleotide molecule, in the form of a separate fragment or as a component of a larger nucleic acid construct, that has been separated from its source cell (including the chromosome it normally resides in) at least once in a substantially pure form. Nucleic acid molecules can be comprised of a wide variety of nucleotides and molecules well known in the art, including DNA, RNA, nucleic acid analogues, or any combination of these.

As used herein, "vector" refers to a polynucleotide assembly capable of directing expression and/or replication of the nucleic acid sequence of interest. Such assembly can, if desired, be included as a part of other components, such as a protein, lipid or lipoprotein coat, for delivery of the vector or for other purposes.

An "expression vector" refers to polynucleotide vector having at least a promoter sequence operably linked to the nucleic acid sequence of interest.

As used herein, a "promoter" refers to a nucleotide sequence that contains elements that direct the transcription of an operably linked nucleic acid sequence. At minimum, a promoter contains an RNA polymerase binding site. Promoter regions can also contain enhancer elements which by definition enhance transcription.

A. Hsp Genes and Polypeptides from *Neisseria meningitidis, Aspergillus fumigatus* and *Candida glabrata*

As used herein, "Hsp70" refers to heat shock genes from a Hsp70 family of genes that encode heat shock proteins of approximately 70 kDa, and the heat shock gene products encoded thereby. The nucleotide and amino acid sequences of Hsp70 genes and gene products from *Neisseria meningitidis* are set forth in FIGS. 4, 6, 8 and 9 (SEQ ID NOS: 1–4; such sequences also include the PCR primers used to isolate the Hsp70 genes). As used herein, Hsp60 refers to heat shock genes from the Hsp60 family of genes that encode heat shock proteins of approximately 60 kDa; and the heat shock gene products encoded thereby. The nucleotide and amino acid sequences of Hsp60 genes and gene products from *Aspergillus fumigatus* and *Candida glabrata* are set forth in FIGS. 14, 16, 18, 21, 23 and 25 (SEQ ID NOS: 5–10; such sequences also include the PCR primers used to isolate the Hsp60 genes).

Within the context of this invention, it should be understood that Hsp70 and Hsp60 include wild-type/native protein sequences, as well as other variants (including alleles) and fragments of the native protein sequences. Briefly, such variants may result from natural polymorphisms or be synthesized by recombinant methodology or chemical synthesis, and differ from wild-type proteins by one or more amino acid substitutions, insertions, deletions, or the like. Further, in the region of homology to the native sequence, a variant should preferably have at least 95% amino acid sequence homology, and within certain embodiments, greater than 97% or 98% homology. As used herein, amino acid "homology" is determined by a computer algorithm incorporated in a protein database search program commonly used in the art, and more particularly, as incorporated in the programs BLAST (BLAST™, a computer program) (Altschul et al., *Nucleic Acids Res.* (25) 3389–3402, 1997) or DNA STAR MEGALIGN (DNA STAR MEGALIGN™, a computer program) which return similar results in homology calculations. As will be appreciated by those of ordinary skill in the art, a nucleotide sequence encoding an Hsp or a variant may differ from the native sequences presented herein due to codon degeneracies, nucleotide polymorphisms, or nucleotide substitutions, deletions or insertions.

The aforementioned sequences are useful for generating PCR primers and probes for the detection of *Neisseria meningitidis, Aspergillus fumigatus* or *Candida glabrata*. Thus, one aspect of this invention includes PCR primers and probes for detecting DNA encoding the Hsps disclosed herein. Useful PCR primers typically include at least about 15 contiguous bases from the nucleic acid sequences provided herein, or compliments thereof. More particularly, PCR primers and probes for detection of *Neisseria meningitidis* include at least about 15 contiguous bases from any one SEQ. ID NOS: 1–4 or compliments thereof; PCR primers and probes for detection of *Aspergillus fumigatus* include at least about 15 contiguous bases from any one SEQ. ID NOS: 5–7 or compliments thereof; and PCR primers and probes for detection of *Candida glabrata* include at least about 15 contiguous bases from any one SEQ. ID NOS: 8–10 or compliments thereof. In certain embodiments, PCR primers derived from these sequences can be used in a diagnostic method to detect the presence of a specific microorganism in a subject sample by amplifying DNA isolated from the subject sample to detect the Hsp genes present in any one of *Neisseria meningitidis, Aspergillus fumigatus* or *Candida glabrata* as opposed to other microorganisms. Thus for example, primer pairs comprising 5' CTGCCGTACATCACCATGG 3' (SEQ ID NO:25) with 5' GGCTTCTTGTACTTTCGGC -3' (SEQ ID NO:26); were able to specifically amplify DNA isolated from *Neisseria meningitidis,* but not other microorganisms known to contain Hsps. Similarly, primer pairs derived from an Hsp70 gene isolated from Streptococcus (5' TGACCTTGT-TGAACGTAC -3'(SEQ ID:27) with 5'ACTTCAT-CAGGGTTTAC -3' (SEQ ID NO:28)) were able to amplify DNA isolated from Streptococcus but not Neisseria (See Example 5).

An "isolated nucleic acid molecule encoding *Neisseria meningitidis* Hsp70, *Aspergillus fumigatus* Hsp60" or *Candida glabrata* Hsp60 refers to nucleic acid sequences that are capable of encoding Hsp70 or Hsp60 polypeptides of these organisms. While several embodiments of such molecules are depicted in SEQ ID NOS: 1–10, it should be understood that within the context of the present invention, reference to one or more of these molecules includes variants that are naturally occurring and/or synthetic sequences which are substantially similar to the sequences provided herein and, where appropriate, the protein (including peptides and polypeptides) that are encoded by these sequences and their variants. As used herein, the nucleotide sequence is deemed to be "substantially similar" if: (a) the nucleotide sequence is derived from the coding region of a native gene of *Neisseria meningitidis, Aspergillus fumigatus* or *Candida glabrata* and encodes a peptide or polypeptide that binds to an antibody or HLA molecule that specifically binds to a polypeptide described herein (including, for example, portions of the sequence or allelic variations of the sequences discussed above); or (b) the nucleotide sequences are degenerate (i.e., sequences which encode the same amino acid using a different codon sequence) as a result of the genetic code to the nucleotide sequences defined in (a); or (c) the nucleotide sequence is at least 95% identical to a nucleotide sequence provide herein, or (d) is a complement of any of the sequences described in (a–c). As used herein, "high stringency" are conditions for hybridization of nucleic acids as described in units 6.3 and 6.4 by Ausubel et al., *Current Protocols in Molecular Biology,* vol. 1. John Wiley & Sons (1998).

One aspect of the present invention is the use of *Neisseria meningitidis* Hsp70, *Aspergillus fumigatus* Hsp60 or *Canadida glabrata* Hsp60 nucleotide sequences to produce recombinant proteins for immunizing an animal. Therefore, the use of any length of nucleic acid disclosed by the present invention (preferably 24 nucleotides or longer) which encodes a polypeptide or fragment thereof that is capable of binding to the major histocompatibility complex and eliciting or enhancing an immunogenic response is contemplated by this invention. Immunogenic response can be readily tested by known methods such as challenging a mouse or rabbit with the antigen of interest and thereafter collecting plasma and determining if antibodies of interest are present. Other assays particularly useful for the detection of T-cell responses include proliferation assays, T-cell cytotoxicity assays and assays for delayed hypersensitivity. In determining whether an antibody specific for the antigen of interest was produced by the animal, many diagnostic tools are available, for example, testing binding of labeled antigen to plasma derived antibodies, or using Enzyme-linked immunoassays with tag attached to the antigen of interest.

The *Neisseria meningitidis* Hsp70, *Aspergillus fumigatus* Hsp60 and *Canadida glabrata* Hsp60 genes of this invention can be obtained using a variety of methods. For example, a nucleic acid molecule can be obtained from a cDNA or genomic expression library by screening with an antibody or antibodies reactive to one or more of these Hsps (see, e.g., Sambrook et al., *Molecular Cloning: A Laboratory Manual,* Cold Spring Harbor, 1989; Ausubel et al., *Current Protocols in Molecular Biology,* Greene Publishing, 1987). Further, random-primed PCR can be employed (see, e.g., *Methods in Enzymol.* 254:275, 1995). In one such method, one of the primers is a poly deoxy-thymine and the other is a degenerate primer based on the amino acid sequence or nucleotide sequence of related Hsps.

Other methods can also be used to obtain a nucleic acid molecule that encodes *Neisseria meningitidis* Hsp70, *Aspergillus fumigatus* Hsp60 or *Canadida glabrata* Hsp60. For example, a nucleic acid molecule can be obtained by using the sequence information provided herein to synthesize a probe which can be labeled, such as with a radioactive label, enzymatic label, protein label, fluorescent label, or the like, and hybridized to a genomic library or a cDNA library constructed in a phage, plasmid, phagemid, viral, or other vector (see, e.g., Sambrook et al. (supra); Ausubel et al. (supra)). DNA representing RNA or genomic nucleic acid sequence can also be obtained by amplification using sets of primers complementary to 5' and 3' sequences of the cDNA sequence, such as presented in the Examples. For ease of cloning, restriction sites can also be incorporated into the primers.

Variants (including alleles) of the Hsp70 and Hsp60 genes provided herein can be readily isolated from natural sources containing such variants (e.g., polymorphisms, mutants), or can be synthesized or constructed using recombinant DNA and mutagenesis techniques known in the art. Many methods have been developed for generating mutants (see generally Sambrook et al. (supra); Ausubel et al. (supra)). Briefly, preferred methods for generating nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, such as *E. coli,* other prokaryotes, yeast or other eukaryotes. Standard screening and vector growth protocols are used to identify mutant sequences and obtain high yields.

Similarly, deletions and/or insertions of the Hsp70 or the Hsp60 gene can be constructed by any of a variety of known methods. For example, the gene can be digested with restriction enzymes and religated such that sequence is deleted or religated with additional sequence such that an insertion or large substitution is made. Other means of generating variant sequences, known in the art, can be employed, for examples see Sambrook et al. (supra) and Ausubel et al. (supra). Moreover, verification of variant sequences is typically accomplished by restriction enzyme mapping, sequence analysis or hybridization. Variants which encode a polypeptide that elicits an immunogenic response specific for *Neisseria meningitidis, Aspergillus fumigatus* or *Candida glabrata* are useful in the context of this invention.

As noted above, the present invention also provides isolated polypeptides. Within the context of the present invention, unless otherwise clear from the context, such polypeptides are understood to include the whole, or portions/fragments, of a gene product derived from one or more of the Hsp70 and Hsp60 genes of the invention or variants thereof as discussed above. In one aspect of the present invention, the protein is encoded by a portion of a native gene or is encoded by a variant of a native gene and the protein or fragment thereof elicits or enhances an immune response specific for *Neisseria meningitidis, Aspergillus fumigatus* or *Candida glabrata.*

A "purified" Hsp70 or Hsp60 stress protein of the present invention is a heat shock protein of the Hsp70 or Hsp60 family from *Neisseria meningitidis* (Hsp70), *Aspergillus fumigatus* (Hsp60 ) or *Candida glabrata* (Hsp60 ) that has been purified from its producing cell. For example, the Hsp70 and Hsp60 polypeptides of the present invention can be purified by a variety of standard methods with or without a detergent purification step. For example, Hsp70 or Hsp60 of the present invention can be isolated by, among other methods, culturing suitable host and vector systems to produce recombinant Hsps (discussed further herein). Then, supernatants from such cell lines, or Hsp inclusions, or whole cells where the Hsp is not excreted into the supernatant, can be treated by a variety of purification procedures. For example, the Hsp-containing composition can be applied to a suitable purification matrix such as an anti-Hsp60 antibody bound to a suitable support. Alternatively, anion or cation exchange resins, gel filtration or affinity, hydrophobic or reverse phase chromatography may be employed in order to purify the protein. The Hsp polypeptide can also be concentrated using commercially available protein concentration filters, such as an Amicon or Millipore Pellicon ultrafiltration unit, or by vacuum dialysis. In another alternative, when the polypeptide is secreted the supernatant medium containing the polypeptide can first be concentrated using one of the above mentioned protein concentration filters, followed by application of the concentrate to a suitable purification matrix such as those described above.

In one embodiment, the isolated Hsp70 and Hsp60s of the present invention are produced in a recombinant form, utilizing genetic manipulation techniques that are well known in the art. For example, a Hsp of the present invention can be expressed as a histidine-tagged molecule, permitting purification on a nickel-chelating matrix. Alternatively, other tags may be used, including FLAG and GST. The associated tag can then be removed in the last step of purification, for example, for certain vectors, His-tagged proteins may be incubated with thrombin, resulting in cleavage of a recognition sequence between the tag and the Hsp polypeptide (e.g., pET vectors from Invitrogen). Following purification of an Hsp of the invention from a gram-negative bacterial host, whether tagged or not, it will be necessary to reduce the level of endotoxin in the Hsp preparation.

B. Vectors, Host Cells, and Expression of Hsps from *Neisseria meningitis, Aspergillus fumigatus* and *Candida glabrata*

It is well known in the art that certain vectors (e.g., pUC) can be used for producing multiple copies of a nucleotide molecule of interest as well as being useful for genetic manipulation techniques (e.g., site-directed mutagenesis). See Sambrook (supra). Expression vectors are particularly suited to the practice of this invention. An expression vector includes transcriptional promoter/enhancer elements operably linked to the Neisserial, Aspergillal or Candidal Hsp nucleic acid molecule and may typically contain a selectable or otherwise identifiable marker gene. The expression vector may be composed of either deoxyribonucleic acids ("DNA"), ribonucleic acids ("RNA"), or a combination of the two (e.g., a DNA-RNA chimera). Optionally, the expression vector may include a polyadenylation sequence or one or more restriction sites. Additionally, depending on the host cell chosen and the expression vector employed, other genetic elements such as an origin of replication, additional nucleic acid restriction sites, enhancers, sequences conferring inducibility of transcription, and genes encoding proteins suitable for use as selectable or identifiable markers, may also be incorporated into the expression vectors described herein.

The manipulation and expression of Neisserial, Aspergillal or Candidal Hsp genes can be accomplished by culturing host cells containing an expression vector capable of expressing the Hsp genes. Such vectors or vector constructs include either synthetic or cDNA-derived nucleic acid molecules or genomic DNA fragments encoding the Hsp polypeptides, which are operably linked to suitable transcriptional or translational regulatory elements. Suitable regulatory elements within the expression vector can be derived from a variety of sources, including bacterial, fungal, viral, mammalian, insect, or plant genes. Selection of appropriate regulatory elements is dependent on the host cell chosen, and can be readily accomplished by one of ordinary skill in the art in light of the present specification. Examples of regulatory elements include a transcriptional promoter and enhancer or RNA polymerase binding sequence, a transcriptional terminator, and a ribosomal binding sequence, including a translation initiation signal.

Nucleic acid molecules that encode any of the Neisserial, Aspergillal or Candidal Hsp polypeptides described above can be expressed by a wide variety of prokaryotic and eukaryotic host cells, including bacterial, mammalian, yeast or other fungi, viral, insect, and plant cells. The selection of a host cell may also assist the production of post-translationally modified Hsps (e.g. modified by glycosylation, prenylation, acetylation or other processing event), depending upon the desires of the user. Methods for transforming or transfecting such cells to express nucleic acids are well known in the art (see, e.g., Itakura et al., U.S. Pat. No. 4,704,362; Hinnen et al., *PNAS* USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al., *Molecular Cloning: A Laboratory Manual*, $2^{nd}$ edition, Cold Spring Harbor Laboratory Press, 1989; for plant cells see Czako and Marton, *Plant Physiol.* 104:1067–1071, 1994; Paszkowski et al., Biotech. 24:387–392, 1992).

Bacterial host cells suitable for carrying out the present invention include *E. coli*, such as *E. coli* DH5α (Stratagene, La Jolla, Calif.) or BL21 (DE3) (Novagen, Madison, Wis.), *M. leprae, M. tuberculosis, M. bovis, B. subtilis, Salmonella typhimurium,* and various species within the genera Pseudomonas, Streptomyces, Streptococcus, and Staphylococcus, as well as many other bacterial species well known to one of ordinary skill in the art.

Bacterial expression vectors preferably comprise a promoter, which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60–89, 1990), the lambda promoter (Elvin et al., *Gene* 87:123–126, 1990), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC1 18, pUC119 (see Messing, *Meth. in Enzymology* 101:20–77, 1983; Vieira and Messing, *Gene* 19:259–268, 1982), and pNH8A, pNH16a, pNH18a, and Bluescript M13 (Stratagene, La Jolla, Calif).

Fungal host cells suitable for carrying out the present invention include, among others, *Saccharomyces pombe, Saccharomyces cerevisiae,* the genera Pichia or Kluyveromyces and various species of the genus Aspergillus (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035–1039, 1978), YEp13 (Broach et al., *Gene* 8:121–133, 1979), pJDB249 and pJDB219 (Beggs, *Nature* 275:104–108, 1978) and derivatives thereof.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals,* Hollaender et al. (eds.), p. 355, Plenum, N.Y., 1982; Ammerer, *Meth. Enzymol.* 101:192–201, 1983). Examples of useful promoters for fungi vectors include those derived from *Aspergillus nidulans* glycolytic genes, such as the adh3 promoter (McKnight et al., *EMBO J.* 4:2093–2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers include those that complement host cell auxotrophy, provide antibiotic resistance or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al.(*Proc. Natl. Acad. Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell may contain a genetic defect that is complemented by the selectable marker present on the expression vector. Choice of a particular host and selectable marker is well within the level of ordinary skill in the art in light of the present specification.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include expression vectors that comprise a promoter which directs the expression of an isolated nucleic acid molecule encoding a Hsp according to this invention. A wide variety of promoters may be utilized within the context of the present invention, including for example, promoters such as MoMLV LTR, RSV LTR, Friend MuLV LTR, adenoviral promoter (Ohno et al., *Science* 265: 781–784, 1994), neomycin phosphotransferase promoter/enhancer, late parvovirus promoter (Koering et al., *Hum. Gene Therap.* 5:457–463, 1994), Herpes TK promoter, SV40 promoter, metallothionein IIa gene enhancer/promoter, cytomegalovirus immediate early promoter, and the cytomegalovirus immediate late promoter. The promoter may also be a tissue-specific promoter (see e.g., WO 91/02805; EP 0,415,731; and WO 90/07936). In addition to the above-noted promoters, other viral-specific promoters (e.g., retroviral promoters (including those noted above, as well as others such as HIV promoters), hepatitis, herpes (e.g., EBV), and bacterial, fungal or parasitic-specific (e.g., malarial-specific) promoters may be utilized in order to target a specific cell or tissue which is infected with a virus, bacteria, fungus or parasite.

Thus, Neisserial Hsp70, Aspergillal Hsp60 or Candidal Hsp60 polypeptides of the present invention may be expressed from a variety of viral vectors, including for example, herpes viral vectors (e.g., U.S. Pat. No. 5,288,641), adenoviral vectors (e.g., WO 94/26914, WO 93/9191; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10):1287–1291, 1993; Vincent et al., *Nat. Genet.* 5(2):130–134, 1993; Jaffe et al., *Nat. Genet.* 1(5):372–378, 1992; and Levrero et al., *Gene* 101(2):195–202, 1991), adenovirus-associated viral vectors (Flotte et al., *PNAS* 90(22):10613–10617, 1993), baculovirus vectors, parvovirus vectors (Koering et al., *Hum. Gene Therap.* 5:457–463, 1994), pox virus vectors (Panicali and Paoletti, *PNAS* 79:4927–4931, 1982; and Ozaki et al., *Biochem. Biophys. Res. Comm.* 193(2):653–660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218. Within various embodiments, either the viral vector itself or a viral particle which contains the viral vector may be utilized in the methods and compositions described below.

Mammalian cells suitable for carrying out the present invention include, among others: PC12 (ATCC No. CRL1721), N1E-115 neuroblastoma, SK-N-BE(2)C neuroblastoma, SHSY5 adrenergic neuroblastoma, NS20Y and NG108–15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314), CHO (ATCC No. CCL 61), HeLa (e.g., ATCC No. CCL 2), 293 (ATCC No. 1573; Graham et al., *J. Gen. Virol.* 36:59–72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT2B (Orskov and Nielson, *FEBS* 229(1): 175–178, 1988).

Mammalian expression vectors for use in carrying out the present invention include a promoter capable of directing the transcription of a cloned gene or cDNA. Preferred promoters include viral promoters and cellular promoters. Example viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981), MMTV LTR, RSV LTR, and adenovirus E1a. Example cellular promoters include the mouse metallothionein-1 promoter (Palmiter et al., U.S. Pat. No. 4,579,821), actin promoters, a mouse $V_H$ promoter (Bergman et al., *Proc. Natl. Acad Sci. USA* 81:7041–7045, 1983; Grant et al., *Nucl. Acids Res.* 15:5496, 1987) and a mouse $V_H$ promoter (Loh et al., *Cell* 33:85–93, 1983). The choice of promoter will depend, at least in part, upon the level of expression desired or the recipient cell line to be transfected.

Such expression vectors can also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commnercial sources (e.g., Stratagene, La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc., NY, 1987). See generally Sambrook et al. (supra). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass.).

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215–224,1990).

Numerous plant host cells known in the art can also be useful within the present invention, in light of the subject specification. For example, the use of *Agrobacterium rhizogenes* as vectors for expressing genes in plant cells has been reviewed by Sinkar et al., *J. Biosci.* (Bangalore) 11:47–58, 1987.

Upon expression of the Neisserial Hsp70, Aspergillal Hsp60 or Candidal Hsp60 polypeptides or fragments thereof in the host cells, the polypeptide or peptide may be released and/or isolated from the host cell utilizing methods such as those discussed previously herein.

As noted above, depending on the host cell in which one desires to express an Neisserial, Aspergillal or Candidal Hsp, the gene encoding the protein is introduced into an expression vector comprising a promoter that is active in the host cell. Other components of the expression unit such as transcribed but not translated sequences at the ends of the coding region may also be selected according to the particular host utilized. In some cases, it may be necessary to introduce artificially an intervening sequence to ensure high level expression. Expression can be monitored by SDS-PAGE and staining, if expression levels are sufficiently high. Additionally, if the protein is produced with a tag, detection by anti-tag antibody can be carried out and if produced with no tag, detection by anti-Hsp antibody that does not recognize homologous proteins of the host may be employed. Further, any method known in the art for protein identification may be utilized to this end (e.g., a high resolution electrophoretic method or 2D electrophoresis).

C. Preparation of Antibodies Against the Hsp Polypeptides of the Present Invention In another aspect, the proteins of the present invention are utilized to prepare specifically binding antibodies (i.e., binding partners). Accordingly, the present invention also provides such antibodies. Within the context of the present invention, the term "antibodies" includes polyclonal antibodies, monoclonal antibodies, anti-idiotypic antibodies, fragments thereof such as $F(ab')_2$ and Fab fragments, and recombinantly or synthetically produced binding partners. Such binding partners incorporate the variable regions that permit an antibody to specifically bind, which means an antibody able to selectively bind to a peptide produced from one of the Neisserial, Aspergillal or Candidal Hsp genes of the invention with a Kd of about $10^{-3}$ M or less. The affinity of an antibody or binding partner can be readily determined by one of ordinary skill in the art (see Scatchard, *Ann. N.Y Acad. Sci.* 51:660–672, 1949).

Polyclonal antibodies can be readily generated by one of ordinary skill in the art from a variety of warm-blooded animals such as horses, cows, goats, sheep, dogs, chickens, turkeys, rabbits, mice, or rats. Briefly, the desired protein or peptide is utilized to immunize the animal through intraperitoneal, intramuscular, intraocular, or subcutaneous injections. The immunogenicity of the protein or peptide of interest may be increased through the use of an adjuvant such as Freund's complete or incomplete adjuvant. Following several booster immunizations, small samples of serum are collected and tested for reactivity to the desired protein or peptide.

Typically, suitable polyclonal antisera give a signal that is at least three times greater than background. Once the titer of the animal has reached a plateau in terms of its reactivity to the protein, larger quantities of polyclonal antisera may be readily obtained either by weekly bleedings, or by exsanguinating the animal.

Monoclonal antibodies can also be readily generated using well-known techniques (see U.S. Pat. Nos. RE 32,011, 4,902,614, 4,543,439, and 4,411,993; see also Monoclonal Antibodies, Hybridomas: *A New Dimension in Biological Analyses,* Plenum Press, Kennett, McKearn, and Bechtol (eds.), 1980, and Antibodies: *A Laboratory Manual,* Harlow and Lane (eds.), Cold Spring Harbor Laboratory Press, 1988). Briefly, in one embodiment, a subject animal such as a rat or mouse is injected with a desired protein or peptide. If desired, various techniques may be utilized in order to increase the resultant immune response generated by the protein, in order to develop greater antibody reactivity. For example, the desired protein or peptide may be coupled to another protein such as ovalbumin or keyhole limpet hemocyanin (KLH), or through the use of adjuvants such as Freund's complete or incomplete adjuvant. The initial elicitation of an immune response, may preferably be through intraperitoneal, intramuscular, intraocular, or subcutaneous routes.

Between one and three weeks after the initial immunization, the animal may be reimmunized. The animal may then be test bled and the serum tested for binding to the desired antigen using assays as described above. Additional immunizations may also be accomplished until the animal has reached a plateau in its reactivity to the desired protein or peptide. The animal may then be given a final boost of the desired protein or peptide, and three to four days later sacrificed. At this time, the spleen and lymph nodes may be harvested and disrupted into a single cell suspension by passing the organs through a mesh screen or by rupturing the spleen or lymph node membranes which encapsulate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the protein or peptide of interest that is suitable for generating an immune response as described above. Subsequently, the lymphocytes are harvested and fused as described below.

Cells that are obtained through the use of in vitro immunization or from an immunized animal as described above may be immortalized by transfection with a virus such as the Epstein-Barr Virus (EBV). (See Glasky and Reading, *Hybridoma* 8(4):377–389, 1989.) Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas,* $6^{th}$ ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63—Ag 8.653 (ATCC No. CRL 1580), which may be utilized for fusions with either mouse, rat, or human cell lines. Fusion between the myeloma cell line and the cells from the immunized animal can be accomplished by a variety of methods, including the use of polyethylene glycol (PEG) (see Antibodies: *A Laboratory Manual,* Harlow and Lane, supra) or electrofusion. (See Zimmerman and Vienken, *J. Membrane Biol.* 67:165–182, 1982.)

Following the fusion, the cells are placed into culture plates containing a suitable medium, such as RPMI 1640 or DMEM (Dulbecco's Modified Eagles Medium, JRH Biosciences, Lenexa, Kans.). The medium may also contain additional ingredients, such as Fetal Bovine Serum (FBS, e.g., from Hyclone, Logan, Utah, or JRH Biosciences), thymocytes that were harvested from a baby animal of the same species as was used for immunization, or agar to solidify the medium. Additionally, the medium should contain a reagent which selectively allows for the growth of fused spleen and myeloma cells. Particularly preferred is the use of HAT medium (hypoxanthine, aminopterin, and thymidine) (Sigma Chemical Co., St. Louis, Mo.). After about seven days, the resulting fused cells or hybridomas may be screened in order to determine the presence of antibodies which recognize the desired antigen. Following several clonal dilutions and reassays, hybridoma producing antibodies that bind to the protein of interest can be isolated.

Other techniques may also be utilized to construct monoclonal antibodies. (See Huse et al., "Generation of a Large Combinational Library of the Immunoglobulin Repertoire in Phage Lambda," *Science* 246:1275–1281, 1989; see also Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad Sci. USA* 86:5728–5732, 1989; see also Alting-Mees et al., "Monoclonal Antibody Expression Libraries: A Rapid Alternative to Hybridomas," *Strategies in Molecular Biology* 3:1–9, 1990; these references describe a commercial system available from Stratagene, La Jolla, Calif., which enables the production of antibodies through recombinant techniques.) Briefly, mRNA is isolated from a B cell population and utilized to create heavy and light chain immunoglobulin cDNA expression libraries in the λIMMUNOZAP(H) and λIMMUNOZAP(L) vectors. These vectors may be screened individually or co-expressed to form Fab fragments or antibodies (see Huse et al. (supra); see also Sastry et al. (supra)).

Similarly, binding partners can also be constructed utilizing recombinant DNA techniques to incorporate the variable regions of a gene that encodes a specifically binding antibody. The construction of these binding partners can be readily accomplished by one of ordinary skill in the art given the disclosure provided herein. (See Larrick et al., "Polymerase Chain Reaction Using Mixed Primers: Cloning of Human Monoclonal Antibody Variable Region Genes From Single Hybridoma Cells," *Biotechnology* 7:934–938, 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989; see also U.S. Pat. No. 5,132,405 entitled "Biosynthetic Antibody Binding Sites.") Briefly, in one embodiment, DNA segments encoding the desired protein or peptide of interest-specific antigen binding domains are amplified from hybridomas that produce a specifically binding monoclonal antibody, and are inserted directly into the genome of a cell that produces human antibodies. (See Verhoeyen et al. (supra); see also Reichmann et al. (supra)). This technique allows the antigen-binding site of a specifically binding mouse or rat monoclonal antibody to be transferred into a human antibody. Such antibodies are preferable for therapeutic use in humans because they are not as antigenic as rat or mouse antibodies.

In an alternative embodiment, genes that encode the variable region from a hybridoma producing a monoclonal antibody of interest are amplified using oligonucleotide primers for the variable region. These primers may be synthesized by one of ordinary skill in the art, or may be purchased from commercially available sources. For instance, primers for mouse and human variable regions including, among others, primers for $V_{Ha}$, $V_{Hb}$, $V_{Hc}$, $V_{Hd}$, $C_{H1}$, $V_L$ and $C_L$ regions, are available from Stratagene (La Jolla, Calif.). These primers may be utilized to amplify heavy or light chain variable regions, which may then be inserted into vectors such as IMMUNOZAP™(H) or IMMUNOZAP™(L) (Stratagene), respectively. These vectors may then be introduced into *E. coli* for expression. Utilizing these techniques, large amounts of a single-chain polypeptide containing a fusion of the $V_H$ and $V_L$ domains may be produced (see Bird et al., *Science* 242:423–426, 1988).

Monoclonal antibodies and other binding partners can be produced in a number of host systems, including tissue cultures, bacteria, eukaryotic cells, plants and other host systems known in the art.

Once suitable antibodies or binding partners have been obtained, they may be isolated or purified by many techniques well known to those of ordinary skill in the art (see Antibodies: *A Laboratory Manual,* Harlow and Lane (supra)). Suitable techniques include peptide or protein affinity columns, HPLC or RP-HPLC, purification on protein A or protein G columns, or any combination of these techniques. Within the context of the present invention, the term "isolated" as used to define antibodies or binding partners means "substantially free of other blood components."

The binding partners of the present invention have many uses. For example, antibodies can be utilized in flow cytometry to identify cells bearing such a protein. Briefly, in order to detect the protein or peptide of interest on cells, the cells are incubated with a labeled monoclonal antibody which specifically binds to the protein of interest, followed by detection of the presence of bound antibody. Labels suitable for use within the present invention are well known in the art including, among others, flourescein isothiocyanate (FITC), phycoerythrin (PE), horse radish peroxidase (HRP), and colloidal gold. Particularly preferred for use in flow cytometry is FITC, which may be conjugated to purified antibody according to the method of Keltkamp in "Conjugation of Fluorescein Isothiocyanate to Antibodies. 1. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; Goding, "Conjugation of Antibodies with Fluorochromes: Modification to the Standard Methods," *J. Immunol. Methods* 13:215–226, 1970.) The antibodies can also be used to target drugs to *Neisseria meningitidis, Aspergillus fumigatus* or *Candida glabrata* as well as a diagnostic for determining infection by these organisms.

D. Assays that Utilize the Hsp Polypeptides, or Antibodies thereto, of the Present Invention A variety of assays can be utilized in order to detect the Hsp polypeptides from *Neisseria meningitidis, Aspergillus fumigatus* or *Candida glabrata* of the present invention, or antibodies that specifically bind to such Hsp polypeptides. Exemplary assays are described in detail in Antibodies: *A Laboratory Manual,* Harlow and Lane (eds.), Cold Spring Harbor Laboratory Press, 1988. Representative examples of such assays include: countercurrent immuno-electrophoresis (CIEP), radioimmunoassays, radioimmunoprecipitations, enzyme-linked immuno-sorbent assays (ELISA), dot blot assays, inhibition or competition assays, and sandwich assays, immunostick (dipstick) assays, simultaneous immunoassays, immunochromatographic assays, immunofiltration assays, latex bead agglutination assays, immunofluorescent assays, biosensor assays, and low-light detection assays (see U.S. Pat. Nos. 4,376,110 and 4,486,530; see also Antibodies: *A Laboratory Manual* (supra).

A fluorescent antibody test (FA-test) uses a fluorescently labeled antibody able to bind to one of the proteins of the invention. For detection, visual determinations are made by a technician using fluorescence microscopy, yielding a qualitative result. In one embodiment, this assay is used for the examination of tissue samples or histological sections.

In latex bead agglutination assays, antibodies to one or more of the proteins of the present invention are conjugated to latex beads. The antibodies conjugated to the latex beads are then contacted with a sample under conditions permitting the antibodies to bind to desired proteins in the sample, if any. The results are then read visually, yielding a qualitative result. In one embodiment, this format can be used in the field for on-site testing.

Enzyme immunoassays (EIA) include a number of different assays able to utilize the antibodies provided by the present invention. For example, a heterogeneous indirect EIA uses a solid phase coupled with an antibody of the invention and an affinity purified, anti-IgG immunoglobulin preparation. Preferably, the solid phase is a polystyrene microtiter plate. The antibodies and immunoglobulin preparation are then contacted with the sample under conditions permitting antibody binding, which conditions are well known in the art. The results of such an assay can be read visually, but are preferably read using a spectrophotometer, such as an ELISA plate reader, to yield a quantitative result. An alternative solid phase EIA format includes plastic-coated ferrous metal beads able to be moved during the procedures of the assay by means of a magnet. Yet another alternative is a low-light detection immunoassay format. In this highly sensitive format, the light emission produced by appropriately labeled bound antibodies are quantitated automatically. Preferably, the reaction is performed using microtiter plates.

In an alternative embodiment, a radioactive tracer is substituted for the enzyme mediated detection in an EIA to produce a radioimmunoassay (RIA).

In a capture-antibody sandwich enzyme assay, the desired protein is bound between an antibody attached to a solid phase, preferably a polystyrene microtiter plate, and a labeled antibody. Preferably, the results are measured using a spectrophotometer, such as an ELISA plate reader.

In a sequential assay format, reagents are allowed to incubate with the capture antibody in a step wise fashion. The test sample is first incubated with the capture antibody. Following a wash step, an incubation with the labeled antibody occurs. In a simultaneous assay, the two incubation periods described in the sequential assay are combined. This eliminates one incubation period plus a wash step.

A dipstick/immunostick format is essentially an immunoassay except that the solid phase, instead of being a polystyrene microtiter plate, is a polystyrene paddle or dipstick. Reagents are the same and the format can either be simultaneous or sequential.

In a chromatographic strip test format, a capture antibody and a labeled antibody are dried onto a chromatographic strip, which is typically nitrocellulose or nylon of high porosity bonded to cellulose acetate. The capture antibody is usually spray dried as a line at one end of the strip. At this end there is an absorbent material that is in contact with the strip. At the other end of the strip the labeled antibody is deposited in a manner that prevents it from being absorbed into the membrane. Usually, the label attached to the antibody is a latex bead or colloidal gold. The assay may be initiated by applying the sample immediately in front of the labeled antibody.

Immunofiltration/immunoconcentration formats combine a large solid phase surface with directional flow of sample/reagents, which concentrates and accelerates the binding of antigen to antibody. In a preferred format, the test sample is preincubated with a labeled antibody then applied to a solid phase such as fiber filters or nitrocellulose membranes or the like. The solid phase can also be precoated with latex or glass beads coated with capture antibody. Detection of analyte is the same as standard immunoassay. The flow of sample/reagents can be modulated by either vacuum or the wicking action of an underlying absorbent material.

A threshold biosensor assay is a sensitive, instrumented assay amenable to screening large numbers of samples at low cost. In one embodiment, such an assay comprises the use of light addressable potentiometric sensors wherein the reaction involves the detection of a pH change due to binding of the desired protein by capture antibodies, bridging antibodies and urease-conjugated antibodies. Upon binding, a pH change is effected that is measurable by translation into electrical potential ($\mu$volts). The assay typically occurs in a very small reaction volume, and is very sensitive. Moreover, the reported detection limit of the assay is 1,000 molecules of urease per minute.

The present invention also provides for probes and primers for detecting *Neisseria meningitidis, Aspergillus fumigatus* and *Candida glabrata.*

In one embodiment of this aspect of the invention, probes are provided that are capable of specifically hybridizing to *Neisseria meningitidis, Aspergillus fumigatus* or *Candida glabrata* Hsp genes DNA or RNA. For purposes of the present invention, probes are "capable of hybridizing" to *Neisseria meningitidis, Aspergillus fumigatus* or *Candida glabrata* Hsp gene DNA or RNA if they hybridize under conditions of high stringency (see Sambrook et al. (supra)). Preferably, the probe may be utilized to hybridize to suitable nucleotide sequences under highly stringent conditions, such as 6×SSC, 1×Denhardt's solution (Sambrook et al. (supra)), 0.1% SDS at 65° C. and at least one wash to remove excess probe in the presence of 0.2×SSC, 1×Denhardt's solution, 0.1% SDS at 65° C. Except as otherwise provided herein, probe sequences are designed to allow hybridization to *Neisseria meningitidis, Aspergillus fumigatus* or *Candida glabrata* DNA or RNA sequences, but not to DNA or RNA sequences from other organisms, particularly other bacterial and fungal sequences. The probes are used, for example, to hybridize to nucleic acids that have been isolated from a test sample. The hybridized probe is then detected, thereby indicating the presence of the desired cellular nucleic acid. Preferably, the cellular nucleic acid is subjected to an amplification procedure, such as PCR, prior to hybridization.

Probes of the present invention may be composed of either deoxyribonucleic acids (DNA) or ribonucleic acids (RNA), and may be as few as about 12 nucleotides in length or more typically about 18 to 24 nucleotides or longer comprising a sequence derived from a fragment of the sequences of the *Neisseria meningitidis, Aspergillus fumigatus* or *Candida glabrata* Hsp genes provided by this invention. As used herein, a sequence is "derived from a fragment" when it contains a nucleotide sequences identical to a contiguous nucleotide sequence present in the fragment, or contains a nucleotide sequence that results from reading errors that occur during a PCR amplification of the fragment, or contains a degenerate nucleotide sequence that encodes an amino acid sequence that is identical to or has conservative substations of an amino acid sequence encoded by the fragment. Selection of probe size is somewhat dependent upon the use of the probe, and is within the skill of the art.

Suitable probes can be constructed and labeled using techniques that are well known in the art. Shorter probes of, for example, 12 bases can be generated synthetically. Longer probes of about 75 bases to less than 1.5 kb are preferably generated by, for example, PCR amplification in the presence of labeled precursors such as $[\alpha^{-32}P]dCTP$, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells. (See Sambrook et al. (supra)).

Probes can be labeled by a variety of markers, including for example, radioactive markers, fluorescent markers, enzymatic markers, and chromogenic markers. The use of $^{32}P$ is particularly preferred for marking or labeling a particular probe.

It is a feature of this aspect of the invention that the probes can be utilized to detect the presence of *Neisseria meningitidis, Aspergillus fumigatus* or *Candida glabrata* Hsp mRNA or DNA within a sample. However, if the organisms are present in only a limited number, then it may be beneficial to amplify the relevant sequence such that it may be more readily detected or obtained.

A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), and DNA amplification utilizing LCR or Polymerase Chain Reaction ("PCR") (see U.S. Pat. Nos. 4,683, 195, 4,683,202, and 4,800,159; see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. PCR may also be used in combination with reverse dot blot hybridization (Iida et al., *FEMS Microbiol Lett.* 114.167–172, 1993). PCR products may be quantitatively analyzed by incorporation of dUTP (Duplàa et al., *Anal. Biochem.* 212:229–236, 1993), and samples may be filter sampled for PCR-gene probe detection (Bej et al., *Appl. Environ. Microbiol.* 57:3529–3534, 1991).

Within a preferred embodiment, PCR amplification is utilized to detect *Neisseria meningitidis, Aspergillus fumigatus* or *Candida glabrata* Hsp DNA. Briefly a DNA sample is denatured at 95° C. in order to generate single-stranded DNA. Specific primers are then annealed to the single-stranded DNA at 37° C. to 70° C., depending on the proportion of AT/GC in the primers. The primers are extended at 72° C. with Taq DNA polymerase in order to generate the opposite strand to the template. These steps constitute one cycle, which may be repeated in order to amplify the selected sequence.

Within an alternative preferred embodiment, LCR amplification is utilized for amplification. LCR primers are synthesized such that the 5' base of the upstream primer is capable of hybridizing to a unique sequence in a desired gene to specifically detect a strain of *Neisseria meningitidis, Aspergillus fumigatus* or *Candida glabrata* harboring the desired gene.

Within another preferred embodiment, the probes are used in an automated, non-isotopic strategy wherein target nucleic acid sequences are amplified by PCR, and then desired products are determined by a colorimetric oligonucleotide ligation assay (OLA) (Nickerson et al., *Proc. Natl. Acad. Sci. USA* 81:8923–8927, 1990).

Primers for the amplification of a selected sequence should be selected from sequences that are highly specific and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and can be easily synthesized using techniques well known in the art. PCR products, and other nucleic acid amplification products, may be quantitated using techniques known in the art (Duplàa et al., *Anal. Biochem.* 212:229–236, 1993; Higuchi et al., *Biol. Technology* 11:1026–1030).

Further a biochip array specific for *Neisseria meningitidis, Aspergillus fumigatus* or *Candida glabrata*, comprised of a substrate to which either oligonucleotides, polypeptides or antibodies may be bound can be manufactured using the invention disclosed herein in combination with current biochip technologies. U.S. Pat. No. 5,445,934. By using such a substrate with oligonucleotides derived from the Hsp sequences of this invention or antibodies specific for the Hsp gene products of this invention, a high throughput screening tool can be created to identify the specific Neisseria, Aspergillus or Candida species in many samples.

E. Pharmaceutical Compositions and Methods

By administering a Neisserial, Aspergillal or Candidal Hsp to an animal, the respective Hsp can induce an immune response in the animal to Neisseria, Aspergillus or Candida species, respectively, preferably providing resistance to such bacterial or fungal infection. Accordingly, the isolation of Neisserial, Aspergillal and Candidal Hsp genes and polypeptides of the present invention provides a platform for the generation of compositions containing isolated polypeptides, fragments or variants of Hsps that are useful in diagnosis and treatment of Neisserial, Aspergillal or Candidal associated disorders. As used herein, "treatment" means to administer an agent that prevents or reduces the severity of a disorder caused by an infection by a Neisseria, Aspergillus or Candida species.

Therefore, another aspect of the present invention provides compositions and methods comprising one or more of the above-described Hsp polypeptides or antibodies to Hsps in combination with one or more pharmaceutically or physiologically acceptable carriers, adjuvants, binders or diluents. Such compositions can be used to elicit or enhance an immune response, while antibodies can be used to block progression of disease in a recipient animal, which is preferably a human being, and preferably elicits or enhances a protective or partially protective immunity against *Neisseria meningitidis, Aspergillus fumigatus* or *Candida glabrata,* or against an organism that is targeted by an antigen fused to an Hsp of the present invention.

Preferably, such carriers, adjuvants, binders or diluents are nontoxic to recipients at the dosages and concentrations employed. Ordinarily, the preparation of such compositions entails combining the isolated Hsp polypeptide of this invention with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Examples of adjuvants include alum or aluminum hydroxide for humans.

It will be evident in light of the present specification to those in the art that the amount and frequency of administration can be optimized in clinical trials, and will depend upon such factors as the disease or disorder to be treated, the degree of immune inducement, enhancement, or protection required, and many other factors.

In one embodiment, the composition is administered orally, and the purified Hsp of the invention is taken up by cells, such as cells located in the lumen of the gut. Alternatively, the Hsp composition can be parenterally administrated via the subcutaneous route, or via other parenteral routes. Other routes include buccal/sublingual, rectal, nasal, topical (such as transdermal and ophthalmic), vaginal, pulmonary, intraarterial, intramuscular, intraperitoneal, intraocular, intranasal or intravenous, or indirectly. The Hsp compositions of the present invention can be prepared and administered as a liquid solution, or prepared as a solid form (e.g., lyophilized) which can be administered in solid form or resuspended in a solution in conjunction with administration.

Depending upon the application, quantities of injected Hsp in the composition will vary generally from about 0.1 μg to 1000 mg, typically from about 1 μg to 100 mg, preferably from about 10 μg to 10 mg, and preferably from about 100 μg to 1 mg, in combination with the physiologically acceptable carrier, binder or diluent. Booster immunizations can be given from 2–6 weeks later.

The pharmaceutical compositions of the present invention may be placed within containers, along with packaging material, preferably consumer-acceptable, which provides instructions regarding the use of such pharmaceutical compositions, to provide kits suitable for use within the present invention. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

The Hsp gene products of this invention may also be used as immunological carriers in conjugate vaccines. Hsps are beneficial carriers of antigens because, unlike other carriers, they do not have an immunosuppressive effect. See Barrios et al., *Eur. J. Immunol.* 22:1365–1372, 1992; Suzue and Young, in *Stress-Inducible Cellular Responses* 77:451–465, 1996 (edited by U. Feige et al.). Such carriers may be used to elicit an increased immune response to the conjugated molecule. Alternatively, small Hsp peptides or polypeptides containing antigenic epitopes derived from the larger Hsp polypeptides provided herein, can be conjugated or fused to other carrier proteins to elicit an immunogenic response to the small Hsp antigenic epitope. The Hsp gene products of this invention may therefore be used (in conjugates or fusion proteins) as carriers to elicit an immunogenic response against other target antigens, or as antigens to elicit an immunogenic response against epitopes present on the Hsps.

As used herein, a "fusion protein" is a protein comprised of a Hsp polypeptide, or portion thereof, which is has a peptide bond linkage with an amino acid sequence of an additional polypeptide chain such that a single polypeptide chain is formed which contains an amino acid sequence derived from the Hsp joined with an amino acid sequence derived from the additional polypeptide chain. In one example of typical fusion proteins, a Hsp polypeptide or portion thereof is fused to an additional carrier polypeptide that enhances an immunogenic response in an animal. Example of such polypeptides include but are not limited to keyhole limpet hemocyanin, (KLH) bovine gamma globulin (BGG), serum albumin from various animals (SA) and polypeptides that provide antigenic determinants in addition to that provided by a single Hsp domain. Additional antigenic determinants may include for example, polypeptide domains from more than one Hsp and/or multiple duplications of an antigenic polypeptide domain from a single Hsp. In these cases the target of the immune response of interest is typically the Hsp portion of the fusion protein. Alternatively, a Hsp polypeptide of the present invention can serve as the carrier portion of a fusion polypeptide when the additional polypeptide to which it is fused is the target antigen for eliciting an immunogenic response.

One method for producing a fusion protein is by in frame ligation of a nucleic acid sequence encoding a Hsp with a nucleic acid sequence encoding an additional polypeptide to form a hybrid sequence. The hybrid sequence is inserted into an expression vector to form a construct having the hybrid fragment under the control of a promoter operably linked thereto. The construct is introduced into a suitable host cell capable of expressing the hybrid fragment from the vector sequence. Upon expression, the fusion protein is produced and may be isolated from the host cell. When the host cell is a bacterium, the fusion protein may aggregate into inclusion bodies and be readily isolated using methods well known in the art. Alternatively, the fusion protein may include signaling sequences selected to direct the fusion protein to export from the cell into the extracellular medium in which the host cell is cultured.

A further aspect of the present invention is protection from Neisserial, Aspergillal or Candidal associated diseases by either immunization with the Hsp gene products of the present invention (e.g. by intramuscular injection of an expression vector containing an Hsp gene) or by using gene transfer techniques to deliver a vector containing Hsp genes or fragments thereof to be expressed within the cells of the animal.

The compositions and methodologies described herein are suitable for a variety of uses. To this end, the following examples are presented for purposes of illustration, not limitation.

EXAMPLES

Example 1

Cloning of an Internal Fragment of the *Neisseria meningitidis* Hsp70 Gene

Comparison of previously characterized bacterial Hsp70 (or DnaK) proteins was used to identify conserved regions and design degenerate primers suitable for PCR-amplification of an internal region of the unknown *Neisseria meningitidis* Hsp70 gene.

Forward degenerate primer W247 corresponded to a sequence encoding amino acids 145–150 of the consensus Hsp70 sequence (PAYFND). (;SEQ ID NO:29).
W247: 5'-CCNGCNTAYTTYAAYGAY-3'(SEQ ID NO:30)

Reverse degenerate primer W248 was complementary to a sequence encoding amino acids 476–482 of the consensus Hsp70 sequence (PQIEVTF)(;SEQ ID NO:31).
W248: 5'-RAANGTNACYTCDATYTGNGG-3' (;SEQ ID NO:32).

Note that in all sequences provided herein A corresponds to adenosine, C to cytidine, G to guanosine, T to thymidine, I to inosine, R to A or G, Y to C or T, N to A, C, T or G, K to G or T, M to A or C, S to G or C, W to T or A, B to C, G or T, D to A, G or T, H to A, C or T, and V to A, C or G. Unless specified, all molecular DNA manipulations (plasmid isolation, restriction enzyme digestion, ligation, etc.) were carried on under standard conditions described in Sambrook et al., *Molecular Cloning: A Laboratory Manual*, Cold Spring Harbor, 1989.

PCR reactions were carried out according to Perkin-Elmer's recommendations. All reagents used for PCR reactions were supplied by Perkin-Elmer unless indicated otherwise. Reaction mixtures (total volume of 100 μl) contained 0.5 to 1 μg of genomic DNA, 100 pmoles of each of the degenerate primers (W247 and W248, synthesized by Life Technologies), 500 μM each of dNTPs (New England BioLabs), 1×PCR buffer, 4 mM MgSO4, and 1.25 units of Taq polymerase. Reactions were incubated at 95° C. for 30 seconds, at 51° C. for 3 minutes and then at 72° C. for 1 minute. After repeating the above cycle for a total of 40 times, reactions were incubated at 72° C. for an additional 4 minutes. Genomic DNA from *Neisseria meningitidis* (ATCC13090) was obtained from Dr. Lee Weber (University of Nevada, Reno, Nev., USA).

A PCR fragment of about one kbp in length was isolated from a low-melting point agarose gel by phenol extraction and ligated into pCR2.1 TA cloning vector (Invitrogen) using standard conditions. The ligation reaction was used to transform *E. coli* DH5a cells, and transformants were selected on LB agar plates with kanamycin D. Recombinant plasmids were identified after digestion of plasmid DNA with EcoRI restriction enzyme.

Plasmids containing the above fragment of *Neisseria meningitidis* Hsp70 gene were subjected to DNA sequencing using the dye-terminator method on a Prizm 310 automatic sequencer (ABI). Sequence data were assembled and analyzed using DNA Star (DNASTAR Inc.) as well as DNA Strider (CEA, France) software. *E. coli* dnaK gene and protein sequences available from GenBank were used for comparison purposes during assembly.

Three clones originating from a mixture of three separte PCR reactions were sequenced using M13 forward and reverse universal primers (SEQ ID NOS:33and 34):
M13F: 5'-GTAAAACGACGGCCAG-3'
M13R: 5'-CAGGAAACAGCTATGAC-3'

Sequences obtained were used to design an additional pair of primers (SEQ ID NOS:25 and 26) for sequencing:
N1: 5'-CTGCCGTACATCACCATGG-3'
N2: 5'-GGCTTCTTGTACTTTCGGC-3'

FIG. 1 shows the strategy for sequencing the internal *Neisseria meningitidis* Hsp70 gene fragment.

FIG. 2 lists the DNA sequence of this region (assembled from information obtained from sequencing three Hsp70 gene fragment-containing plasmids).

Example 2

Cloning the Ends of the *Neisseria meningitidis* Hsp70 Gene by Inverse PCR

The so called inverse PCR approach was used to clone missing ends of the *Neisseria meningitidis* Hsp70 gene. From the restriction map of the assembled partial DNA sequence BamHI, EcoRI, HincII and Hind III were chosen as enzymes that do not cut.

Approximately 2 μg of *Neisseria meningitidis* genomic DNA were digested with each of the above enzymes, phenol-extracted, precipitated with ethanol and dissolved in 1×ligation buffer at approx. 80 ng/ml. Fragments were ligated and then used as templates for PCR amplification (40 cycles of 1 minute at 95° C., 2 minutes at 65° C. and 2 minutes at 72° C.) in reaction mixtures (as described above) containing primers nested near the ends of known sequence and pointing outside:

N70-5: 5'-GGTCGGCTCGTTGATGATGCGTTTCAC-3' (SEQ ID NO:35)

N70-3: 5'-GCTTCTGCCAACAAATCTTTGGGTCAG-3' (SEQ ID NO:36)

Only DNA digested with HindIII seemed to produce a specific PCR-generated band after amplification. The 0.9 kbp-long fragment was purified from a low-melting point agarose gel and cloned into pCR2.1 vector. A recombinant containing the fragment was identified, and the inserted fragment was sequenced using M13F and M13R primers. It turned out that cloned fragment had been amplified making use of only the N70-5 primer. Still, it represented a region from the 5' end of the *Neisseria meningitidis* Hsp70 gene. Unfortunately, only 44 nucleotides of new sequence could be determined because a HindIII site happened to be present just upstream from the 5'-end of the previously sequenced internal Hsp70 gene fragment. Nevertheless, the sequence of the fragment allowed the resolution of ambiguities created by the use of the degenerate W247 primer. See region B in FIG. 3 as well as the sequence in FIG. 4.

A *Neisseria meningitidis* (ATCC 13090) genomic library in bacteriophage lambda was prepared using routine procedures and was screened using the above-described internal region of the *Neisseria meningitidis* Hsp70 gene as the probe. A recombinant clone containing the *Neisseria meningitidis* Hsp70 gene was used as template for inverse PCR. Additional primers (pointing towards the interior of the known Hsp70 sequence) were designed near the known ends of the internal Hsp70 fragment in regions not interrupted by RsaI restriction sites. Recombinant phage DNA was digested with RsaI, and resulting fragments were circularized as above.

To amplify the 5'-end region, primers N70-5 (see above) and N70-5B(SEQID NO:37) were used for PCR amplification of the ligation reaction:

N70-5B: 5'-GCCGCTTTGGCATTCGTTATGGAC-3'

To amplify the 3'-end region, primers N70-3 (see above) and N70-3B(SEQ.ID.NO:38) were used for PCR of the ligation reaction:

N70-3B: 5'-GCGTTCGCGTTCGCCTTGCAGTAC-3'

PCR reactions were carried out as described before. PCR products were isolated from low-melting point agarose gels and inserted into vector pCR2.1 as also described before.

Sequencing of cloned PCR products revealed the complete sequence of the 3' end of the *Neisseria meningitidis* Hsp70 gene (and clarification of ambiguities resulting from the use of degenerate primer W247 in the cloning of the internal Hsp70 region) as well as 3'-untranslated sequence (region E in FIG. 3). The nucleotide sequence of the 5' end of the Hsp70 gene was also established (region C in FIG. 3), except for the first 28 bp (which had been removed by RsaI digestion).

To determine the nucleotide sequence at the 5' end of the Hsp70 gene, recombinant phage DNA was digested with restriction enzyme Sau3A, fragments were circularized as before, and the ligation reaction was subjected to PCR using a set of primers located between 5' end of the known Hsp70 sequence and closest internal Sau3A site:

N70-5C: 5'-TTCCGAAAACGGTCAAAC-3' (SEQ ID.NO:39)

N70-5D: 5'-ATGGCCAAACAAGAGTTG-3' (SEQ ID.NO:40)

PCR reaction, isolation of PCR product from a low-melting point agarose gel and ligation into vector pCR2.1 were carried out as described before. The ligation reaction was then PCR-amplified using M13F and N70-5C primers. The resulting PCR product was then purified from an agarose gel using a gel extraction kit from Qiagen and used directly for sequencing using the T7PROM primer. This protocol produced the complete nucleotide of the 5'-end of the Neisseria meningitidis Hsp70 gene as well as 5'-untranslated and promoter sequences (region D in FIG. 3).

FIG. 4 lists the complete nucleotide sequence of the Neisseria meningitidis Hsp70 gene as well as of flanking regions. The derived amino acid sequence of the protein product of the gene is also shown.

Example 3

Neisseria Meningitidis HSP70 Expression Vectors

To clone the Neisseria meningitidis Hsp70-coding region, DNA from a recombinant bacteriophage containing the Hsp70 gene served as the template in a PCR amplification reaction that included primers N70-M and N70-Z, complementary to sequence at the 5'-end (including an NdeI site) and the 3'-end of the Hsp70 gene, respectively.

N70-M: 5'-TACATATGGCAAAAGTAATCGGTATC-3' (SEQ ID NO:41)

N70-Z: 5'-TTTATTTTTTGTCGTCTTTTAC-3' (SEQ ID NO:42)

PCR product was purified from an agarose gel using a gel extraction kit (Qiagen) and ligated into pCR2.1 vector. Two positive clones were identified by EcoRI digestion of miniprep DNA isolated from E. coli DH5a colonies resistant to kanamycin D and further confirmed by restriction analysis using HindIII, NotI, NdeI and ClaI. Inserted DNA was then sequenced using primers M13F, M13R, N1, N2, N70-5, N70-5B, N70-5C, N70-3, N70-3B, as well as new primer N10:

N10: (SEQ ID NO:43) 5'-GTCCAAATAAGCGATAACG-3'

FIG. 5 illustrates the sequencing strategy employed.

The sequence obtained (FIG. 6) differed from that presented in FIG. 3 by an A instead of a G at positions 1528 (counted from the NdeI recognition site) and 1647. Only the first of these differences would also be reflected at the protein level. Because sequence comparisons showed that residue 509 is typically serine, the sequence presented in FIG. 6 was assumed to be the correct sequence.

An NdeI—EcoRI (site located downstream from the stop codon) fragment of the above pCR2.1-based plasmid including the complete Hsp70-coding sequence was inserted in between the NdeI and EcoRI sites of pET24A+ and pET28A+ T7 expression vectors. Positive clones were identified by digestion of DNA isolated from kanamycin resistant transformed DH5a colonies with NdeI and EcoRI and electrophoretic analysis. Single positive clones from each set was sequenced using primers T7PROM, T7TERM, N1, N2, N70-5, N70-5-B, N70-5C, N70-3B and new primers

N20: (SEQ ID NO:44) 5'-GCCGCCAAACGTTTGATC-3',

N21: (SEQ ID NO:45) 5'-ACCATGGGCGGCGTGATG-3',

N22: (SEQ ID NO:46) 5'-GAAGCCAATGCCGAGGAA-3',

N23: (SEQ ID NO:47) 5'-TGCGTCGCCGTTGTTGGC-3',

N24: (SEQ ID NO:48) 5'-GGTATCGCCGTTGGTTGC-3', and

N25: (SEQ ID NO:49) 5'-GAGTTTGTCGCCGTAGTC-3'.

Figure 7:
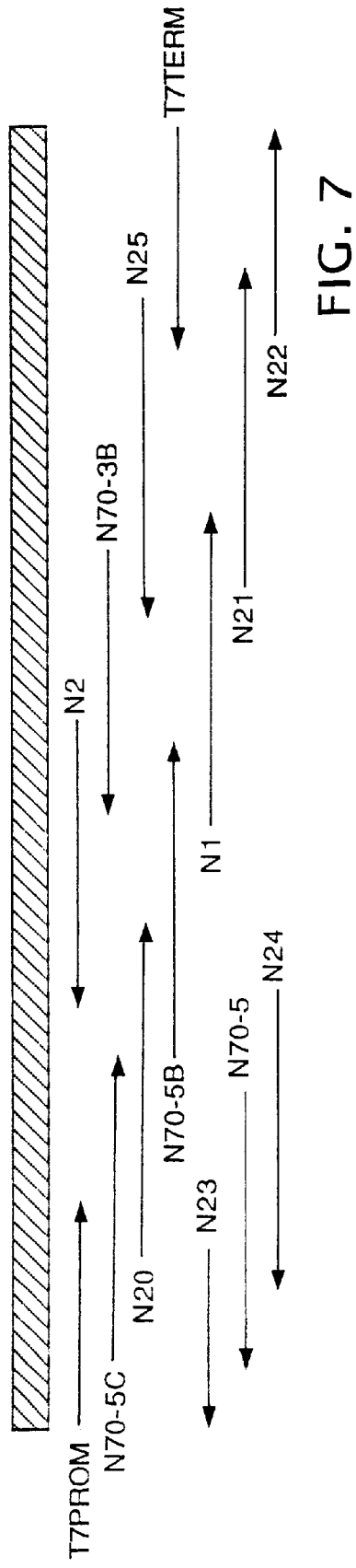
FIG. 7 illustrates the strategy used to obtain nucleic acid and amino acid sequences of the *Neisseria meningitidis* Hsp70 genes cloned into pET24A+ and pET28A+.

With these additional primers, both strands of the Neisseria meningitidis Hsp70 gene could be sequenced in their entireties. The sequencing strategy employed is illustrated in FIG. 7.

FIG. 8 lists the DNA sequence of the Neisseria meningitidis Hsp70 gene in pET24A+ vector (pETN70), and FIG. 9 shows the sequence of its histidine-tagged derivative in pET28A+ vector (pETN70H).

Figure 10:
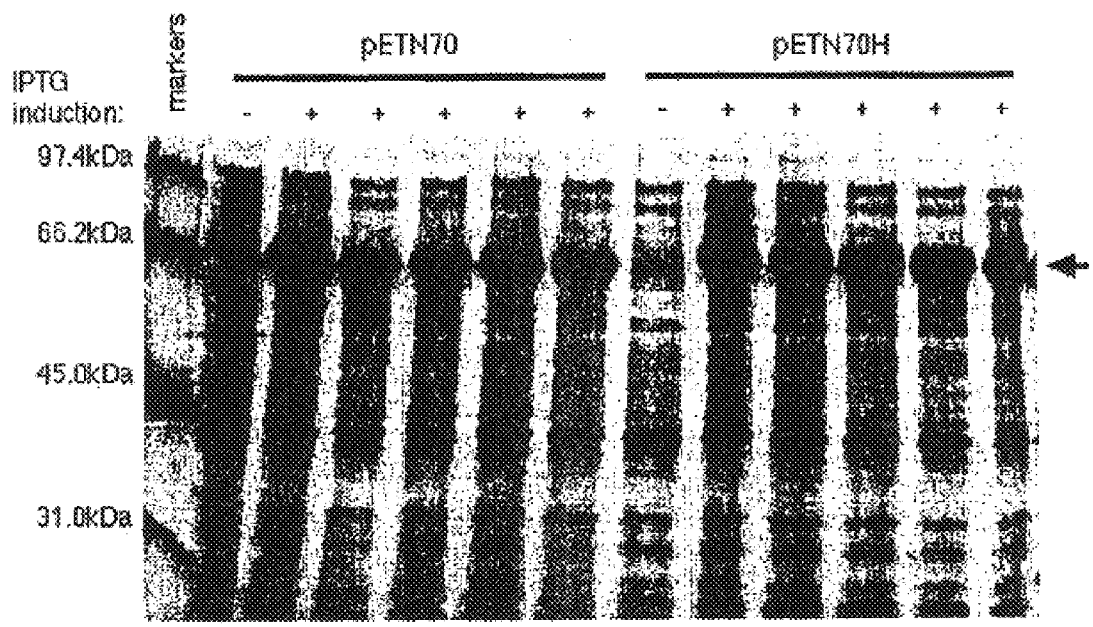
FIG. 10 shows a stained SDS-PAGE gel illustrating expression of recombinant *Neisseria meningitidis* Hsp70.

The functionality of both expression plasmids was confirmed by transformation into E. coli BL21(DE3) cells and detection of the expected protein band after induction with IPTG (1 mM) in small cultures (2×YT medium supplemented with kanamycin D). See FIG. 10.

Example 4

Purification and Characterization of Recombinant Neisseria meningitidis Hsp70 Protein E. coli BL21(DE3) bacteria transformed with pETN70H were grown in 2×YT medium supplemented with 30 mg of kanamycin D at 37° C. to OD600 nm approx. 0.5–0.8 and then induced with 0.5 mM IPTG for 3 hours. Cultures were then chilled on ice, bacteria collected by centrifugation at 600 rpm at 4° C. for 5 minutes and pellets were frozen at −80° C.

Frozen bacterial pellet from a 4 liter culture was crushed, transferred to a blender, and blended in 200 ml of 6M GuHCl, 50 mM Tris-HCl pH7.5, 0.5 mM beta-mercaptoethanol. Lysate was cleared by centrifugation at 8000 rpm at 4° C. for 15 minutes, and the supernatant solution was mixed overnight at room temperature with approximately 40 ml of slurry containing 20 ml of Ni-Sepharose (Chelating Sepharose, Pharmacia) equilibrated with 6M GuHCl, 50 mM Tris-HCl pH7.5, 0.5 mM beta-mercaptoethanol.

Resin was washed on filter paper with approximately 100 ml 6M GuHCl, 50 mM Tris-HCl pH7.5, 0.5 mM beta-mercaptoethanol, resuspended in a small volume of the same buffer and gravity-packed into a glass chromatography column (Pharmacia). The column was washed with 100 ml of buffer containing 6M GuHCl, 50 mM Tris-HCl pH7.5, 0.5 mM beta-mercaptoethanol, 1% Triton X-100. The bound protein was subjected to a buffer gradient (100 ml), beginning with the above buffer and ending with a buffer containing 1M NaCl, 50 mM Tris-HCl pH7.5, 0.5 mM beta-mercaptoethanol. The column was subsequently washed with 100 ml of 1M NaCl, 50 mM Tris-HCl pH7.5, 0.5 mM beta-mercaptoethanol and then with 100 ml of a mixture containing 5% of 1M imidazole, 0.5M NaCl, 50 mM Tris-HCl pH7.5, 0.5 mM beta-mercaptoethanol in 1M NaCl, 50 mM Tris-HCl pH7.5, 0.5 mM beta-mercaptoethanol. Finally, the column was developed with a gradient (100 ml) of 10% to 100% of 1M imidazole, 0.5M NaCl, 50 mM Tris-HCl pH7.5, 0.5 mM beta-mercaptoethanol in 1M NaCl, 50 mM Tris-HCl pH7.5, 0.5 mM beta-mercaptoethanol. Fractions of 5 ml were collected. The flow rate was 4–5 ml/minute, and chromatography was monitored spectrophotometrically (A280 nm).

Figure 11:
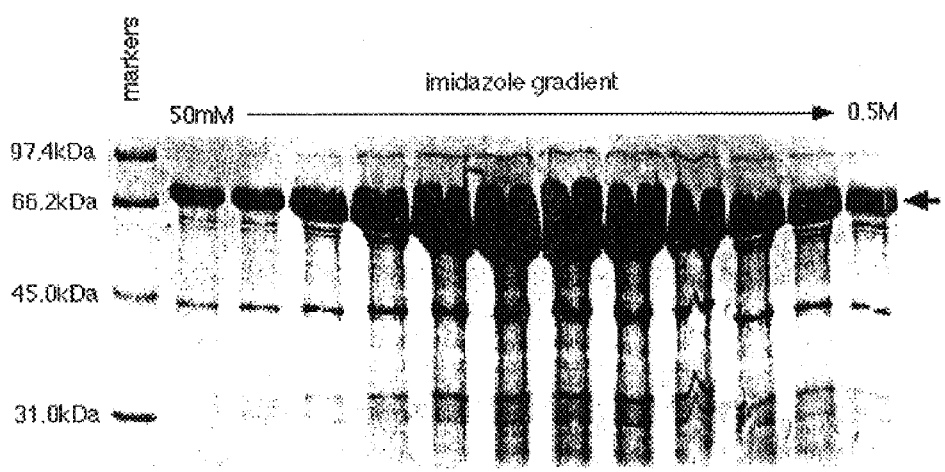
FIG. 11 shows a stained SDS-PAGE gel illustrating purification of recombinant *Neisseria meningitidis* Hsp70.

Fractions containing highest concentrations of recombinant protein were identified by 10% SDS-PAGE and Coomassie blue staining. An example of such an analysis is shown in FIG. 11. Appropriate fractions were pooled (usually 5–6 fractions) into a dialysis bag (12 kDa cutoff and dialyzed against three changes of 1×DPBS (3l) at 4° C. Protein solution was aliquoted and stored on ice or frozen at −80° C. The concentration of the recombinant protein solution was assayed by the Lowry method.

Reactivity with Various Antibodies

Purified recombinant *Neisseria meningitidis* Hsp70 protein was analyzed for reactivity with following Hsp70/DnaK antibodies distributed by StressGen Biotechnologies Corp., Victoria, BC:

A) SPA-810
B) SPA-811
C) SPA-812
D) SPA-815
E) SPA-816
F) SPA-820
G) SPA-822
H) SPA-880
I) SPA-885

Samples containing 0.1 mg, 0.5 mg and/or 1 mg of recombinant protein were fractionated of 10% SDS-PAGE, electroblotted onto nitrocellulose. Blots were blocked with 5% skim milk in phosphate-buffered saline (PBS) containing 0.05% Tween20 overnight at room temperature. Then blots were incubated for 1 hour in the same buffer containing a 1:1000 dilution of each primary antibody. Then blots were washed 3 times (10 minutes each) with PBS, 0.05% Tween20 and incubated for 1 hour in 5% skim milk in PBS, 0.05% Tween20 containing a 1:1000 dilution of goat anti-rabbit IgG antibody-alkaline phosphatase (AP) conjugate (Sigma) or goat-anti-murine IgG-alkaline phosphatase (AP) conjugate (Sigma), depending on the nature of the primary antibody used. Following 3 washes in PBS, 0.05% Tween20 as above, filters were equilibrated in alkaline phosphatase reaction buffer (100 mM Tris-HCl pH9.5, 150 mM NaCl, 10 mM MgCl$_2$) and then developed in 0.05% NBT, 0.05% BCIP in the same buffer.

*Neisseria meningitidis* Hsp70 was not recognized by any of the above antibodies, indicating that this protein is immunologically distinct from the homologous proteins of other microorganisms and of mammals.

Examples 5

Selective Amplification of the *Neisseria meningitidis* Hsp70 Gene

Development of a novel PCR-based diagnostic assay for *Neisseria meningitidis* would require that PCR can be used to discriminate between Hsp70 genes from *Neisseria meningitidis* and other microorganisms. Because bacterial meningitis is caused by *Neisseria meningitidis* and Streptococci, it was further of interest to demonstrate that, by using appropriate primer pairs, Hsp70 genes from both types of organisms can be detected as well as distinguished from one another.

In a first experiment, 20 ng of genomic DNA from *E. coli* (strain DH5alpha), *Helicobacter pylori* (ATCC43504), *Legionella pneumophila* (ATCC33152), *Mycobacterium tuberculosis* (strain H37RV), *Neisseria meningitidis* (ATCC13090), *Streptococcus pneumoniae* (ATCC6314), or *Streptococcus pyogenes* (ATCC12344) were subjected to 40 cycles of PCR under conditions described above using primers specific for the *Neisseria meningitidis* Hsp70 gene N1 and N2.

N1: (SEQ ID NO:25) 5' CTGCCGTACATCACCATGG-3'
N2: (SEQ ID NO:26) 5' GGCTTCTTGTACTTTCGGC-3'

Figure 12:
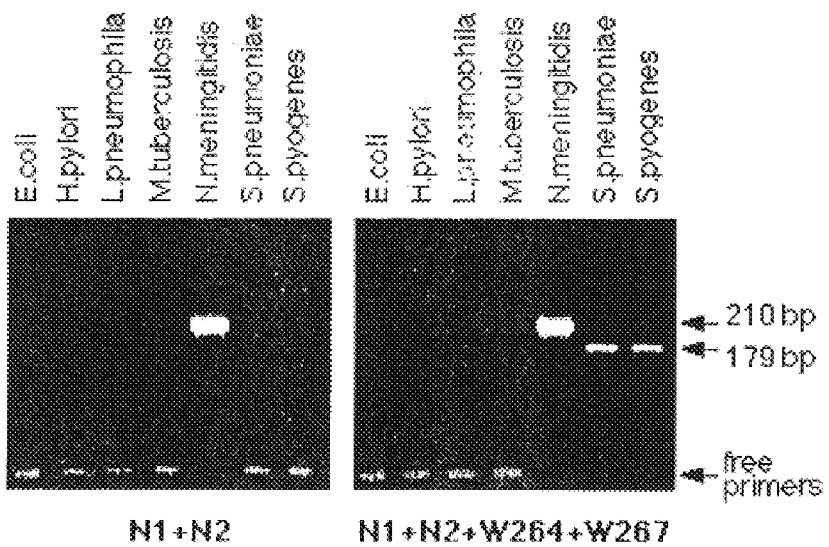
FIG. 12 shows an EtBr-stained gel illustrating selective amplification of *Neisseria meningitidis* Hsp70 and Streptococcal Hsp70 gene sequences.

PCR products were analyzed by electrophoresis on a 2% agarose gel in 0.5×TBE buffer followed by ethidium bromide staining. Only DNA from *Neisseria meningitidis* was specifically amplified (FIG. 12, left panel).

In a second experiment, the same DNAs were subjected to PCR using primer pair N1/N2 and Streptococcal Hsp70-specific primers W264 and W267.

W264: (SEQ ID NO:27) 5' TGACCTTGTTGAACGTAC-3'
W267: (SEQ ID NO:28) 5' ACTTCATCAGGGTTTAC-3'

PCR products were analyzed as before. In these reactions, a 210 bp-long fragment of *Neisseria meningitidis* DNA and a 179 bp-long fragment of streptococcal DNA were amplified (FIG. 12, right panel).

Example 6

Cloning of the *Aspergillus fumigatus* Hsp60 Gene

Genomic DNA preparations from *Aspergillus fumigatus* (ATCC26933) were obtained from ATCC (Rockville, Md.).

A comparison of the few previously characterized yeast (*Saccharomyces cerevisiae* and *Schizosaccharomyces pombe*) Hsp60 genes and of representative bacterial and mammalian Hsp60 genes was used to identify conserved regions and to design degenerate primers suitable for PCR-amplification of fragments of unknown fungal Hsp60 genes.

The following primers were synthesized (Life Technologies) (orientation F-forward, R-reverse, numbers correspond to amino acids of the derived consensus Hsp60 sequence:

F3: (SEQ ID NO:50) 5' -CCATATGAARGANYTNAART TYGGNGT-3' F:37–43
F3A: (SEQ ID NO:51) 5'-AAIGAITTIAAITTTGGIGT-3' F: 37–43
F4: (SEQ ID NO:52) 5'-CTTACATCATNCCNGGCATN CC-3' R: 598–593
F4A: (SEQ ID NO:53) 5'-ACATCATICCIGGCATICC-3' R: 598–593
F5: (SEQ ID NO:54) 5'-CTTACATNCCNCCCA TNCCNCCCAT-3' R: 597–591
F5A: (SEQ ID NO:55) 5'-CATICCICCCATICCICC-3' R: 597–592
F60-C: (SEQ ID NO:56) 5'-GCIGGIGAYGGIACIACIAC-3' F: 118–124
F60-D: (SEQ ID NO:57) 5'-GGWCCMAAGGGHM GWAATGTYTT-3' F: 65–72
F60-E: (SEQ ID NO:58) 5-CCNAARATYACTAAGG AYGGTGT-3' F: 80–87
F60-F: (SEQ ID NO:59) 5'-AARGANTTNAAATTYG GYGT-3' F: 37–43
F60-G: (SEQ ID NO:60) 5'-TCCATNGGRTTRCANCC NGC-3' R: 148–142
F60-H: (SEQ ID NO:61) 5'-ATNACNCCYTCYTTNCC NAC-3' R: 211–205
F60-I: (SEQ ID NO:62) 5'-CATNCCYTCNGTNACYTC-3' R: 230–224
F60-N1: (SEQ ID NO:63) 5'-ACYGARTGTGCYATTGTY GATGC-3' F: 561–569
F60-N2: (SEQ ID NO:64) 5'-ACYGARGTTGCYATTGTY GATGC-3' F: 561–569
F60-O1: (SEQ ID NO:65) 5'-TTAGTTGATGCTTCTGGT GTYGC-3' F: 548–555
F60-O2: (SEQ ID NO:66) 5'-TTAGTTGATGCTAGYGG TGTYGC-3' F: 548–555
F60-P: (SEQ ID NO:67) 5'-GARAARGARAARYTNCA RGA-3' F: 402–408

F60-R: (SEQ ID NO:68) 5'-GCNGCNGTNGARGARGG NAT-3' F: 446–452

CA60-Z: (SEQ ID NO:69) 5'-TTACATGCCGCCCATGC CGCCCATACC-3' R: 597–590

CG60-Z: (SEQ ID NO:70) 5'-TTACATCATACCTGGCATA CCTGG-3' R: 598–592

PCR reactions were carried out according to manufacturers' recommendations using AmpliTaq polymerase (Perkin-Elmer), TaqBeads (Pharmacia) or Taq polymerase (Qiagen) and a Robocycler (Stratagene). Reactions (100ul) contained 0.5 to 1 ug of genomic DNA of *Aspergillus fumigatus* (ATCC26933), 100 pmoles of each degenerate primer, 500 uM each of dNTP (New England BioLabs), 1×manufacturer's PCR buffer, 4 mM MgSO$_4$, and 1.25 units of polymerase. Typically, reactions were incubated at 95° C. for 30 seconds, then at 51° C. for 1 minute and at 72° C. for 1 minute. After repeating the above cycle for a total of 40 times, reactions were incubated at 72° C. for an additional 4 minutes.

PCR-amplified fragments could be obtained with primer pairs F3/F60-I, F60-P/CA60-Z and F3/CG60-Z. The identity of these fragments was determined by sequencing their ends directly (with corresponding degenerate primers) and and/or after cloning into vector pCR2.1 (Invitrogen), in which case M13 universal sequencing primers were used:

M13F: (SEQ ID NO: 33) 5'-GTAAAACGACGGCCAG-3'
M13R: (SEQ ID NO: 34) 5'-CAGGAAACAGCTATGAC-3'

Prizm310 automatic sequencer and dye-terminator technology (ABI) were used for sequencing.

Figure 13:
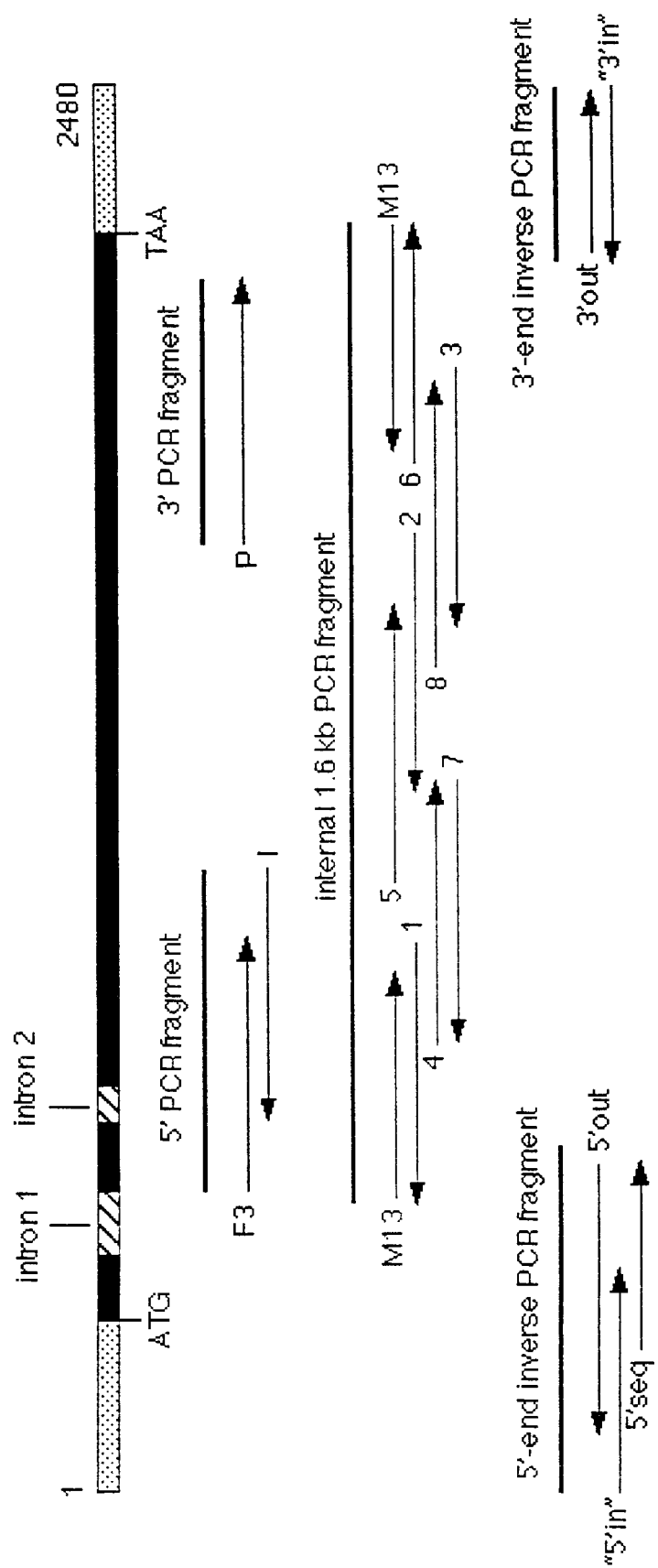
FIG. 13 illustrates the strategy employed to obtain second nucleic acid and amino acid sequences of the *Aspergillus fumigatus* Hsp60 gene.

The amplified fragments contained sequences from near the 5' end, from near the 3' end or from a 1.6 kbp-long central region (FIG. 13). The strategy used to sequence three independent clones containing the 1.6 kbp-long fragment is shown in FIG. 13. In addition to the M13 primers, a set of custom primers was also used for sequencing:

AF1: (SEQ ID NO:71) 5'-CCGGTGGTGATGTCACGC-3'
AF2: (SEQ ID NO:72) 5'-TTGATGACGGCAACACCG-3'
AF3: (SEQ ID NO:73) 5'-AACTCGTCGGTCAGCTTG-3'
AF4: (SEQ ID NO:74) 5'-AGAACCTCGGTGCTCGCC-3'
AF5: (SEQ ID NO:75) 5'-CGCCATGGAGCGTGTTGG-3'
AF6: (SEQ ID NO:76) 5'-TGCTGTTGAGGAGGGTAT-3'
AF7: (SEQ ID NO:77) 5'-ATGATGTCCTGAACGGCA-3'
AF8: (SEQ ID NO:78) 5'-CTGGGCGATCTTGCCGTC-3'

Inverse PCR was then used to isolate DNA fragments containing native ends of the *Aspergillus fumigatus* Hsp60 gene. Based on the sequence obtained from the above fragments, the inverse PCR primers shown below were synthesized ("out" and "in" indicates primer orientation toward outside or inside of the known partial sequence, respectively). For inverse PCR of the 5'-end region, the following primers were used:

AF60-5'in: (SEQ ID NO:79) 5'-GGTCGTAACGTCCTTAT CGAG-3'
AF60-5'out:(SEQ ID NO:80) 5'-AGAGTCGAAGTCACG GCCTT-3'

For inverse PCR of the 3'-end region, the following primers were used:

AF60-3'in: (SEQ ID NO:81) 5'-CCTCAACAATAGCGACC TCAGT-3'
AF60-3'out: (SEQ ID NO:82) 5'-CCCCGCTGCTCCTGGC AT-3'

*Aspergillus fumigatus* genomic DNA was digested with RsaI (for 5'-end inverse PCR) or Sau3A (for 3'-end inverse PCR) restriction enzymes, ligated using T4 DNA ligase and amplified with the appropriate set of inverse PCR primers. The resulting PCR fragments were isolated from gel slices using Qiagen spin columns and were sequenced directly as above using inverse primers as well as an additional sequencing primer (FIG. 13):

AF60-5'seq: (SEQ ID NO:83) 5'-TCGGGCAGTAGTGTTC ATC-3'

The complete sequence of the *Aspergillus fumigatus* Hsp60 gene is shown in FIG. 14.

Comparison of the *Aspergillus fumigatus* Hsp60 sequence with fungal Hsp60 DNA and protein sequences available from GenBank revealed that the *Aspergillus fumigatus* Hsp60 gene contains two introns located at the same relative positions as introns in *Histoplasma capsulatum*, *Paracoccidioides brasiliensis* and *Coccidioides immitis* Hsp60 genes.

Example 7

*Aspergillus fumigatus* Hsp60 Expression Plasmid

The above-discussed 1.6 kbp-long internal fragment of the *Aspergillus fumigatus* Hsp60 gene encompasses exon 2, intron 2 and exon 3 (except for the last few residues after the GGM repeats), and therefore has the sequence information for a protein closely resembling processed Hsp60 proteins. See Singh et al. (1990) Biochem. Biophys. Res. Commun. 169(2), 391–396).

To prepare a T7 expression plasmid for production of *Aspergillus fumigatus* Hsp60 in bacteria, intron 2 sequences had to be removed. Exons 2 and 3 were amplified separately using primers placing the recognition sequence for restriction enzyme EarI (underlined in primer sequences) at the former intron-exon junction. PCR amplification was carried out using a pCR2.1 clone containing the 1.6 kbp *Aspergillus fumigatus* Hsp60 gene fragment.

Exon 2 was amplified using primers M13R and AF60-EX1R:

AF60-EX1R: (SEQ ID NO:84) 5'TTT<u>CTCTTCT</u> ATCCTTGGTGATCTTAGGGGAGC-3'

Exon 3 was amplified with primers M13F and AF60-EX2F:

AF60-EX2F: (SEQ ID NO:85) 5'-TTT<u>CTCTTCA</u> GATGGTGTCTCTGTTGCCAAG-3'.

The resulting PCR fragments were purified from gel slices using Qiagen spin columns, and the DNAs were digested with EarI. Fragments were ligated using T4 DNA ligase, and ligation products were PCR amplified using primers M13R and CG60-ZB.

CG60-ZB: (SEQ ID NO:86) 5'-TTGGATTCTACATCATAC CTGGCATAC-3'

The resulting PCR fragment was purified as above, digested with NdeI and BamHI enzymes and ligated into NdeI-BamHI digested pET24A+ and pET28A+ vectors, respectively. Recombinant plasmids, pETAF60 and pETAF60H, respectively, were identified by restriction analysis and confirmed by sequencing using the same set of AF primers that were used for sequencing the 1.6 kbp fragment (see above) and the following T7 promoter and T7 terminator primers:

T7 promoter: (SEQ ID NO:87) 5'-TAATACGACTCAC TATAGG-3'
T7 terminator: (SEQ ID NO:88) 5'-GCTAGTTATTGCT CAGCGG-3'

Figure 15:
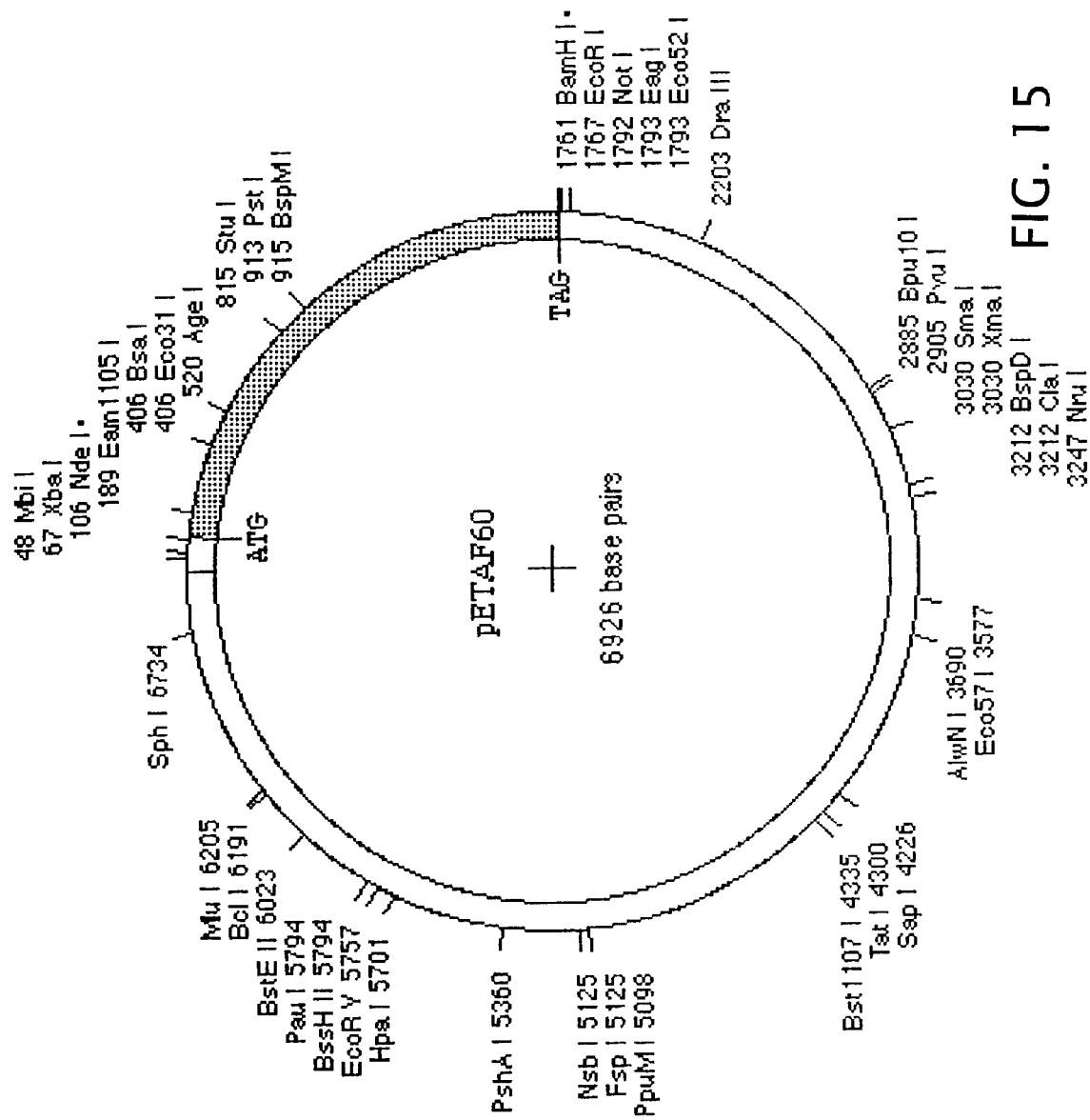
FIG. 15 shows the map of expression plasmid pETAF60.
Figure 17:
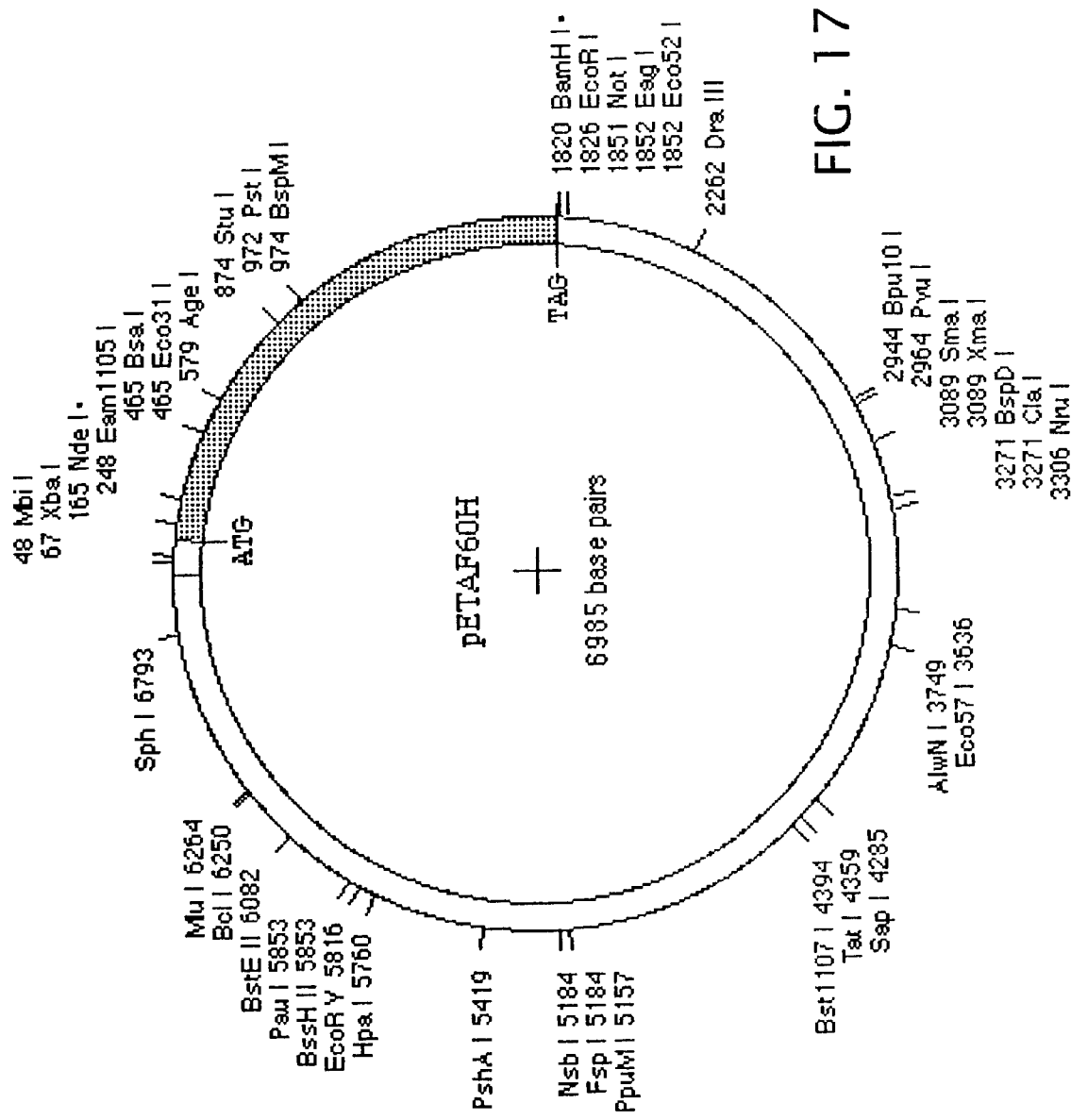
FIG. 17 shows the map of expression plasmid pETAF60H.

FIG. 15 depicts the map of pETAF60 containing a recombinant *Aspergillus fumigatus* Hsp60 gene fragment. The Hsp60-coding sequence is shown in FIG. 16. FIGS. 17 and 18 provide the analogous information on pETAF60H encoding a histidine-tagged Hsp60 protein.

Example 8

Expression of Recombinant *Aspergillus fumigatus* Hsp60

Figure 19:
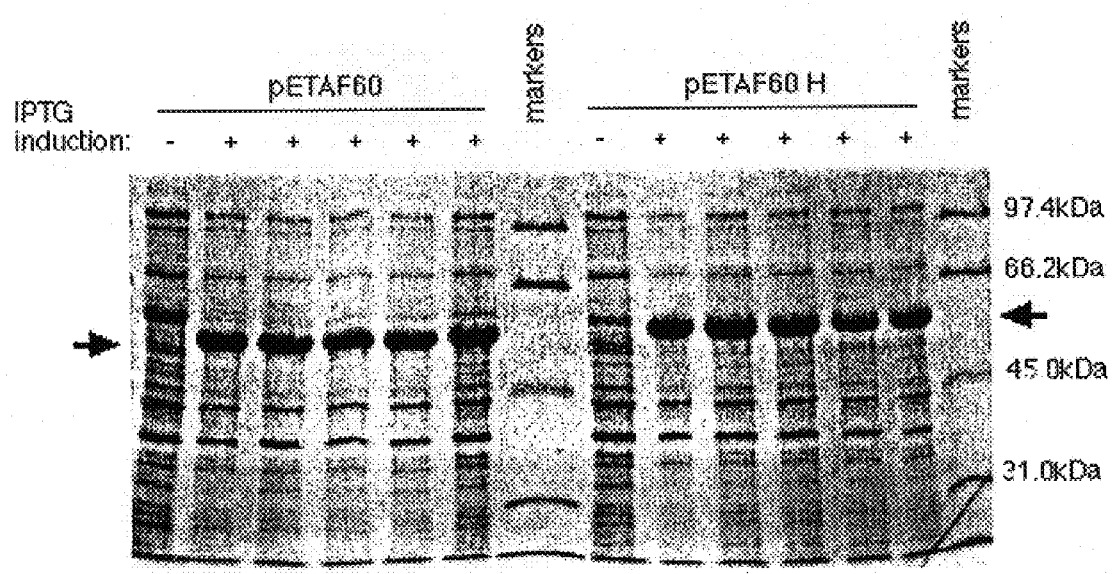
FIG. 19 shows a stained SDS-PAGE gel illustrating expression of recombinant *Aspergillus fumigatus* Hsp60.

Plasmids ETAF60 and ETAF60H were introduced into *E. coli* BL21(DE3) cells by transformation, and expression of fungal Hsp was examined after induction with IPTG. Data presented in FIG. 19 demonstrate induction of prominent band corresponding to a protein of approx. 57 kDa (indicated by arrowhead) in cells transformed with pETAF60. Note that the subunit molecular weight of *Aspergillus fumigatus* Hsp60 is predicted to be 62 kDa. The protein band induced in cells transformed with pETAF50H migrates somewhat slower, as would be expected since the encoded protein also includes a histidine tag (FIG. 19). Recombinant, histidine-tagged *Aspergillus fumigatus* Hsp60 was purified using a protocol similar to that described under Example 4.

Example 9

Cloning of the *Candida flabrata* Hsp60 Gene

Genomic DNA preparations from *Candida glabrata* (ATCC15545) were obtained from ATCC (Rockville, Md.).

An internal 1.6 kbp-long region of the *Candida glabrata* Hsp60 gene was PCR amplified from genomic DNA by AmpliTaq (Perkin-Elmer) using degenerate primers F3 and F4A. (See Example 6). Products of this reaction as well as DNA amplified in two separate reactions using primers F3 and CG60-Z were cloned into vector pCR2.1 and sequenced using primers M13F and M13R and the following custom primers:

CG-1: (SEQ ID NO:89) 5'-CCTATGGATTTGAGAAGG-3'
CG-2: (SEQ ID NO:90) 5'-CTGATAATGTCAACTCCC-3'
CG-3: (SEQ ID NO:91) 5'-GATCTCTTCCATCCAAGAC-3'
CG-4: (SEQ ID NO:92) 5'-GTCCTTGGAGCCGTTACC-3'
CG-5: (SEQ ID NO:93) 5'-GGTAACGGCTCCAAGGAC-3'
CG-6: (SEQ ID NO:94) 5'-GTCTTGGATGGAAGAGATC-3'
CG-8: (SEQ ID NO:95) 5'-CCTTCTCAAATCCATAGG-3'
CG-9: (SEQ ID NO:96) 5'-GGGAGTTGACATTATCAG-3'

Inverse PCR was used to isolate DNA fragments containing the ends of the *Candida glabrata* Hsp60 gene. To isolate the 3'-end region, *Candida glabrata* genomic DNA was digested with RsaI, processed as discussed before, and amplified with CG-2 as "in" primer and the following inverse PCR "out" primer:

CG60-3: (SEQ ID NO:97) 5'-GTTGCTTCCTTGTTGGC TACTACC-3'

The resulting PCR fragment was isolated and cloned into pCR2.1 vector and sequenced using M13F and M13R primers.

To obtain 5'-end region of the *Candida glabrata* Hsp60 gene, Rsa I-digested genomic DNA was ligated and PCR amplified with following inverse PCR primers:

CG60-5 (out): (SEQ ID NO:98) 5'-CCCCAGCGTGGC AGAGACAGCGTC-3'
CG60-5B (in): (SEQ ID NO:99) 5'-GAGAACATGGGT GCTAAGCTTCTG-3'

The resulting PCR fragment was sequenced directly. This yielded 13 bp of additional sequence as well as the natural sequence of the *Candida glabrata* Hsp60 gene in a region previously derived from the degenerate primer F3 only. To obtain additional sequence from the 5i end, the following new primers were designed and used to amplify MspI digested and ligated genomic DNA:

CG60-F (out): (SEQ ID NO:100) 5'-CAGCTCTGCCTTC GACACCGAA-3'
CG60-H (in): (SEQ ID NO:101) 5'-ATCACCAAGGATG GTGTCACCGT-3'

Figure 20:
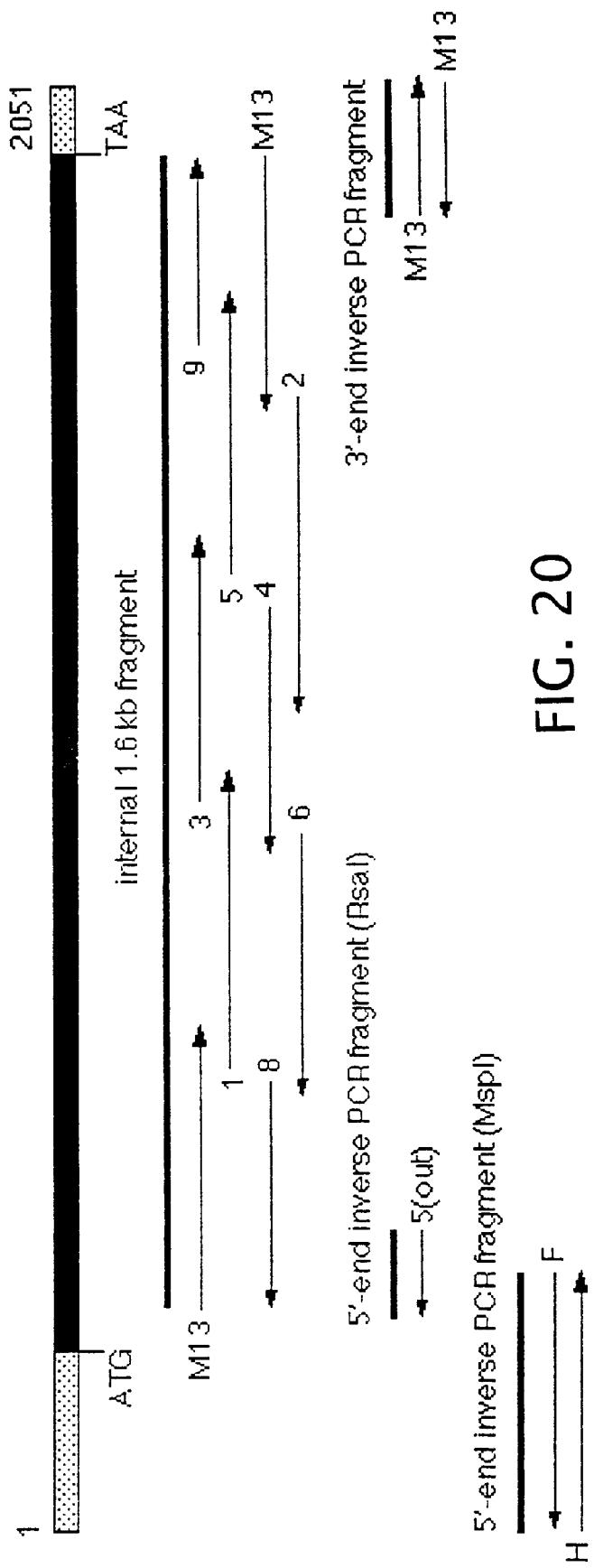
FIG. 20 illustrates the strategy employed to obtain nucleic acid and amino acid sequences of the *Candida glabrata* Hsp60 gene.

Sequencing of the DNA fragment amplified using these primers revealed the complete sequence of the 5'-end of the *Candida glabrata* Hsp60 gene. The sequencing strategy is illustrated in FIG. 20, and the complete DNA sequence of the *Candida glabrata* Hsp60 gene and of its predicted translation product are provided in FIG. 21.

Example 10

*Candida glabrata* Hsp60 Expression Plasmids

An internal 1.6 kbp-long fragment of the *Candida glabrata* Hsp60 gene cloned in vector pCR2.1 (see before and in FIG. 20) was PCR-amplified using primers CG60-Z and CG60-MA:

CG60-MA: (SEQ ID NO:102) 5'-GATATACATATGGC CAAGGAGTTGAAG-3'

PCR amplification with these primers and insertion of the amplified DNA into pET24A+ adds a methionine and an alanine upstream from the first codon encoded by the 1.6 kbp fragment of the *Candida glabrata* Hsp60 gene. Thus, the *Candida glabrata* Hsp60 expression construct (in vector pET24A+) encodes a protein starting with the sequence MAKELK, which closely resembles typical bacterial Hsp60 N-terminus. The C-terminus of the encoded protein corresponds to the natural *Candida glabrata* sequence and contains PGM repeats (see FIGS. 23 and 25).

The above PCR fragment was not only cloned into the pET24A+ but also into the pET28A+ T7 expression vector. Recombinant plasmids were identified by restriction analysis and confirmed by DNA sequencing.

Figure 22:
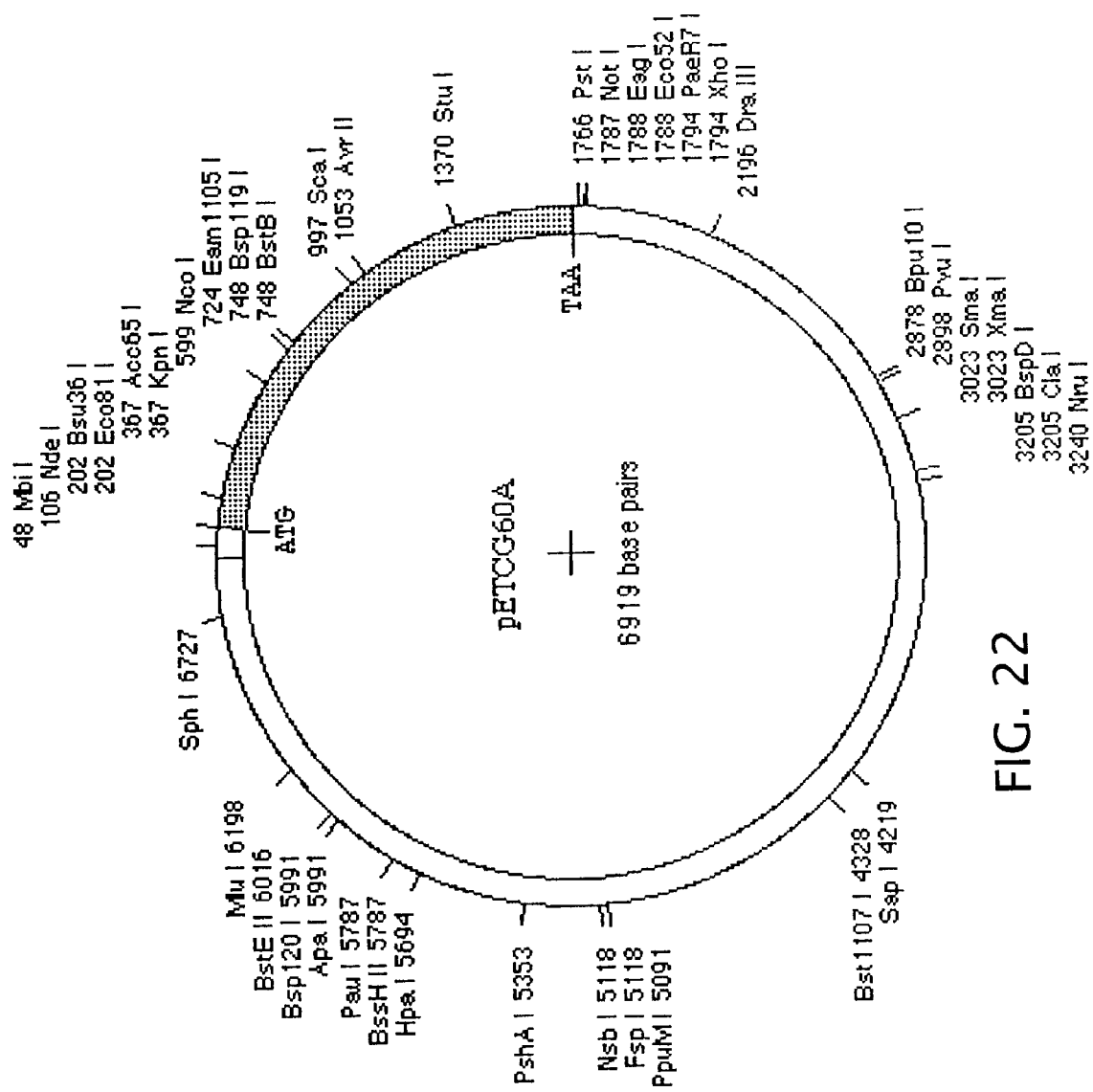
FIG. 22 shows the map of expression plasmid pETCG60A.
Figure 24:
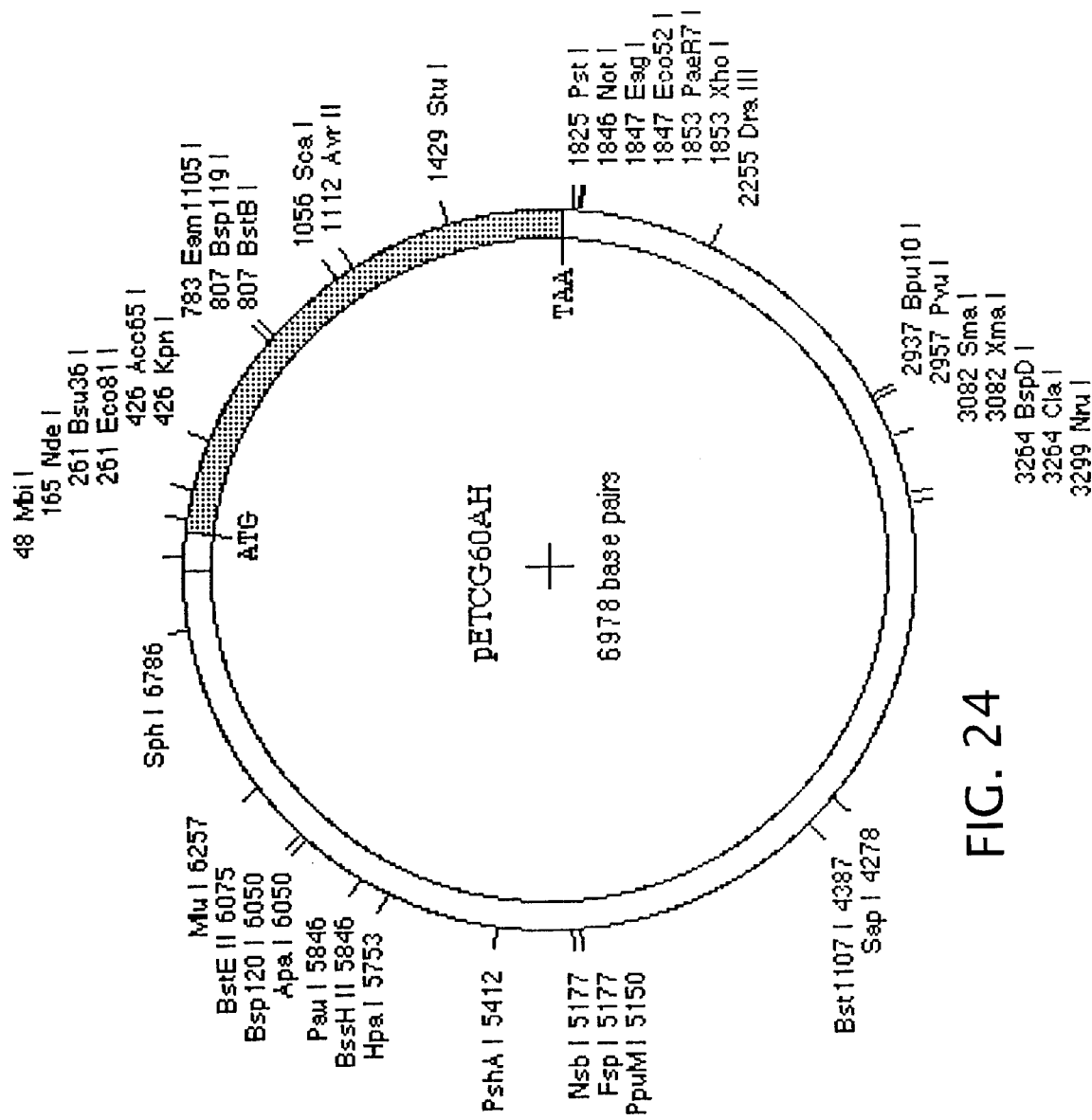
FIG. 24 shows the map of expression plasmid pETCG60AH.

FIGS. 22 and 23 provide the restriction map and relevant nucleotide sequence of the pET24A+-derived expression plasmid pETCG60A, and FIGS. 24 and 25 of the pET28A+-derived expression plasmid pETCG60AH.

Example 11

Expression and Purification of Recombinant *Candida glabrata* Hsp60

Figure 26:
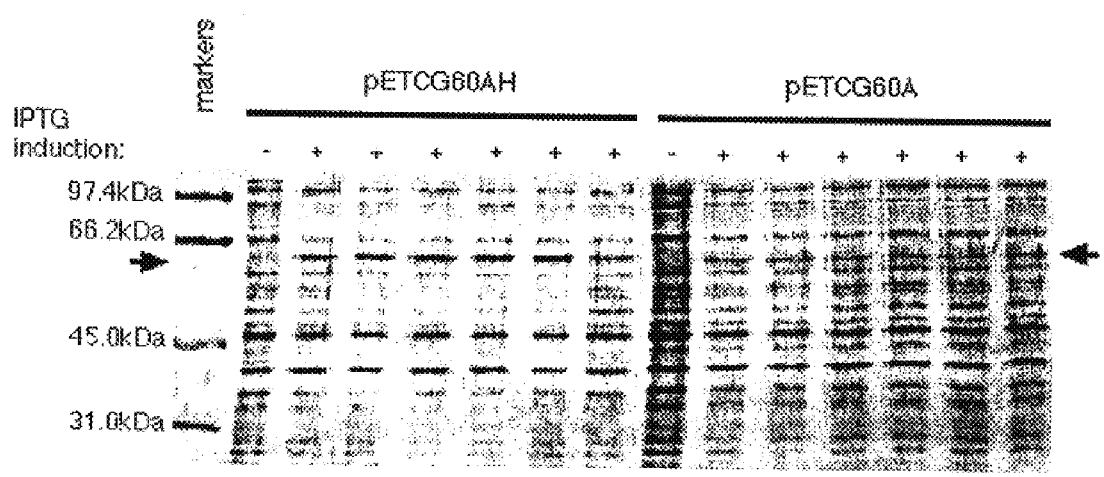
FIG. 26 shows a stained SDS-PAGE gel illustrating expression of recombinant *Candida glabrata* Hsp60.

*E. coli* BL21 (DE3) was transformed with pETCG60A and pETCG60AH, and expression of recombinant protein was monitored after induction with IPTG. Data presented in FIG. 26 demonstrate low-level, induced expression of a recombinant protein of approximately 60 kDa (indicated by arrowhead) in cells transformed with pETCG60 and of a slightly larger protein in cells transformed with pETCG60H.

Figure 27:
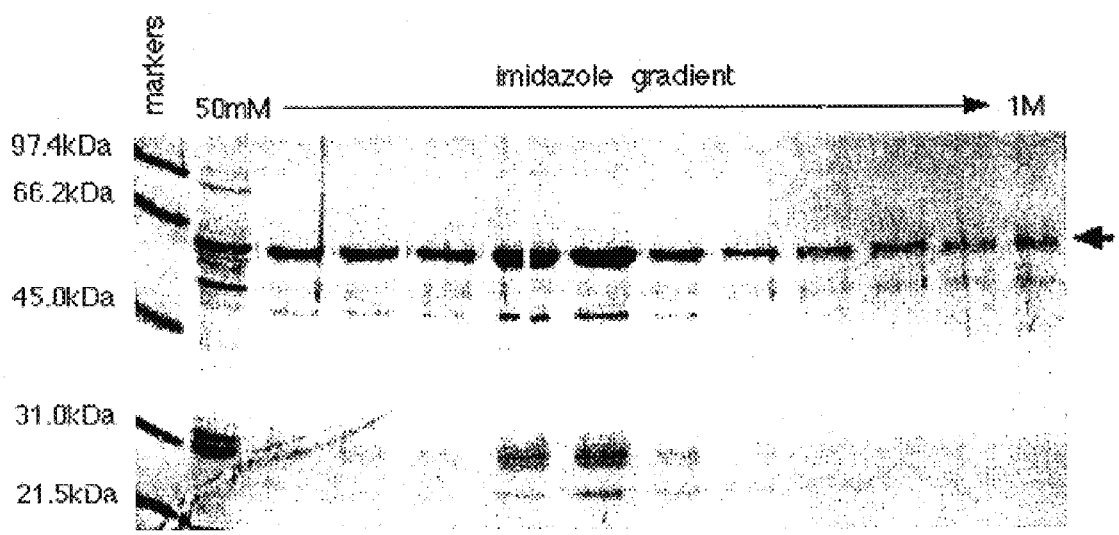
FIG. 27 shows a stained SDS-PAGE gel illustrating purification of recombinant *Candida glabrata* Hsp60.

Despite low expression level, His-tagged recombinant *Candida glabrata* Hsp60 could be effectively purified on a Ni-Sepharose column as illustrated in FIG. 27. The purification protocol used was similar to that described under Example 4.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising the amino acid sequence of at least one of SEQ ID NO:17, SEQ ID NO:18, or SEQ ID NO:19.

2. An isolated polypeptide comprising an amino acid sequence that is at least 95% homologous to the protein encoded by SEQ ID NO:5, wherein the polypeptide comprises a peptide of at least 8 contiguous amino acids of the protein encoded by SEQ ID NO:5, wherein the peptide binds to a major histocompatibility complex molecule, and wherein percent homology is determined according to an algorithm incorporated in a protein database search program used in BLAST (BLAST™, a computer program) or DNA STAR MEGALIGN (DNA STAR MEGALIGN™, a computer program).

3. The polypeptide of claim 1, wherein the polypeptide comprises the amino acid sequence of SEQ ID NO:17.

4. The polypeptide of claim 1, wherein the polypeptide comprises the amino acid sequence of SEQ ID NO:18.

5. The polypeptide of claim 1, wherein the polypeptide comprises the amino acid sequence of SEQ ID NO:19.

6. The polypeptide of claim 1, wherein the polypeptide comprises an amino acid sequence encoded by SEQ ID NO:5.

7. A composition comprising the polypeptide of claim 1 and a pharmaceutically acceptable carrier or diluent.

8. The composition of claim 7, wherein the pharmaceutically acceptable carrier or diluent is suitable for systemic or parenteral administration.

9. The composition of claim 7, wherein the pharmaceutically acceptable carrier or diluent is suitable for oral or intranasal administration.

10. The isolated polypeptide of claim 1, wherein the polypeptide is fused to a heterologous polypeptide to create a fusion protein.

11. The isolated polypeptide of claim 2, wherein the amino acid sequence is at least 97% homologous to the protein encoded by SEQ ID NO:5.

12. The isolated polypeptide of claim 2, wherein the amino acid sequence is at least 98% homologous to the protein encoded by SEQ ID NO:5.

13. The isolated polypeptide of claim 2, wherein the polypeptide is identical to the protein encoded by SEQ ID NO:5.

14. A composition comprising the polypeptide of claim 2 and a pharmaceutically acceptable carrier or diluent.

15. The composition of claim 14, wherein the pharmaceutically acceptable carrier or diluent is suitable for systemic or parenteral administration.

16. The composition of claim 14, wherein the pharmaceutically acceptable carrier or diluent is suitable for oral or intranasal administration.

17. The isolated polypeptide of claim 2, wherein the polypeptide is fused to a heterologous polypeptide to create a fusion protein.

* * * * *